(12) United States Patent
Burnett et al.

(10) Patent No.: US 7,902,157 B2
(45) Date of Patent: Mar. 8, 2011

(54) AZETIDINE AND AZETIDONE DERIVATIVES USEFUL IN TREATING PAIN AND DISORDERS OF LIPID METABOLISM

(75) Inventors: Duane A. Burnett, Bernardsville, NJ (US); Brian A. McKittrick, New Vernon, NJ (US)

(73) Assignee: Schering Corporation, Kenilworth, NJ (US)

( * ) Notice: Subject to any disclaimer, the term of this patent is extended or adjusted under 35 U.S.C. 154(b) by 639 days.

(21) Appl. No.: 11/854,711

(22) Filed: Sep. 13, 2007

(65) Prior Publication Data
US 2008/0070889 A1 Mar. 20, 2008

Related U.S. Application Data

(60) Provisional application No. 60/845,076, filed on Sep. 15, 2006.

(51) Int. Cl.
C07D 471/10 (2006.01)
A61K 31/438 (2006.01)
A61P 3/06 (2006.01)
A61P 25/04 (2006.01)

(52) U.S. Cl. ............ 514/23; 514/210.05; 540/203; 536/29.2; 536/55

(58) Field of Classification Search .......... 540/203; 514/210.05
See application file for complete search history.

(56) References Cited

U.S. PATENT DOCUMENTS

| | | | |
|---|---|---|---|
| 4,692,515 A * | 9/1987 | Georgiev et al. ............ | 540/203 |
| 5,130,425 A * | 7/1992 | Malamas ................ | 540/203 |
| 5,624,920 A | 4/1997 | McKittrick et al. | |
| 5,633,246 A | 5/1997 | McKittrick et al. | |
| 5,648,484 A * | 7/1997 | Wu .................. | 540/203 |
| 5,656,624 A | 8/1997 | Vaccaro et al. | |
| 5,688,787 A | 11/1997 | Burnett et al. | |
| 5,698,548 A * | 12/1997 | Dugar et al. ............ | 514/210.02 |
| 5,756,470 A | 5/1998 | Yumibe et al. | |
| 5,767,115 A | 6/1998 | Rosenblum | |
| 5,846,966 A | 12/1998 | Rosenblum et al. | |
| 6,992,067 B2 | 1/2006 | Glombik et al. | |
| 7,045,515 B2 | 5/2006 | Tomiyama et al. | |
| 7,291,728 B2 * | 11/2007 | Marin et al. ............. | 540/203 |
| 7,297,788 B2 * | 11/2007 | Noheda Marin et al. ..... | 540/203 |
| 7,638,526 B2 * | 12/2009 | McKittrick et al. ........ | 514/278 |
| 2005/0096307 A1 | 5/2005 | Graziano | |
| 2005/0282858 A1 | 12/2005 | Yao et al. | |
| 2008/0070888 A1 * | 3/2008 | McKittrick et al. ..... | 514/210.02 |
| 2008/0070890 A1 * | 3/2008 | Burnett et al. .......... | 514/210.05 |
| 2008/0070892 A1 * | 3/2008 | Harris et al. ............. | 514/210.16 |
| 2008/0076750 A1 * | 3/2008 | Aslanian et al. ........ | 514/210.02 |
| 2008/0076751 A1 * | 3/2008 | Aslanian et al. ........ | 514/210.02 |

FOREIGN PATENT DOCUMENTS

| | | |
|---|---|---|
| EP | 0553682 | 8/1993 |
| WO | WO 94/17038 | 8/1994 |
| WO | WO 96/19450 | 6/1996 |
| WO | WO 99/00393 | 1/1999 |
| WO | WO 99/61424 | 12/1999 |
| WO | WO 02/066464 | 8/2002 |
| WO | WO 2004/005293 | 1/2004 |
| WO | WO 2004/110375 | 12/2004 |
| WO | WO 2005/000217 | 1/2005 |
| WO | WO 2005/040167 | 5/2005 |
| WO | WO 2005/116009 | 12/2005 |

OTHER PUBLICATIONS

Database WPI, Thomson Scientific, 1985-138995 & JP 60075457A, Osaka Soda Co. Ltd., Apr. 27, 1985, Abstract.
PCT International Search Report mailed Jun. 5, 2008 for counterpart PCT Application No. PCT/US2007/019934.
Cignarella et al., "Synthesis of a new series of 2,7-diazaspiro[3.5]nonan-1-ones and study fo their cholinergic properties", Eur J. Med Chem 29:115-120, (1994).
Clayden et al., "Cyclization of Lithiated Pyridine and Quinoline Carboxamides: Synthesis of Partially Saturated Pyrrolopyridines and Spirocyclic β-Lactams", Organic Letters 7 (17):3673-3676, 2005.
Alonso et al., "Spiro β-Lactams as β-Turn Mimetics, Design, Synthesis, and NMR Conformational Analysis", J. Org. Chem. 66(19):6333-6338, (2001).
Bittermann et al., "Chirospecific Synthesis of Spirocyclic β-Lactams and Their Characterization as Potent Type II β-Turn Inducing Peptide Mimetics", J. Org. Chem. 71:97-102, 2006.
Khasanov et al., "Novel Asymmetric Approach to Proline-Derived Spiro-β-Lactams", J. Org. Chem 69(17):5766-5769, 2004.
Macias et al., "Diastereoselective [2+2]-Cycloaddition Reactions of Unsymmetrical Cyclic ketenes with Imines: Synthesis of Modified Prolines and Theorectical Study of the Reaction Mechanism", J. Org. Chem. 69:7004-7012, (2004).
Macias et al., "Synthesis of Enantiopure Pyrrolidine-Derived Peptidomimetics and Oligo-β-peptides via Nucleophilic Ring-Opening of β-Lactams", J. Org. Chem. 71:7721-7730, (2004).
Overman et al., "A Convenient Synthesis of 4-Unsubstituted β-Lactams", J. Am, Chem. Soc. 107:1698-1701, (1985).
Database WPI, Thomson Scientific, 1985-138995 & JP 60075457A, Osaka Soda Co. Ltd., Apr. 27, 1985, Astract, 1985.

(Continued)

*Primary Examiner* — Mark L Berch
(74) *Attorney, Agent, or Firm* — Carol S. Quagliato; Catherine D. Fitch

(57) ABSTRACT

Disclosed are compounds of the formula

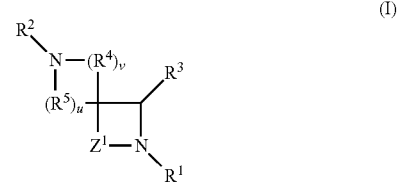

(I)

wherein $Z^1$ is —$CH_2$— or —$C(O)$—, $R^4$ and $R^5$ are carbon chains (and optionally, together can form a $C_2$ bridge), u and v are independently an integer of 0-3 such that there sum is from 3 to 5, and $R^2$ is heteroaryl, and $R^1$ and $R^3$ are as defined herein. Also disclosed are methods of treating pain, and methods of inhibiting the absorption of cholesterol using a compound of formula I.

23 Claims, No Drawings

OTHER PUBLICATIONS

PCT International Search Report dated Mar. 31, 2008 for PCT Application No. PCT/US2007/019930.
PCT International Search Report dated Feb. 25, 2008 for PCT Application No. PCT/US2007/019931.
PCT International Search Report dated Feb. 14, 2008 for PCT Application No. PCT/US2007/019871.
PCT International Search Report date Feb. 28, 2008 for PCT Application No. PCT/US2007/019901.
PCT International Search Report dated Dec. 12, 2008 for PCT Application No. PCT/US2007/019925.
PCT/International Search Report dated Feb. 25, 2008 for PCT Application No. PCT/US2007/019918.

* cited by examiner

AZETIDINE AND AZETIDONE DERIVATIVES USEFUL IN TREATING PAIN AND DISORDERS OF LIPID METABOLISM

REFERENCE TO RELATED APPLICATION

This Application claims the benefit of U.S. Provisional Application No. 60/845,076 filed Sep. 15, 2006.

BACKGROUND

Treatment of chronic pain, particularly inflammatory and neuropathic pain, is an area of high unmet medical need. Neuopathic pain is nerve injury resulting in hyperexcitability of neurons involved in pain sensation. T-currents are present in neurons of pain pathways. T-type calcium channel blockers are effective in preclinical models of neuropathic pain.

Niemann-Pick C1-like (NPC1L1) has been identified as a critical mediator of cholesterol absorption. It has been determined that the cholestrol absorption inhibitor ezetimibe targets NPC1L1.

The treatment of disorders of lipid metabolism, diabetes, vascular conditions, demyelination and nonalcoholic fatty liver disease with Spirocyclic Azetidinone Derivatives has been disclosed. Spirocyclic Azetidinone Derivatives that inhibit cholesterol absorption in the small intestine are well known in the art and are described, for example, in US RE 37,721; U.S. Pat. Nos. 5,631,356; 5,767,115; 5,846,966; 5,698,548; 5,633,246; 5,656,624; 5,624,920; 5,688,787; 5,756,470, US Publication No. 2002/0137689; WO 02/066464; WO 95/08522 and WO96/19450. Each of the aforementioned publications is incorporated by reference. The art indicates that these compounds are useful in treating, for example, atherosclerotic coronary disease, either by administrating these compounds alone or with a second compound such as a cholesterol biosynthesis inhibitor.

WO 2005/000217 describes combination therapies for the treatment of dyslipidemia comprising the administration of a combination of an anti-obesity agent and an anti-dyslipidemic agent. WO 2004/110375 describes combination therapies for the treatment of diabetes comprising the administration of a combination of an anti-obesity agent and an anti-diabetic agent. US 2004/0122033 describes combination therapies for the treatment of obesity comprising the administration of a combination of an appetite suppressant and/or metabolic rate enhancers and/or nutrient absorption inhibitors. US 2004/0229844 describes combination therapies for treating atherosclerosis comprising the administration of a combination of nicotinic acid or another nicotinic acid receptor agonist and a DP receptor antagonist. Also known is a method for treating nonalcoholic fatty liver disease in a mammal by administering an effective amount of therapeutic composition comprising at least one cholesterol lowering agent and/or at least one $H_3$ receptor antagonist/inverse agonist.

SUMMARY OF THE INVENTION

The present invention provides compounds of formula I:

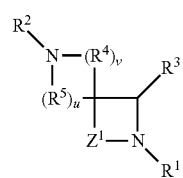

(I)

or a pharmaceutically acceptable salt, solvate, hydrate, ester, prodrug or stereoisomer thereof, wherein:

$Z^1$ is selected from the group consisting of: —$CH_2$— or —C(O)—

$R^1$ is -phenyl or -benzyl, wherein a phenyl group may be fused to a heteroaryl ring or a heterocycloalkyl ring, and wherein the phenyl group or phenyl ring of a benzyl group may be optionally and independently substituted with 1-5 groups selected from $R^9$, —OH, —$CF_3$, —$OCF_3$, —$CHF_2$, —$OCHF_2$, —SH, —$NH_2$, —$NO_2$, —C(O)OH, -halo, -alkoxy, -alkyl, -alkylthio, —$CH_2NHC(O)(CH_2)_{10}C(O)NHCH_2$—$(CH(OH))_4$—$CH_2OH$, hydroxyalkyl, methylenedioxy, ethylenedioxy, —CN, —NH(alkyl), —N(alkyl)$_2$, —$SO_2NH_2$, —$SO_2NH(alkyl)$, —$SO_2N(alkyl)_2$, —$SO_2$-alkyl, —$SO_2$-aryl, -acyl, -alkoxycarbonyl, —C(O)$NH_2$, —S(O)-alkyl, —NHC(O)-alkyl, —C(=NH)$NH_2$, -phenyl, -benzyl, —O-phenyl, —C≡C—$CH_2NR^{14}H^{24}$, —C≡C—$CH_2C(O)OR^{25}$, -alkylene-$NR^{14}R^{26}$, —O-benzyl, —$PO_3H_2$, —$SO_3H$, —$B(OH)_2$, a sugar, a polyol, a glucuronide or a sugar carbamate; or $R^1$ is —$(CH_2)_n$-phenyl, wherein the phenyl group may be fused to a heteroaryl ring or a heterocycloalkyl ring and wherein the phenyl group may be optionally and independently substituted with 1-5 groups selected from -$R^7$, $R^8$ or -$R^{11}$;

$R^2$ is selected from the group consisting of:
(1) heteroaryl (e.g., pyridyl, pyrimidinyl, benzoimidazolyl-, and substituted heteroaryl (e.g., heteroaryl substituted with one or more ring system substitutents as defined herein)),
(2) heterocycloalkenyl (e.g. dihydrothiazolyl, dihydrooxazolyl, and substituted heterocycloalkenyl (e.g., heterocycloalkenyl substituted with one or more ring system substitutents as defined herein));
(3) substituted cyclobutenedione of the formula:

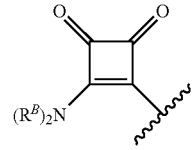

wherein each $R^B$ is independently selected from the group consisting of: H, alkyl (e.g., $C_1$ to $C_6$ alkyl, or $C_1$ to $C_4$ alkyl or $C_1$ to $C_2$ alkyl), substituted alkyl (e.g., $C_1$ to $C_6$ substituted alkyl, or $C_1$ to $C_4$ substituted alkyl or $C_1$ to $C_2$ substituted alkyl), aryl, substituted aryl, heteroaryl and substituted heteroaryl, provided that at least one $R^B$ is other than H, and
wherein the substituted alkyl moieties are each independently substituted with one or more (i.e., at least one, e.g., 1 to 3) substituents independently selected from the group consisting of: (a) —(C=N—O-alkyl)$CH_3$, (b) —NC(O)$NH_2$, (c) —NC(O)NH(alkyl), (d) —NC(O)N(alkyl)$_2$, (e) —$SO_2NH_2$, (f) —$SO_2NH(alkyl)$, (g) —$SO_2N(alkyl)_2$, (h) —$CF_3$, (i) —OH, (j) -halo, (k) —CN, (l) -alkoxy, (m) —C(O)O-alkyl, (n) —S(O)alkyl, (o) —$SO_2$-alkyl, and (p) —P(O)(O-alkyl)$_2$;
wherein the substituted aryl moieties are each independently substituted with one or more (i.e., at least one, e.g., 1 to 3) substituents independently selected from the group consisting of: (a) —(C=N—O-alkyl)$CH_3$, (b) —NC(O)$NH_2$, (c) —NC(O)NH(alkyl), (d) —NC(O)N(alkyl)$_2$, (e) —$SO_2NH_2$, (f) —$SO_2NH(alkyl)$, (g) —$SO_2N(alkyl)_2$, (h) —$CF_3$, (i) —OH, (j) -halo, (k) —CN, (l) -alkoxy, (m) —C(O)O-alkyl, (n) —S(O)alkyl, (o) —$SO_2$-alkyl, (p) —P(O)(O-alkyl)$_2$, and (q) alkyl; and wherein the substituted heteroaryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl;

(4) thiadiazoles of the formula:

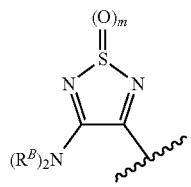

wherein each R$^B$ is independently selected from the group consisting of: H, alkyl (e.g., C$_1$ to C$_6$ alkyl, or C$_1$ to C$_4$ alkyl or C$_1$ to C$_2$ alkyl), substituted alkyl (e.g., C$_1$ to C$_6$ substituted alkyl, or C$_1$ to C$_4$ substituted alkyl or C$_1$ to C$_2$ substituted alkyl), aryl, substituted aryl, heteroaryl and substituted heteroaryl, provided that at least one R$^B$ is other than H, and m is 0, 1 or 2, and wherein the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$;

wherein the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and wherein the substituted heteroaryl moieties are each independently substituted with one or more (i.e., at least one, e.g., 1 to 3) substituents independently selected from the group consisting of: (a) —(C=N—O-alkyl)CH$_3$, (b) —NO(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and (5) substituted heteroaryl, said substituted heteroaryl substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl;

R$^3$ is -aryl or -heteroaryl, wherein an aryl group may be fused to a heteroaryl ring or a heterocycloalkyl ring and wherein the aryl group may be optionally and independently substituted with 1-5 groups selected from -halo, —OH, —OR$^{23}$, -alkyl, -alkoxy, —SH, -thioalkyl, —N(R$^{14}$)$_2$, —NO$_2$, —CN, —CF$_3$, —OC(O)R$^{14}$, —OC(O)—R$^{14}$, —C(O)OR$^{14}$, —C(O)O—R$^{14}$, R$^6$-aryl-, R$^7$, R$^8$, R$^9$ or R$^{10}$, and wherein a heteroaryl group may be optionally and independently substituted with one to five R$^6$ groups, such that R$^3$ is not -2-pyridyl, -3-pyridyl, unsubstituted phenyl, or 4-chloro-phenyl:

Each occurrence of R$^4$ is:

independently selected from the group consisting of: —CH$_2$—, —CH(alkyl)-, —C(alkyl)$_2$-, —C(O)—, —CH(substituted alkyl)-, —C(substituted alkyl)$_2$-, and each alkyl is independently selected, and each substituted alkyl is independently selected, and examples of said alkyl moieties include, for example, C$_1$ to C$_4$ alkyl and C$_1$ to C$_2$ alkyl, and examples of said substituted alkyl moieties include, for example, substituted C$_1$ to C$_4$ alkyl and substituted C$_1$ to C$_2$ alkyl, and preferably each occurrence of R$^4$ is selected from the group consisting of: —CH$_2$—, —CH(alkyl)-, —C(alkyl)$_2$, and —C(O)—, and more preferably, when v is 1, 2 or 3, there are 0 to 1 —C(O)— moieties, and preferably no —C(O)— moiety, and when said —C(O)— is present said —C(O)— moiety is preferably adjacent to the ring nitrogen, and wherein the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$;

Each occurrence of R$^5$ is:

independently selected from the group consisting of: —CH$_2$—, —CH(alkyl)-, —C(alkyl)$_2$-, —C(O)—, —CH(substituted alkyl)-, —C(substituted alkyl)$_2$-, and each alkyl is independently selected, and each substituted alkyl is independently selected, and examples of said alkyl moieties include, for example, C$_1$ to C$_4$ alkyl and C$_1$ to C$_2$ alkyl, and examples of said substituted alkyl moieties include, for example, substituted C$_1$ to C$_4$ alkyl and substituted C$_1$ to C$_2$ alkyl, and preferably each occurrence of R$^5$ is selected from the group consisting of: —CH$_2$—, —CH(alkyl)-, —C(alkyl)$_2$, and —C(O)—, and more preferably, when v is 1, 2 or 3, there are 0 to 1 —C(O)— moieties, and preferably no —C(O)— moiety, and when said —C(O)— is present said —C(O)— moiety is preferably adjacent to the ring nitrogen, and wherein the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$; or R$^4$ and R$^5$ are as defined above, and one ring carbon of R$^4$ and one ring carbon of R$^5$ are bound together by a -CH$_2$—OH$_2$— group (i.e., there is a C2 bridge joining a R$^4$ ring carbon and a R$^5$ ring carbon, and those skilled in the art will appreciate that the bridged carbons for $R^4$ and $R^5$ are each independently selected from the group consisting of: —CH—, —C(alkyl)-, and —C(substituted alkyl)- wherein alkyl and substituted alkyl are as defined in $R^4$ and $R^5$);

each occurrence of $R^6$ is independently -halo, —OH, -alkyl, -alkoxy, —SH, -alkylthio, —NH$_2$, —NO$_2$, hydroxyalkyl, methylenedioxy, ethylenedioxy, —SO$_2$NH$_2$, —SO$_2$NH(alkyl), —SO$_2$N(alkyl)$_2$, —SO$_2$-alkyl, —SO$_2$-aryl, acyl, —C(O)OH, —C(O)O-alkyl, —C(O)NH$_2$, —S(O)-alkyl, —NHC(O)-alkyl, —C(=NH)NH$_2$, —PO$_3$H$_2$, —SO$_3$H, —B(OH)$_2$, a sugar, a polyol, a glucuronide or a sugar carbamate;

$R^7$ is

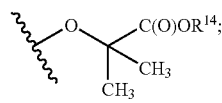

$R^8$ is:

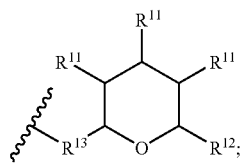

$R^9$ is

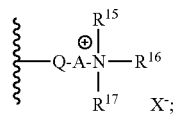

$R^{10}$ is

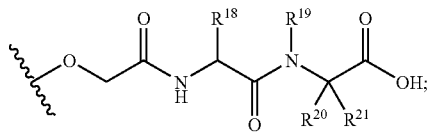

each occurrence of $R^{11}$ is independently —H, -halo, —OH, —OC(O)R$^{14}$, —OC(O)R$^{14}$ or —C(O)OR$^{14}$;

$R^{12}$ is —H, —OH, -alkylene-OH, -alkylene-OC(O)R$^{14}$, or —C(O)OR$^{14}$;

$R^{13}$ is absent, or $R^{13}$ is -alkylene-, -alkenylene-, -oxaalkylene-, —CH(OH)-alkylene-, -alkenylene-O-alkylene-;

each occurrence of $R^{14}$ is —H or alkyl;

$R^{15}$ and A, together with the N atom to which they are attached form a 5- to 7-membered heterocycloalkyl group that has one ring N atom; or $R^{15}$ and $R^{16}$, together with the N atom to which they are attached form a 5- to 7-membered heterocycloalkyl group that has one ring N atom;

$R^{16}$ is -alkyl, or $R^{16}$ and $R^{15}$, together with the N atom to which they are both attached, join to form a 5- to 7-membered heterocycloalkyl group that has one ring N atom;

$R^{17}$ is -alkyl, or $R^{17}$ and $R^{15}$, together with the N atom to which they are both attached, join to form a 5- to 7-membered heterocycloalkyl group that has one ring N atom; or $R^{17}$ and $R^{16}$, together with the N atom to which they are both attached, join to form a 5- to 7-membered heterocycloalkyl group that has one ring N atom;

$R^{18}$ is —H, -alkyl, -cycloalkyl or -aryl; wherein an alkyl group may be optionally substituted by one or more —OH, —N(R$^{14}$)$_2$, —NH(C=NH)NH$_2$, —C(O)N(R$^{14}$)$_2$, —C(O)OR$^{14}$, -alkoxy, -alkyl-C(O)N(R$^{14}$)$_2$, —S(O)$_n$-alkyl, -cycloalkyl or -aryl; and wherein an aryl group may be optionally and independently substituted by one or two substituents selected from -halo, —OH, -alkyl or -alkoxy;

$R^{19}$ is —H, -alkyl, or -arylalkyl, or $R^{19}$ and the nitrogen atom to which it is attached and $R^{20}$ and the carbon atom to which it is attached may join to form a heterocycloalkyl group that has one ring N atom and 3-6 carbon atoms, $R^{20}$ is —H, -alkyl, -cycloalkyl or -aryl; wherein an alkyl group may be optionally and independently substituted by one or more substituents selected from —OH, —N(R$^{14}$)$_2$, —NH—C(=NH)NH$_2$, —CN, —C(O)N(R$^{14}$)$_2$, —C(O)OR$^{14}$, -alkoxy, -arylalkoxy, —Si(alkyl)$_3$, —S(O)$_n$-alkyl, -cycloaklyl, -aryl or —S(O)$_n$-alkylaryl; wherein an aryl group may be optionally and independently substituted by one or two substituents selected from -halo, —OH, -alkyl or -alkoxy; or $R^{20}$ and $R^{21}$ together with the carbon atom to which they are attached, join to form a cycloalkyl group that has 3-7 ring carbon atoms;

$R^{21}$ is —H, -alkyl, -cycloalkyl or -aryl; wherein an alkyl group may be optionally and independently substituted by one or more substituents selected from —OH, —N(R$^{14}$)$_2$, —NH(C=NH)NH$_2$, —CN, —C(O)N(R$^{14}$)$_2$, —C(O)ORP$^{14}$, -alkoxy, -arylalkoxy, —Si(alkyl)$_3$, —S(O)$_n$-alkyl, -cycloaklyl, -aryl or —S(O)$_n$-alkylaryl; wherein an aryl group may be optionally and independently substituted by one or two substituents selected from -halo, —OH, -alkyl or -alkoxy;

$R^{23}$ is

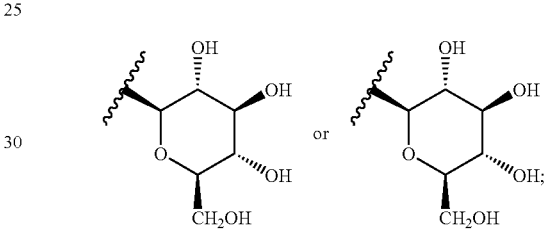

$R^{24}$ is —H, -alkyl, —C(O)-alkyl, —C(O)—N(R$^{14}$)$_2$, —S(O)$_2$-alkyl or S(O)$_2$-phenyl;

$R^{25}$ is —OH or —NR$^{14}$R$^{24}$;

$R^{26}$ is —C(O)-alkyl, —C(O)—N(R$^{14}$)$_2$, —S(O)$_2$-alkyl or S(O)$_2$-phenyl;

A is -alkylene-, -alkenylene-, -alkynylene-, -arylene-, -arylalkylene- or -oxaalkylene-, and when Q is absent, A may additionally be —C(O)— or —OC(O)—;

Q is absent, or Q is —O—, —S—, —NH—, —CH$_2$O—, —CH$_2$NH—, —C(O)—, —C(O)NH—, —NHC(O)—, —OC(O)—, —C(O)O—, —NHC(O)NH—, —OC(O)NH— or —NHC(O)O—;

X$^-$ is any anion (e.g., Cl or Br);

each occurrence of n is independently an integer ranging from 0 to 2;

u is an integer from 0 to 3; and v is an integer from 0 to 3, such that the sum of u and v is from 3 to 5.

One embodiment of this invention is directed to compounds of formula I having formula IA:

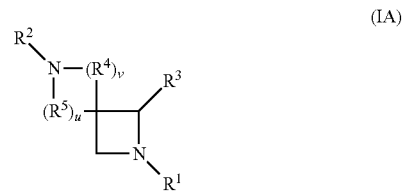

(i.e., Z$^1$ in formula I is —CH$_2$—) wherein all substituents are as defined for formula I.

Another embodiment of this invention is directed to compounds of formula I having the formula IB:

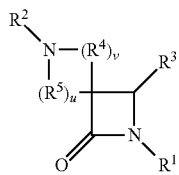

(i.e., $Z^1$ in formula I is —C(O)—) wherein all substituents are as defined for formula I.

Another embodiment of this invention is directed to compounds of formula I having formula IIA:

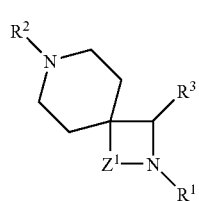

wherein $R^1$, $R^2$, $R^3$, and $Z^1$ are as defined for formula I.

Another embodiment of this invention is directed to compounds of formula I having formula IIA:

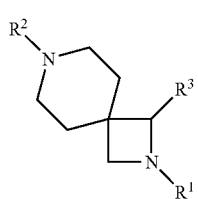

wherein $R^1$, $R^2$ and $R^3$ are as defined for formula I.

Another embodiment of this invention is directed to compounds of formula I having formula IIB:

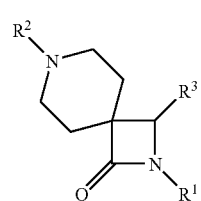

wherein $R^1$, $R^2$, and $R^3$ are as defined for formula I.

Another embodiment is directed to a pharmaceutically acceptable salt of the compound of formula I (e.g. a pharmaceutically acceptable salt of a compound of formula IA, IB, II, IIA or IIB).

Another embodiment of the invention is directed to a solvate of the compound of formula I (e.g. a solvate of a compound of formula IA, IB, II, IIA or IIB).

Another embodiment of the invention is directed to a compound of formula I (e.g., a compound of formula IA, IB, II, IIA or IIB) in pure and isolated form.

Another embodiment of the invention is directed to a compound of formula I (e.g., a compound of formula IA, IB, II, IIA or IIB) in in pure form.

Another embodiment of the invention is directed to a compound of formula I (e.g., a compound of formula IA, IB, II, IIA or IIB) in in isolated form.

Another embodiment of this invention is directed to a pharmaceutical composition comprising an effective amount of at least one (e.g., one) compound of formula I (e.g., at least one compound of formula IA, IB, II, IIA or IIB) and a pharmaceutically acceptable carrier.

Another embodiment of this invention is directed to a pharmaceutical composition comprising an effective amount of a compound of formula I (e.g., a compound of formula IA, IB, II, IIA or IIB) and a pharmaceutically acceptable carrier.

Another embodiment of this invention is directed to a pharmaceutical composition comprising an effective amount of at least one (e.g., one) compound of formula I (e.g., at least one compound of formula IA, IB, II, IIA, or IIB), an effective amount of at least one (e.g., one) other pharmaceutically active ingredient (i.e., agent) (e.g, at least one other agent for the treatment of pain, such as, inflammatory pain, chronic pain or neuropathic pain), and a pharmaceutically acceptable carrier.

The compounds of the present invention are T-type calcium channel blockers. The T-calcium channel blocker compounds of formula I (e.g., compounds of formulas IA, IB, II, IIA and IIB) are useful in the treatment of pain (such as, for example, inflammatory pain, chronic and neuropathic pain).

Thus, another embodiment of the present invention is directed to a method of treating pain (such as for example, inflammatory pain, chronic or neuropathic pain) comprising administering to a patient in need of such treatment an effective amount of at least one compound of formula I (e.g., at least one compound of formula IA, IB, II, IIA or IIB).

Another embodiment of the present invention is directed to a method of treating pain (such as, for example, inflammatory pain, chronic pain or neuropathic pain) comprising administering to a patient in need of such treatment an effective amount of a compound of formula I (e.g., a compound of formula IA, IB, II, IIA or IIB).

Another embodiment of the present invention is directed to a method of treating chronic pain comprising administering to a patient in need of such treatment an effective amount at least one (e.g., one) compound of formula I (e.g., at least one compound of formula IA, IB, II, IIA or IIB).

Another embodiment of the present invention is directed to a method of treating inflammatory pain comprising administering to a patient in need of such treatment an effective amount of at least one (e.g., one) compound of formula I (e.g., at least one compound of formula IA, IB, II, IIA or IB).

Another embodiment of the present invention is directed to a method of treating neuropathic pain comprising administering to a patient in need of such treatment an effective amount of at least one (e.g., one) compound of formula I (e.g., at least one compound of formula IA, IB, II, IIA or IIB).

Another embodiment of the present invention is directed to a method of treating neuropathic pain comprising administering to a patient in need of such treatment an effective amount of at least one (e.g., one) compound of formula I (e.g., at least one compound of formula IA, IB, II, IIA or IIB).

Another embodiment of the present invention is directed to a method of blocking T-calcium channels comprising administering to a patient in need of such treatment an effective amount of at least one (e.g., one) compound of formula I (e.g., at least one compound of formula IA, IB, II, IIA or IIB).

Another embodiment of the present invention is directed to a method of treating pain comprising administering to a patient in need of such treatment an effective amount of a combination of at least one compound of formula I (e.g., at least one compound of formula IA, IB, II, IIA or IIB) and at least one additional agent for treating pain.

Another embodiment of the present invention is directed to a method of treating chronic pain comprising administering to a patient in need of such treatment an effective amount of a combination of at least one compound of formula I (e.g., at least one compound of formula IA, IB, II, IIA or IIB) and at least one additional agent for treating chronic pain.

Another embodiment of the present invention is directed to a method of treating inflammatory pain comprising administering to a patient in need of such treatment an effective amount of a combination of at least one compound of formula I (e.g., at least one compound of formula IA, IB, II, IIA or IIB) and at least one additional agent for treating inflammatory pain.

Another embodiment of the present invention is directed to a method of treating neuropathic pain comprising administering to a patient in need of such treatment an effective amount of a combination of at least one compound of formula I (e.g., at least one compound of formula IA, IB, II, IIA or IIB) and at least one additional agent for treating inflammatory pain or neuropathic pain.

Another embodiment of the present invention is directed to a method of treating a disorder of lipid metabolism comprising administering to a patient in need of such treatment an effective amount of a combination of at least one compound of formula I (e.g., at least one compound of formula IA, IB, II, IIA or IIB).

Another embodiment of the present invention is directed to a method of inhibiting the absorption of cholesterol comprising administering to a patient in need of such treatment an effective amount of at least one compound of formula I (e.g., at least one compound of formula IA, IB, II, IIA or IIB).

Another embodiment of the present invention is directed to a method of inhibiting cholesterol absorption comprising administering to a patient in need of such treatment an effective amount of at least one NPC1L1 antagonist compound of formula I (e.g., at least one compound of formula IA, IB, II, IIA or IIB).

Another embodiment of the present invention is directed to a method of inhibiting the absorption of cholesterol comprising administering to a patient in need of such treatment an effective amount of at least one compound of formula I (e.g., at least one compound of formula IA, IB, II, IIA or IIB) in combination with an effective amount of at least one additional agent useful for treating a disorder of lipid metabolism (such as, at least one additional agent useful in lowering cholesterol).

Another embodiment of the present invention is directed to a method of inhibiting cholesterol absorption comprising administering to a patient in need of such treatment an effective amount of at least one NPC1L1 antagonist compound of formula I (e.g., at least one compound of formula IA, IB, II, IIA or IIB) in combination with an effective amount of at least one additional agent useful for treating a disorder of lipid metabolism (such as at least one additional agent useful in lowering cholesterol).

Another embodiment of the invention is directed to the inhibition of the absorption of cholesterol comprising administering to a patient in need of such treatment an effective amount of at least one compound of formula I (e.g., at least one compound of formula IA, IB, II, IIA or IIB) in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula I (e.g., at least one compound of formula IA, IB, II, IIA or IIB) in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula I (e.g., at least one compound of formula IA, IB, II, IIA or IIB) in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula I (e.g., at least one compound of formula IA, IB, II, IIA or IIB) in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula I (e.g., a compound of formula IA, IB, II, IIA, or IIB) in combination with an effective amount of at least one inhibitor of HMG-CoA reductase (e.g., statins, such as, for example, simvastatin, atorvastatin calcium, and rosuvastatin calcium), and in combination with an effective amount of at least one NPC1L1 antagonist (such as, for example, ezetimibe, such as the Zetia® brand of ezetimibe). An example of a medicament already comprising a combination of a HMG-CoA reductase and a NPC1L1 antagonist that can be used in this embodiment is the Vytorin® brand of the combination of ezetimibe and simvastatin.

Another embodiment of the present invention is directed to a kit comprising in a single package at least one compound of formula I (e.g., at least one compound of formula IA, IB, II, IIA or IIB) in a pharmaceutical composition, and at least one separate pharmaceutical composition comprising at least one additional therapeutic agent (such as, for example, at least one of the addition agents useful in the treatment of pain, or at least one additional agent useful in the treatment of lipid disorders (such as at least one additional agent useful in lowering cholesterol)).

DETAILED DESCRIPTION

Current chronic pain therapies provide only partial relief in responsive patients and are either not tolerated or ineffective in others. Chronic pain may arise as a consequence of tissue inflammation, viral infection (HIV, Herpes zoster) direct tissue injury or trauma, as a result of chemotherapy (e.g. taxol, vincristine), lesions of the central nervous system (e.g. stroke, MS) or as a consequence of diabetes. When chronic pain is associated with somatic or visceral tissue injury, symptoms usually include severe sensory disturbances characterized by spontaneous pain (often described as stabbing, burning, electric-shock-like or throbbing), hyperalgesia (exaggerated responsiveness to painful stimuli) and allodynia (perception of non noxious stimuli as painful). Prevalent symptoms in human patients include cold hyperalgesia, tactile allodynia and less commonly, heat hyperalgesia. Symptoms may present in isolation or in combination and there is often appreciable variation in the symptomatology associated with different disease states and typically between patients presenting with the same condition. In cases of somatic or visceral tissue injury/diseases, these distorted sensory perceptions have been linked to inappropriate activity (pathological hyperexcitability) in the peripheral nerves innervating the affected area. Neuronal hyperexcitability may arise as a result of altered ion channel function or activity.

Chronic pain is a true disease. It is believed to be a result, at least in part, of the plasticity at synapses in nociceptive processing centers, a phenomenon referred to as "central sensitization" which consists of increased excitability of spinal cord dorsal horn neurons. Maintenance of central sensitization is believed to require sustained peripheral neuronal activity (hyperexcitability) in sensory afferent nerves and such activity may be generated as a result of ectopic foci. Large T-type calcium currents can be found in sensory afferent neurons of the dorsal root ganglia (DRG). T-type calcium channels have been implicated as a causal factor in establishing such abnormal hyperexcitability, due to their known ability to function as neuronal pacemakers. Pharmacological and antisense oligonucleotide evidence supports a key role for DRG T-type calcium channels preclinical models of chronic pain.

T-type calcium channels are voltage-gated channels that can be opened with relatively small depolarizations from the resting potential of excitable cells. There are three distinct genes for T-type calcium currents that encode for $Ca_v3.1$, $Ca_v3.2$ and $Ca_v3.3$. The individual subtypes have unique patterns of distribution and are expressed in peripheral and central portions of pain pathways. T-type calcium channels are found in small and medium sized DRG neurons ($Ca_v3.2$) and regions of the CNS involved in pain processing including the dorsal horn of the spinal cord an the thalamus (Talley et al, *J Neurosci* 1999, 19:1895-1911). T-type calcium currents have been shown to play a role in neuronal burst firing via low-threshold calcium spikes that permit rapid burst of neuronal action potentials (Suzuki and Rogwoski, Proc Natl Acad Sci USA, 1989, 86:7228-7232; White et al., *Proc Natl Acad Sci USA*, 1989, 86:6802-6806).

Inhibition of T-type calcium channel function in vivo through either the use of pharmacological blockers or antisense oligonucleotide mediated knockdown strongly implicate T-type channels in normal and pathological pain processing. Mibefradil and/or ethosuximide are selective for T-type calcium channel and have been shown to be effective in a number of preclinical pain models including: acute thermal and mechanical pain, phase I and II of the formalin model, the rat spinal nerve ligation model, capsaicin-induced mechanical hyperalgesia, rat tail flick, paclitaxil- and vincristine-induced chemoneuropathy (Barton et al., *Eur J Pharmacol*, 2005, 521:79-8; Dogrul et al *Pain,* 2003, 105:159:168; Flatters and Bennett, *Pain,* 2004, 109:150-161; Todorovic et al., *Brain Res,* 2002, 951:336-340).

Pain relief in response to ethosuximide could be due to either central or peripheral actions. However efficacy in response to mibefradil can be attributed to peripheral effects for two reasons. First systemically administered mibefradil does not enter the brain. In addition intrathecal administration of mibefradil is ineffective (Dogrul et al *Pain,* 2003, 105:159: 168). Further evidence supporting efficacy from block of peripheral T-type channels comes from studies with antisense oligonucleotide directed against on type of T-type channel, $Ca_v3.2$. Intrathecal injection of hCaV3.2 specific oligonucleotides decreased T-type calcium currents in DRG neurons and produced antinociceptive, anti-hyperalgesic and anti-allodynic effects. In these studies the uptake of oligonucleotide and the antisense mediated knockdown of T-type currents occurred in DRG neurons close to the site of injection but not in spinal cord (Bourinet et al., *EMBO J,* 2005 24:315-324).

The compounds of formula I of this invention are T-type calcium channel blockers. Accordingly, the present compounds are useful in the treatment or prevention of conditions that are treatable or preventable by administering T-type calcium channel blockers. Such conditions include the treatment or prevention of neuropathic pain.

Neuropathic pain as used herein refers to an abnormal state of pain sensation, in which a reduction of pain threshold and the like are continued, due to functional abnormalities accompanying damage or degeneration of a nerve, plexus or perineural soft tissue, which is caused by wound (e.g., lacerations, contusions, nerve avulsion injuries, amputation of a limb), compression (carpal tunnel syndrome, trigeminal neuralgia, tumor activity), infection, cancer, ischemia and the like, or metabolic disorders such as diabetes mellitus and the like. Neuropathic pain includes pain caused by either central or peripheral nerve damage. It also includes the pain caused by either mononeuropathy or polyneuropathy. In some embodiments, the neuropathic pain is induced by diabetes.

Other examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, post-stroke pain, pain associated with Parkinson's disease, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, bursitis, pain associated with AIDS, pain associated with multiple sclerosis, pain due to spinal trauma and/or degeneration, burn pain, referred pain, enhanced memory of pain and neuronal mechanisms involved in coping with pain. Inflammatory pain may arise as a result of soft tissue injury including that involving the musculature (myositis) and viscera (colitis and inflammatory bowel disease, pancreatitis, cystitis, ileitis, Crohn's disease), nerves (neuritis, radiculopathies, radioculogangionitis), arthritic conditions (e.g. rheumatoid disease and related conditions such as ankylosing spondylitis), joint disease (including osteoarthritis). The compounds of the present invention are particularly useful for treating or preventing allodynia and hyperalgesia.

Additional agents for treating neuropathic pain include non-opioid analgesics, opioid analgesics, antimigraine agents, Cox-II inhibitors, antiemetics, β-adrenergic blockers, anticonvulsants, antidepressants, other $Ca^{2+}$-channel blockers, sodium channel blockers, anticancer agents, agents for treating or preventing UI, agents for treating hypertension, agents for treating or preventing angina pectoris, agents for treating atrial fibrillation, agents for treating insomnia, agents for treating renal failure, agents for treating Alzheimer's disease, agents for treating or preventing IBD, agents for treating or preventing IBS, agents for treating Parkinson's disease and parkinsonism, agents for treating anxiety, agents for treating epilepsy, agents for treating a stroke, agents for treating psychosis, agents for treating Huntington's chorea, agents for treating ALS, agents for treating vomiting, agents for treating dyskinesia, and agents for treating depression.

Preferred additional agents for treating neuropathic pain include those selected from the group consisting of: non-opioid analgesics and opioid analgesics.

Additional agents for treating inflammatory pain include corticosteroids, non-sterodial anti-inflammatory agents, COX-I and COX-II inhibitors, agents useful for treating inflammatory bowel disease and agents useful for treating rheumatoid arthritis.

Another embodiment of the present invention is directed to a method of treating pain (such as for example, inflammatory pain, chronic or neuropathic pain) comprising administering to a patient in need of such treatment an effective amount of at least one (e.g., one) compound of formula IA.

Another embodiment of the present invention is directed to a method of treating pain (such as for example, inflammatory pain, chronic or neuropathic pain) comprising administering to a patient in need of such treatment an effective amount of at least one (e.g., one) compound of formula IB.

Another embodiment of the present invention is directed to a method of treating pain (such as for example, inflammatory pain, chronic or neuropathic pain) comprising administering to a patient in need of such treatment an effective amount of at least one (e.g., one) compound of formula I.

Another embodiment of the present invention is directed to a method of treating pain (such as for example, inflammatory pain, chronic or neuropathic pain) comprising administering to a patient in need of such treatment an effective amount of at least one (e.g., one) compound of formula IIA.

Another embodiment of the present invention is directed to a method of treating pain (such as for example, inflammatory pain, chronic or neuropathic pain) comprising administering to a patient in need of such treatment an effective amount of at least one (e.g., one) compound of formula IIB.

Another embodiment of the present invention is directed to a method of treating inflammatory pain comprising administering to a patient in need of such treatment an effective amount of at least one (e.g., one) compound of formula IA.

Another embodiment of the present invention is directed to a method of treating inflammatory pain comprising administering to a patient in need of such treatment an effective amount of at least one (e.g., one) compound of formula IB.

Another embodiment of the present invention is directed to a method of treating inflammatory pain comprising administering to a patient in need of such treatment an effective amount of at least one (e.g., one) compound of formula II.

Another embodiment of the present invention is directed to a method of treating inflammatory pain comprising administering to a patient in need of such treatment an effective amount of at least one (e.g., one) compound of formula IIA.

Another embodiment of the present invention is directed to a method of treating inflammatory pain comprising administering to a patient in need of such treatment an effective amount of at least one (e.g., one) compound of formula IIB.

Another embodiment of the present invention is directed to a method of treating chronic comprising administering to a patient in need of such treatment an effective amount of at least one (e.g., one) compound of formula IA.

Another embodiment of the present invention is directed to a method of treating chronic comprising administering to a patient in need of such treatment an effective amount of at least one (e.g., one) compound of formula IB.

Another embodiment of the present invention is directed to a method of treating chronic comprising administering to a patient in need of such treatment an effective amount of at least one (e.g., one) compound of formula II.

Another embodiment of the present invention is directed to a method of treating chronic comprising administering to a patient in need of such treatment an effective amount of at least one (e.g., one) compound of formula IIA.

Another embodiment of the present invention is directed to a method of treating chronic comprising administering to a patient in need of such treatment an effective amount of at least one (e.g., one) compound of formula IIB.

Another embodiment of the present invention is directed to a method of treating neuropathic pain comprising administering to a patient in need of such treatment an effective amount of at least one (e.g., one) compound of formula IA.

Another embodiment of the present invention is directed to a method of treating neuropathic pain comprising administering to a patient in need of such treatment an effective amount of at least one (e.g., one) compound of formula IB.

Another embodiment of the present invention is directed to a method of treating neuropathic pain comprising administering to a patient in need of such treatment an effective amount of at least one (e.g., one) compound of formula II.

Another embodiment of the present invention is directed to a method of treating neuropathic pain comprising administering to a patient in need of such treatment an effective amount of at least one (e.g., one) compound of formula IIA.

Another embodiment of the present invention is directed to a method of treating neuropathic pain comprising administering to a patient in need of such treatment an effective amount of at least one (e.g., one) compound of formula IIB.

Another embodiment of the present invention is directed to a method of blocking T-calcium channels comprising administering to a patient in need of such treatment an effective amount of at least one (e.g., one) compound of formula IA.

Another embodiment of the present invention is directed to a method of blocking T-calcium channels comprising administering to a patient in need of such treatment an effective amount of at least one (e.g., one) compound of formula IB.

Another embodiment of the present invention is directed to a method of blocking T-calcium channels comprising administering to a patient in need of such treatment an effective amount of at least one (e.g., one) compound of formula II.

Another embodiment of the present invention is directed to a method of blocking T-calcium channels comprising administering to a patient in need of such treatment an effective amount of at least one (e.g., one) compound of formula IIA.

Another embodiment of the present invention is directed to a method of blocking T-calcium channels comprising administering to a patient in need of such treatment an effective amount of at least one (e.g., one) compound of formula IIB.

Another embodiment of the present invention is directed to a method of treating pain comprising administering to a patient in need of such treatment an effective amount of a combination of at least one compound of formula IA and at least one additional agent for treating pain. The compound of formula IA and the additional agent for treating pain are administered currently or sequentially.

Another embodiment of the present invention is directed to a method of treating pain comprising administering to a patient in need of such treatment an effective amount of a combination of at least one compound of formula IB and at least one additional agent for treating pain. The compound of formula IB and the additional agent for treating pain are administered currently or sequentially.

Another embodiment of the present invention is directed to a method of treating pain comprising administering to a patient in need of such treatment an effective amount of a combination of at least one compound of formula II and at least one additional agent for treating pain. The compound of formula II and the additional agent for treating pain are administered currently or sequentially.

Another embodiment of the present invention is directed to a method of treating pain comprising administering to a patient in need of such treatment an effective amount of a combination of at least one compound of formula IIA and at least one additional agent for treating pain. The compound of formula IIA and the additional agent for treating pain are administered currently or sequentially.

Another embodiment of the present invention is directed to a method of treating pain comprising administering to a patient in need of such treatment an effective amount of a combination of at least one compound of formula IIB and at least one additional agent for treating pain. The compound of formula IIB and the additional agent for treating pain are administered currently or sequentially.

Another embodiment of the present invention is directed to a method of treating inflammatory pain comprising administering to a patient in need of such treatment an effective amount of a combination of at least one compound of formula IA and at least one additional agent for treating inflammatory pain. The compound of formula IA and the additional agent for treating inflammatory pain are administered currently or sequentially.

Another embodiment of the present invention is directed to a method of treating inflammatory pain comprising administering to a patient in need of such treatment an effective amount of a combination of at least one compound of formula IB and at least one additional agent for treating inflammatory pain. The compound of formula IB and the additional agent for treating inflammatory pain are administered currently or sequentially.

Another embodiment of the present invention is directed to a method of treating inflammatory pain comprising administering to a patient in need of such treatment an effective amount of a combination of at least one compound of formula II and at least one additional agent for treating inflammatory pain. The compound of formula II and the additional agent for treating inflammatory pain are administered currently or sequentially.

Another embodiment of the present invention is directed to a method of treating inflammatory pain comprising administering to a patient in need of such treatment an effective amount of a combination of at least one compound of formula IIA and at least one additional agent for treating inflammatory pain. The compound of formula IIA and the additional agent for treating inflammatory pain are administered currently or sequentially.

Another embodiment of the present invention is directed to a method of treating inflammatory pain comprising administering to a patient in need of such treatment an effective amount of a combination of at least one compound of formula IIB and at least one additional agent for treating inflammatory pain. The compound of formula IIB and the additional agent for treating inflammatory pain are administered currently or sequentially.

Another embodiment of the present invention is directed to a method of treating chronic pain comprising administering to a patient in need of such treatment an effective amount of a combination of at least one compound of formula IA and at least one additional agent for treating chronic pain. The compound of formula IA and the additional agent for treating chronic pain are administered currently or sequentially.

Another embodiment of the present invention is directed to a method of treating chronic pain comprising administering to a patient in need of such treatment an effective amount of a combination of at least one compound of formula IB and at least one additional agent for treating chronic pain. The compound of formula IB and the additional agent for treating chronic pain are administered currently or sequentially.

Another embodiment of the present invention is directed to a method of treating chronic pain comprising administering to a patient in need of such treatment an effective amount of a combination of at least one compound of formula II and at least one additional agent for treating chronic pain. The compound of formula II and the additional agent for treating chronic pain are administered currently or sequentially.

Another embodiment of the present invention is directed to a method of treating chronic pain comprising administering to a patient in need of such treatment an effective amount of a combination of at least one compound of formula IIA and at least one additional agent for treating chronic pain. The compound of formula IIA and the additional agent for treating chronic pain are administered currently or sequentially.

Another embodiment of the present invention is directed to a method of treating chronic pain comprising administering to a patient in need of such treatment an effective amount of a combination of at least one compound of formula IIB and at least one additional agent for treating chronic pain. The compound of formula IIB and the additional agent for treating chronic pain are administered currently or sequentially.

Another embodiment of the present invention is directed to a method of treating neuropathic pain comprising administering to a patient in need of such treatment an effective amount of a combination of at least one compound of formula IA and at least one additional agent for treating neuropathic pain. The compound of formula IA and the additional agent for treating neuropathic pain are administered currently or sequentially.

Another embodiment of the present invention is directed to a method of treating neuropathic pain comprising administering to a patient in need of such treatment an effective amount of a combination of at least one compound of formula IB and at least one additional agent for treating neuropathic pain. The compound of formula IB and the additional agent for treating neuropathic pain are administered currently or sequentially.

Another embodiment of the present invention is directed to a method of treating neuropathic pain comprising administering to a patient in need of such treatment an effective amount of a combination of at least one compound of formula II and at least one additional agent for treating neuropathic pain. The compound of formula II and the additional agent for treating neuropathic pain are administered currently or sequentially.

Another embodiment of the present invention is directed to a method of treating neuropathic pain comprising administering to a patient in need of such treatment an effective amount of a combination of at least one compound of formula IIA and at least one additional agent for treating neuropathic pain. The compound of formula IIA and the additional agent for treating neuropathic pain are administered currently or sequentially.

Another embodiment of the present invention is directed to a method of treating neuropathic pain comprising administering to a patient in need of such treatment an effective amount of a combination of at least one compound of formula IIB and at least one additional agent for treating neuropathic pain. The compound of formula IIB and the additional agent for treating neuropathic pain are administered currently or sequentially.

The compounds of formula I (e.g., at least one compound of formula IA, IB, II, IIA or IIB) of this invention are NPC1L1 antagonists and are therefore useful for treating disorders of lipid metabolism, in particular for inhibiting absorption of cholesterol.

The compounds of this invention are useful for treating disorders of lipid metabolism. The compounds of this invention are NPC1L1 antagonists. In one embodiment, the compounds of this invention are therefore useful for treating disorders of lipid metabolism, in particular for inhibiting absorption of cholesterol. It is to be understood that when the compounds of this invention are administered for inhibiting the absorption of cholesterol in a patient, the inhibition may be partial or complete. Accordingly, in one embodiment, the absorption of cholesterol in a patient is partially inhibited. In another embodiment, the absorption of cholesterol in a patient is completely inhibited.

Methods of treating disorders of lipid metabolism include treating hyperlipidemia, hype rcholesterolaemia, hypertriglyceridaemia, sitosterolemia and arteriosclerotic symptoms; inhibiting absorption of cholesterol from the intestine; reducing blood plasma or serum concentrations of LDL cholesterol; reducing the concentrations of cholesterol and cholesterol ester in blood plasma or serum; reducing blood plasma or serum concentrations of C-reactive protein (CRP); reducing blood plasma or serum concentrations of triglycerides; reducing blood plasma or serum concentrations of apolipoprotein B; increasing blood plasma or serum concentrations of high density lipoprotein (HDL) cholesterol; increasing the fecal excretion of cholesterol; treating a clinical condition for which a cholesterol absorption inhibitor is indicated; reducing the incidence of cardiovascular disease-related events; reducing plasma or tissue concentration of at least one non-cholesterol sterol or 5α-stanol; treating or preventing vascular inflammation; preventing, treating or ameliorating symptoms of Alzheimer's Disease; regulating the production or level of at least one amyloid β peptide in the bloodstream and/or brain of a patient; regulating the amount of ApoE isoform 4 in the bloodstream and/or brain; preventing and/or treating obesity; and preventing or decreasing the incidence of xanthomas.

A method of treating a disorder of lipid metabolism comprises administering a cholesterol absorption inhibitor of formula I (e.g., at least one compound of formula IA, IB, II, IIA or IIB).

Additional agents for treating a disorder of lipid metabolism include inhibitors of cholesterol absorption (e.g., NPC1L1 antagonists, such as, for example, ezetimibe (such as the Zetia® brand of ezetimibe)), inhibitors of cholesterol biosynthesis, including, but not limited to HMG CoA reductase inhibitors (such as statins, such as, for example, simvastatin (such as the Zocor® brand of simvastatin), atorvastatin calcium (such as the Lipitor® brand of atorvastatin calcium), and rosuvastatin calcium (such as the Crestor® brand of rosuvastatin calcium)), inhibitors of cholesterol biosynthesis, cholesterol ester transfer protein (CETP) inhibitors (e.g., torcetrapib), bile acid sequesterants, a nicotinic acid receptor agonist such as nicotinic acid or a derivative thereof (e.g., Niacin (nicotinic acid), and the Niaspan® brand of niacin extended release tablets), peroxisome proliferator-activator receptor (PPAR) alpha agonists or activators, acylcoenzyme A:cholesterol acyltransferase (ACAT) inhibitors; obesity control medications, hypoglycemic agents, antioxidants, antihypertensive agents, ileal bile acid transport ("IBAT") inhibitors (or apical sodium co-dependent bile acid transport ("ASBT") inhibitors; probucol or derivatives thereof; low-density lipoprotein ("LDL") receptor activators; omega 3 fatty acids ("3-PUFA"); natural water soluble fibers; plant sterols, and plant stanols and/or fatty acid esters of plant stanols.

U.S. Provisional Application 60/752,710, filed Dec. 20, 2005, and U.S. Provisional Application 60/77048, filed Mar. 29, 2006, disclose the use of cholesterol absorption inhibitors.

Classes of cholesterol lowering agents useful in the present methods for treating disorders of lipid metabolism include the following non-limiting classes of agents: NCP1L1 inhibitors such as ezetimibe; HMG-CoA reductase inhibitors; bile acid sequestrants; PPAR agonists or activators; ileal bile acid transport ("IBAT") inhibitors (or apical sodium co-dependent bile acid transport ("ASBT") inhibitors; nicotinic acid (niacin) and/or nicotinic acid receptor agonists; acylCoA:cholesterol O-acyltransferase ("ACAT") inhibitors; cholesteryl ester transfer protein ("CETP") inhibitors; probucol or derivatives thereof; low-density lipoprotein ("LDL") receptor activators; omega 3 fatty acids ("3-PUFA"); natural water soluble fibers; plant sterols, plant stanols and/or fatty acid esters of plant stanols.

Non-limiting examples of suitable cholesterol biosynthesis inhibitors useful in the present methods include competitive inhibitors of HMG-CoA reductase, the rate-limiting step in cholesterol biosynthesis, squalene synthase inhibitors, squalene epoxidase inhibitors and mixtures thereof. Non-limiting examples of suitable HMG-CoA reductase inhibitors useful in the present methods include statins such as lovastatin, pravastatin, fluvastatin, simvastatin, atorvastatin, cerivastatin, CI-981, resuvastatin, rivastatin and pitavastatin, rosuvastatin; HMG-CoA reductase inhibitors, for example L-659, 699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bith iophen-5-yl) methoxy]benzene-methanamine hydrochloride) and other sterol biosynthesis inhibitors such as DMP-565. Preferred HMG-CoA reductase inhibitors include lovastatin, pravastatin and simvastatin. The most preferred HMG-CoA reductase inhibitor is simvastatin.

Generally, a total daily dosage of cholesterol biosynthesis inhibitor(s) can range from about 0.1 to about 160 mg per day. In one embodiment, the dosage is from about 0.2 to about 80 mg/day, administered in a single dose or in 2-3 divided doses.

Bile acid squestrants bind bile acids in the intestine, interrupting the enterohepatic circulation of bile acids and causing an increase in the faecal excretion of steroids.

Non-limiting examples of suitable bile acid sequestrants useful in the present methods include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorilionite clay, aluminum hydroxide and calcium carbonate antacids.

The activators or agonists of PPAR act as agonists for the peroxisome proliferator-activated receptors. Three subtypes of PPAR have been identified, and these are designated as peroxisome proliferator-activated receptor alpha (PPARα), peroxisome pro life rato r-activated receptor gamma (PPARγ) and peroxisome proliferator-activated receptor delta (PPARδ). It should be noted that PPARδ is also referred to in the literature as PPARβ and as NUC1, and each of these names refers to the same receptor.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans. See, e.g., WO 97/28149.

PPARα activator compounds are useful for, among other things, lowering triglycerides, moderately lowering LDL levels and increasing HDL levels. Useful examples of PPARα activators include fibrates.

Non-limiting examples of suitable fibric acid derivatives ("fibrates") useful in the present methods include clofibrate; gemfibrozil; ciprofibrate; bezafibrate; clinofibrate; binifibrate; lifibrol; fenofibrate and mixtures thereof. These compounds can be used in a variety of forms, including but not limited to acid form, salt form, racemates, enantiomers, zwitterions and tautomers.

Other examples of PPARα activators useful in the present methods include suitable fluorophenyl compounds as disclosed in U.S. Pat. No. 6,028,109 which is incorporated herein by reference; certain substituted phenylpropionic compounds as disclosed in WO 00/75103 which is incorporated herein by reference; and PPARα activator compounds as disclosed in WO 98/43081 which is incorporated herein by reference.

Non-limiting examples of suitable PPARγ activators useful in the present methods include derivatives of glitazones or thiazolidinediones, such as, troglitazone; rosiglitazone and pioglitazone. Other useful thiazolidinediones include ciglitazone, englitazone, darglitazone and BRL 49653 as disclosed in WO 98/05331 which is incorporated herein by reference; PPARγ activator compounds disclosed in WO 00/76488 which is incorporated herein by reference; and PPARY activator compounds disclosed in U.S. Pat. No. 5,994,554 which is incorporated herein by reference.

Other useful PPARγ activator compounds useful in the present methods include certain acetylphenols as disclosed in U.S. Pat. No. 5,859,051 which is incorporated herein by reference; certain quinoline phenyl compounds as disclosed in WO 99/20275 which is incorporated herein by reference; aryl compounds as disclosed by WO 99/38845 which is incorporated herein by reference; certain 1,4-disubstituted phenyl compounds as disclosed in WO 00/63161; certain aryl compounds as disclosed in WO 01/00579 which is incorporated herein by reference; benzoic acid compounds as disclosed in WO 01/12612 & WO 01/12187 which are incorporated herein by reference; and substituted 4-hydroxy-phenylalconic acid compounds as disclosed in WO 97/31907 which is incorporated herein by reference.

PPARδ compounds are useful for, among other things, lowering triglyceride levels or raising HDL levels. Non-limiting examples of PPARδ activators useful in the present methods include suitable thiazole and oxazole derivatives, such as C.A.S. Registry No. 317318-32-4, as disclosed in WO 01/00603 which is incorporated herein by reference), certain fluoro, chloro or this phenoxy phenylacetic acids as disclosed in WO 97/28149 which is incorporated herein by reference; suitable non-β-oxidizable fatty acid analogues as disclosed in U.S. Pat. No. 5,093,365 which is incorporated herein by reference; and PPARδ compounds as disclosed in WO 99/04815 which is incorporated herein by reference.

Moreover, compounds that have multiple functionality for activating various combinations of PPARα, PPARγ and PPARδ are also useful in the present methods. Non-limiting examples include certain substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPARα and/or PPARγ activator compounds. Other non-limiting examples of useful PPARα and/or PPARγ activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1 heptylureido)ethyl]phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is incorporated herein by reference; and dithiolane compounds as disclosed in WO 01/25225 and WO 01/25226 which are incorporated herein by reference.

Other useful PPAR activator compounds useful in the present methods include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference; ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

The peroxisome proliferator-activated receptor(s) activator(s) are administered in a therapeutically effective amount to treat the specified condition, for example in a daily dose preferably ranging from about 50 to about 3000 mg per day. In one embodiment, the daily dose is from about 50 to about 2000 mg per day, administered in a single dose or in 2-4 divided doses. The exact dose, however, is determined by the attending clinician and is dependent on such factors as the potency of the compound administered, the age, weight, condition and response of the patient.

In an alternative embodiment, the present invention includes the use of one or more IBAT inhibitors or ASBT inhibitors. The IBAT inhibitors can inhibit bile acid transport to reduce LDL cholesterol levels. Non-limiting examples of suitable IBAT inhibitors useful in the present methods include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

Generally, a total daily dosage of IBAT inhibitor(s) can range from about 0.01 to about 1000 mg/day. In one embodiment, the dosage is from about 0.1 to about 50 mg/day, administered in a single dose or in 2-4 divided doses.

In another alternative embodiment, the methods of the present invention can further comprise nicotinic acid (niacin) and/or nicotinic acid receptor ("NAR") agonists as lipid lowering agents.

As used herein, "nicotinic acid receptor agonist" means any compound comprising that will act as an agonist to the nicotinic acid receptor. Compounds include those that have a pyridine-3-carboxylate structure or a pyrazine-2-carboxylate structure, including acid forms, salts, esters, zwitterions and tautomers, where available. Examples of nicotinic acid receptor agonists useful in the present methods include nicertrol, nicofuranose and acipimox. Nicotinic acid and NAR agonists inhibit hepatic production of VLDL and its metabolite LDL and increases HDL and apo A-1 levels. An example of a suitable nicotinic acid product is NIASPAN® (niacin extended-release tablets) which are available from Kos Pharmaceuticals, Inc. (Cranbury, N.J.).

Generally, a total daily dosage of nicotinic acid can range from about 500 to about 10,000 mg/day. In one embodiment, the dosage is from about 1000 to about 8000 mg/day. In another embodiment, the dosage is from about 3000 to about 6000 mg/day, administered in a single dose or in divided doses. Generally, the total daily dosage of a NAR agonist can range from about 1 to about 100 mg/day.

In another alternative embodiment, the methods of the present invention can further comprise one or more ACAT inhibitors as lipid lowering agents. ACAT inhibitors reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors useful in the present methods include avasimibe, HL-004, lecimibide and CL-277082 (N-(2,4-difluorophenyl)-N-[[4-(2,2-dimethylpropyl)phenylj]methyl]-N-heptylurea). See P. Chang et al. "Current, New and Future Treatments in Dyslipidaemia and Atherosclerosis", *Drugs* 2000 July;60(1); 55-93, which is incorporated by reference herein.

Generally, a total daily dosage of ACAT inhibitor(s) can range from about 0.1 to about 1000 mg/day, administered in a single dose or in 2-4 divided doses.

In another alternative embodiment, the compositions used in the methods of the present invention can further comprise one or more Cholesteryl Ester Transfer Protein ("CETP") Inhibitors coadministered with or in combination with one of more Spirocyclic Azetidinone Compounds. CETP is responsible for the exchange or transfer of cholesteryl ester carrying HDL and triglycerides in VLDL.

Non-limiting examples of suitable CETP inhibitors useful in the present methods are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be co-administered with or in combination with the fibric acid derivative(s) and sterol absorption inhibitor(s) discussed above.

Generally, a total daily dosage of CETP inhibitor(s) can range from about 0.01 to about 1000 mg/day, and preferably about 0.5 to about 20 mg/kg body weight/day, administered in a single dose or in 2 or more divided doses.

In another alternative embodiment, the methods of the present invention can further comprise probucol or derivatives thereof (such as AGI-1067 and other derivatives disclosed in U.S. Pat. Nos. 6,121,319 and 6,147,250), which can reduce LDL and HDL levels, as cholesterol lowering agents.

Generally, a total daily dosage of probucol or derivatives thereof can range from about 10 to about 2000 mg/day. In one embodiment, the dosage is from about 500 to about 1500 mg/day, administered in a single dose or in 2-4 divided doses.

In another alternative embodiment, the methods of the present invention can further comprise one or more low-density lipoprotein (LDL) receptor activators, as lipid lowering agents. Non-limiting examples of suitable LDL-receptor activators useful in the present methods include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioser. Thromb.* 1993; 13:1005-12.

Generally, a total daily dosage of LDL receptor activator(s) can range from about 1 to about 1000 mg/day, administered in a single dose or in 2-4 divided doses.

In another alternative embodiment, the methods of the present invention can further comprise fish oil, which contains Omega 3 fatty acids (3-PUFA), which can reduce VLDL and triglyceride levels, as a lipid lowering agent. Generally, a total daily dosage of fish oil or Omega 3 fatty acids can range from about 1 to about 30 grams per day, administered in a single dose or in 2-4 divided doses.

In another alternative embodiment, the methods of the present invention can further comprise natural water-soluble fibers, such as psyllium, guar, oat and pectin, which can reduce cholesterol levels. Generally, a total daily dosage of natural water soluble fibers can range from about 0.1 to about 10 grams per day, administered in a single dose or in 2-4 divided doses.

In another alternative embodiment, methods of the present invention can further comprise plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day, administered in a single dose or in 2-4 divided doses.

Thus, another embodiment of the invention is directed to the inhibition of the absorption of cholesterol comprising administering to a patient in need of such treatment an effective amount of at least one compound of formula IA.

Another embodiment of the invention is directed to the inhibition of the absorption of cholesterol comprising administering to a patient in need of such treatment an effective amount of at least one compound of formula IB.

Another embodiment of the invention is directed to the inhibition of the absorption of cholesterol comprising administering to a patient in need of such treatment an effective amount of at least one compound of formula II.

Another embodiment of the invention is directed to the inhibition of the absorption of cholesterol comprising administering to a patient in need of such treatment an effective amount of at least one compound of formula IIA.

Another embodiment of the invention is directed to the inhibition of the absorption of cholesterol comprising administering to a patient in need of such treatment an effective amount of at least one compound of formula IIB.

Another embodiment of the invention is directed to the inhibition of the absorption of cholesterol comprising administering to a patient in need of such treatment an effective amount of at least one compound of formula IA in combination with an effective amount of at least one additional agent for treating a disorder of lipid metabolism.

Another embodiment of the invention is directed to the inhibition of the absorption of cholesterol comprising administering to a patient in need of such treatment an effective amount of at least one compound of formula IB in combination with an effective amount of at least one additional agent for treating a disorder of lipid metabolism.

Another embodiment of the invention is directed to the inhibition of the absorption of cholesterol comprising administering to a patient in need of such treatment an effective amount of at least one compound of formula II in combination with an effective amount of at least one additional agent for treating a disorder of lipid metabolism.

Another embodiment of the invention is directed to the inhibition of the absorption of cholesterol comprising administering to a patient in need of such treatment an effective amount of at least one compound of formula IIA in combination with an effective amount of at least one additional agent for treating a disorder of lipid metabolism.

Another embodiment of the invention is directed to the inhibition of the absorption of cholesterol comprising administering to a patient in need of such treatment an effective amount of at least one compound of formula IIB in combination with an effective amount of at least one additional agent for treating a disorder of lipid metabolism.

Another embodiment of the invention is directed to the inhibition of the absorption of cholesterol comprising administering to a patient in need of such treatment an effective amount of at least one compound of formula IA in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula IB in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula II in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula IIA in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula IIB in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula IA in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula IB in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula II in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula IIA in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula IIB in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula IA in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula IB in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula II in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula IIA in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula IIB in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula IA in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula IB in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula II in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula IIA in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula IIB in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula I (e.g., a compound of formula IA, IB, II, IIA, or IIB) in combination with an effective amount of at least one inhibitor of HMG-CoA reductase (e.g., statins, such as, for example, simvastatin, atorvastatin calcium, and rosuvastatin calcium), and in combination with an effective amount of at least one NPC1L1 antagonist (such as, for example, ezetimibe, such as the Zetia® brand of ezetimibe). An example of a medicament already comprising a combination of a HMG-CoA reductase and a NPC1L1 antagonist that can be used in this embodiment is the Vytorin® brand of the combination of ezetimibe and simvastatin.

Another embodiment of the invention is directed a pharmaceutically acceptable salt of the compound of formula IA.

Another embodiment of the invention is directed a pharmaceutically acceptable salt of the compound of formula IB.

Another embodiment is directed to a pharmaceutically acceptable salt of the compound of formula II.

Another embodiment of the invention is directed a pharmaceutically acceptable salt of the compound of formula IIA.

Another embodiment of the invention is directed a pharmaceutically acceptable salt of the compound of formula IIB.

Another embodiment of the invention is directed to a solvate of the compound of formula IA.

Another embodiment of the invention is directed to a solvate of the compound of formula IB.

Another embodiment of the invention is directed to a solvate of the compound of formula II.

Another embodiment of the invention is directed to a solvate of the compound of formula IIA.

Another embodiment of the invention is directed to a solvate of the compound of formula IIB.

Another embodiment of the invention is directed to a stereoisomer of the compound of formula IA.

Another embodiment of the invention is directed to a stereoisomer of the compound of formula IB.

Another embodiment of the invention is directed to a stereoisomer of the compound of formula II.

Another embodiment of the invention is directed to a stereoisomer of the compound of formula IIA.

Another embodiment of the invention is directed to a stereoisomer of the compound of formula IIB.

Another embodiment of the invention is directed to a compound of formula IA in pure and isolated form.

Another embodiment of the invention is directed to a compound of formula IA in pure form.

Another embodiment of the invention is directed to a compound of formula IA in isolated form.

Another embodiment of the invention is directed to a compound of formula IB in pure and isolated form.

Another embodiment of the invention is directed to a compound of formula IB in pure form.

Another embodiment of the invention is directed to a compound of formula IB in isolated form.

Another embodiment of the invention is directed to a compound of formula II in pure and isolated form.

Another embodiment of the invention is directed to a compound of formula II in pure form.

Another embodiment of the invention is directed to a compound of formula II in isolated form.

Another embodiment of the invention is directed to a compound of formula IIA in pure and isolated form.

Another embodiment of the invention is directed to a compound of formula IIA in pure form.

Another embodiment of the invention is directed to a compound of formula IIA in isolated form.

Another embodiment of the invention is directed to a compound of formula IIB in pure and isolated form.

Another embodiment of the invention is directed to a compound of formula IIB in pure form.

Another embodiment of the invention is directed to a compound of formula IIB in isolated form.

Another embodiment of this invention is directed to a pharmaceutical composition comprising an effective amount of at least one (e.g., one) compound of formula IA and a pharmaceutically acceptable carrier.

Another embodiment of this invention is directed to a pharmaceutical composition comprising an effective amount of a compound of formula IA and a pharmaceutically acceptable carrier.

Another embodiment of this invention is directed to a pharmaceutical composition comprising an effective amount of at least one (e.g., one) compound of formula IB and a pharmaceutically acceptable carrier.

Another embodiment of this invention is directed to a pharmaceutical composition comprising an effective amount of a compound of formula IB and a pharmaceutically acceptable carrier.

Another embodiment of this invention is directed to a pharmaceutical composition comprising an effective amount of at least one (e.g., one) compound of formula II and a pharmaceutically acceptable carrier.

Another embodiment of this invention is directed to a pharmaceutical composition comprising an effective amount of a compound of formula II and a pharmaceutically acceptable carrier.

Another embodiment of this invention is directed to a pharmaceutical composition comprising an effective amount of at least one (e.g., one) compound of formula IIA and a pharmaceutically acceptable carrier.

Another embodiment of this invention is directed to a pharmaceutical composition comprising an effective amount of a compound of formula IIA and a pharmaceutically acceptable carrier.

Another embodiment of this invention is directed to a pharmaceutical composition comprising an effective amount of at least one (e.g., one) compound of formula IIB and a pharmaceutically acceptable carrier.

Another embodiment of this invention is directed to a pharmaceutical composition comprising an effective amount of a compound of formula IIB and a pharmaceutically acceptable carrier.

Another embodiment of this invention is directed to a pharmaceutical composition comprising an effective amount of at least one (e.g, one) compound of formula IA, an effective amount of at least one (e.g., one) other agent for the treatment of pain, and a pharmaceutically acceptable carrier.

Another embodiment of this invention is directed to a pharmaceutical composition comprising an effective amount of at least one (e.g., one) compound of formula IA, an effective amount of at least one (e.g., one) other agent for the treatment of inflammatory pain, and a pharmaceutically acceptable carrier.

Another embodiment of this invention is directed to a pharmaceutical composition comprising an effective amount of at least one (e.g., one) compound of formula IA, an effective amount of at least one (e.g., one) other agent for the treatment of chronic pain, and a pharmaceutically acceptable carrier.

Another embodiment of this invention is directed to a pharmaceutical composition comprising an effective amount of at least one (e.g., one) compound of formula IA, an effective amount of at least one (e.g., one) other agent for the treatment of neuropathic pain, and a pharmaceutically acceptable carrier.

Another embodiment of this invention is directed to a pharmaceutical composition comprising an effective amount of at least one (e.g., one) compound of formula IB, an effective amount of at least one (e.g., one) other agent for the treatment of pain, and a pharmaceutically acceptable carrier.

Another embodiment of this invention is directed to a pharmaceutical composition comprising an effective amount of at least one (e.g., one) compound of formula IB, an effective amount of at least one (e.g., one) other agent for the treatment of inflammatory pain, and a pharmaceutically acceptable carrier.

Another embodiment of this invention is directed to a pharmaceutical composition comprising an effective amount of at least one (e.g., one) compound of formula IB, an effective amount of at least one (e.g., one) other agent for the treatment of chronic pain, and a pharmaceutically acceptable carrier.

Another embodiment of this invention is directed to a pharmaceutical composition comprising an effective amount of at least one (e.g., one) compound of formula IB, an effective amount of at least one (e.g., one) other agent for the treatment of neuropathic pain, and a pharmaceutically acceptable carrier.

Another embodiment of this invention is directed to a pharmaceutical composition comprising an effective amount of at least one (e.g., one) compound of formula II, an effective amount of at least one (e.g., one) other agent for the treatment of pain, and a pharmaceutically acceptable carrier.

Another embodiment of this invention is directed to a pharmaceutical composition comprising an effective amount of at least one (e.g., one) compound of formula II, an effective amount of at least one (e.g., one) other agent for the treatment of inflammatory pain, and a pharmaceutically acceptable carrier.

Another embodiment of this invention is directed to a pharmaceutical composition comprising an effective amount of at least one (e.g., one) compound of formula II, an effective amount of at least one (e.g., one) other agent for the treatment of chronic pain, and a pharmaceutically acceptable carrier.

Another embodiment of this invention is directed to a pharmaceutical composition comprising an effective amount of at least one (e.g., one) compound of formula II, an effective amount of at least one (e.g., one) other agent for the treatment of neuropathic pain, and a pharmaceutically acceptable carrier.

Another embodiment of this invention is directed to a pharmaceutical composition comprising an effective amount of at least one (e.g., one) compound of formula IIA, an effective amount of at least one (e.g., one) other agent for the treatment of pain, and a pharmaceutically acceptable carrier.

Another embodiment of this invention is directed to a pharmaceutical composition comprising an effective amount of at least one (e.g., one) compound of formula IIA, an effective amount of at least one (e.g., one) other agent for the treatment of inflammatory pain, and a pharmaceutically acceptable carrier.

Another embodiment of this invention is directed to a pharmaceutical composition comprising an effective amount of at least one (e.g., one) compound of formula IIA, an effective amount of at least one (e.g., one) other agent for the treatment of chronic pain, and a pharmaceutically acceptable carrier.

Another embodiment of this invention is directed to a pharmaceutical composition comprising an effective amount of at least one (e.g., one) compound of formula IIA, an effective amount of at least one (e.g., one) other agent for the treatment of neuropathic pain, and a pharmaceutically acceptable carrier.

Another embodiment of this invention is directed to a pharmaceutical composition comprising an effective amount of at least one (e.g., one) compound of formula IIB, an effective amount of at least one (e.g., one) other agent for the treatment of pain, and a pharmaceutically acceptable carrier.

Another embodiment of this invention is directed to a pharmaceutical composition comprising an effective amount of at least one (e.g., one) compound of formula IIB, an effective amount of at least one (e.g., one) other agent for the treatment of inflammatory pain, and a pharmaceutically acceptable carrier.

Another embodiment of this invention is directed to a pharmaceutical composition comprising an effective amount of at least one (e.g., one) compound of formula IIB, an effective amount of at least one (e.g., one) other agent for the treatment of chronic pain, and a pharmaceutically acceptable carrier.

Another embodiment of this invention is directed to a pharmaceutical composition comprising an effective amount of at least one (e.g., one) compound of formula IIB, an effective amount of at least one (e.g., one) other agent for the treatment of neuropathic pain, and a pharmaceutically acceptable carrier.

In one embodiment, $R^1$ is —H.

In another embodiment, $R^1$ is -aryl.

In another embodiment, $R^1$ is -phenyl.

In another embodiment, $R^1$ is -phenyl, which is substituted with -alkyl,

In another embodiment, $R^1$ is -phenyl, which is substituted with -halo.

In still another embodiment, $R^1$ is -4-fluorophenyl.

In yet another embodiment, $R^1$ is -phenyl, which is substituted with —$NO_2$.

In another embodiment, $R^1$ is -phenyl, which is substituted with —OH.

In a further embodiment, $R^1$ is -phenyl, which is substituted with —C(O)OH.

In another embodiment, $R^1$ is -phenyl, which is substituted with —O-alkyl.

In another embodiment, $R^1$ is -phenyl, which is substituted with —$CF_3$.

In one embodiment, $R^1$ is phenyl, which is fused to a heteroaryl ring.

In another embodiment, $R^1$ is phenyl, which is fused to a heterocycloalkyl ring.

In various embodiments, $R^1$ is benzofuranyl, indazolyl or benzthiazolyl.

In various embodiments, $R^1$ is benzofuranyl, indazolyl or benzthiazolyl, each of which is substituted with a —COOH or a —$CH_2COOH$ group.

In various embodiments, $R^1$ is

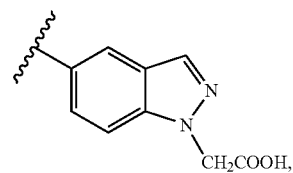

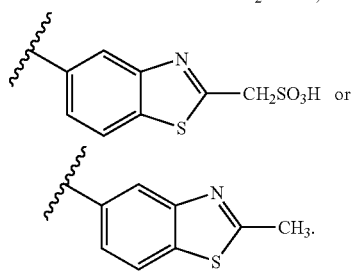

In one embodiment, $R^1$ is -heteroaryl.
In another embodiment, $R^1$ is -pyridyl.
In still another embodiment, $R^1$ is -2-pyridyl.
In one embodiment, $R^1$ is -benzyl.
In one embodiment, $R^1$ is:

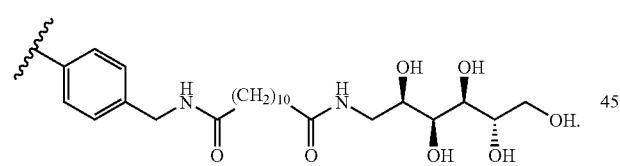

In one embodiment, $R^1$ is —$(CH_2)_n$-phenyl, wherein the phenyl group is substituted with

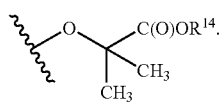

In various embodiments, $R^1$ is

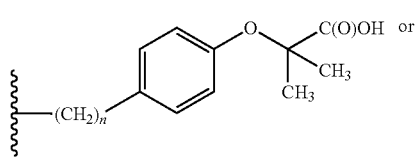

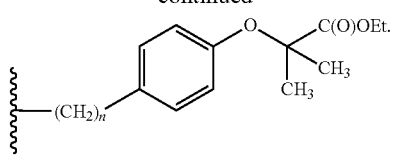

In one embodiment, $R^1$ is —$(CH_2)_n$-phenyl, wherein the phenyl group is substituted with

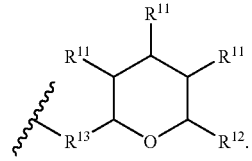

In another embodiment, $R^1$ is —$(CH_2)_n$-phenyl, wherein the phenyl group is substituted with

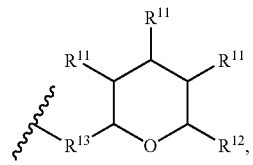

wherein $R^{13}$ is —absent, each occurrence of $R^{11}$ is —OH or —OAc, and $R^{12}$ is —$CH_2OH$ or —$CH_2OAc$.

In another embodiment, $R^1$ is —$(CH_2)_n$-phenyl, wherein the phenyl group is substituted with

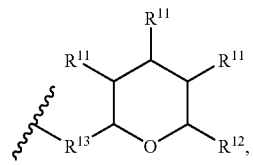

wherein $R^{13}$ is -alkylene-, -oxaalkylene- or -alkenylene-, each occurrence of $R^{11}$ is —OH or —OAc, and $R^{12}$ is —$CH_2OH$ or —$CH_2OAc$.

In various embodiments, $R^1$ is

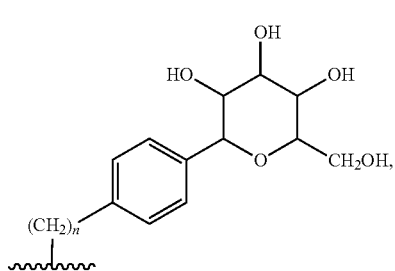

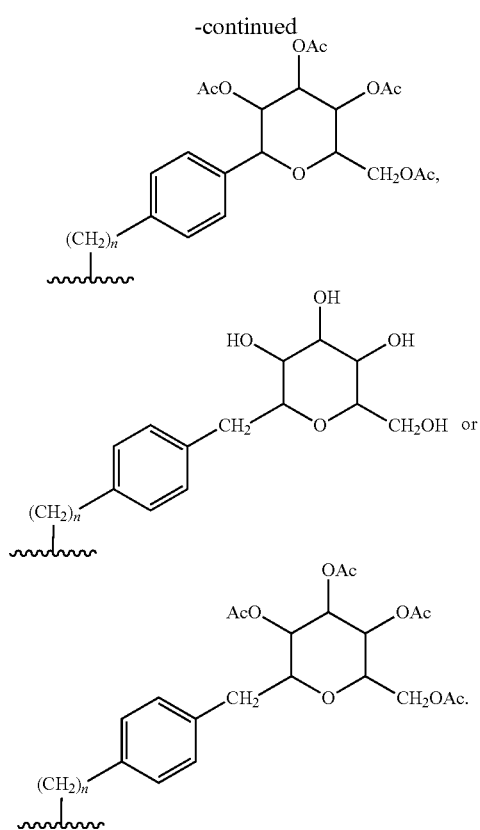

In still another embodiment, R¹ is-phenyl, which is substituted with

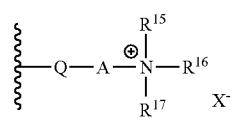

In various embodiments, R¹ is

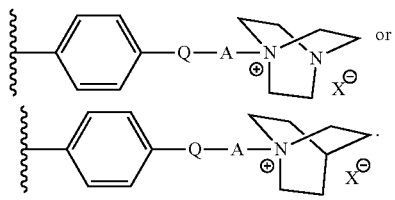

In another embodiment, R¹ is

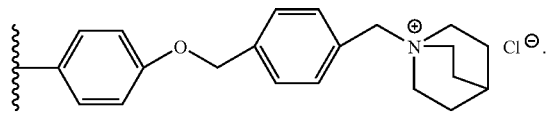

In one embodiment, R¹ is phenyl which is substituted with —C≡C—CH$_2$NR$^{14}$R$^{24}$, —C≡C—CH$_2$C(O)OR$^{25}$ or -alkylene-NR$^{14}$R$^{26}$.

In another embodiment, R¹ is —OR$^{23}$.

Another embodiment of this invention is directed to compounds of formula I wherein R² is heteroaryl selected from the group consisting of: pyrrolyl, thienyl, furanyl, thiazolyl, oxazolyl, imidazolyl, oxadiazolyl, triazolyl, tetrazolyl, triazinyl, pyridyl (o-, m-, or p-pyridyl), pyrimidinylt and pyrazinyl.

Another embodiment of this invention is directed to compounds of formula I wherein R² is heteroaryl wherein said heteroaryl is a benzofused heteroaryl (i.e., a phenyl ring fused to a heteroaryl ring, such as, for example, benzoimidazolyl-, quinazolinyl, isoquinolinyl, and quinolinyl).

Another embodiment of this invention is directed to compounds of formula I wherein, is substituted heteroaryl selected from the group consisting of: substituted pyrrolyl, substituted thienyl, substituted furanyl, substituted thiazolyl, substituted oxazolyl, substituted imidazolyl, substituted oxadiazolyl, substituted triazolyl, substituted tetrazolyl, substituted triazinyl, substituted pyridyl (o-, m-, or p-substituted pyridyl), substituted pyrimidinyl, substituted pyrazinyl, substituted benzofused heteroaryl (i.e., a phenyl ring fused to a heteroaryl ring wherein the phenyl ring is substituted or the heteroaryl ring is substituted or both the phenyl ring and the heteroaryl ring are substituted) such as, for example, substituted benzoimidazolyl-, substituted quinazolinyl, substituted isoquinolinyl, and substituted quinolinyl), wherein said R² substituted heteroaryl is substituted with 1 to 3 (or 1 to 2, or 1) substituents independently selected from the group consisting of: alkyl (e.g., C$_1$ to C$_4$ alkyl, such as, for example, methyl), halo (e.g., Cl, F, and Br, and in another example, F), CN, —CF$_3$, alkoxy (e.g., (C$_1$-C$_4$)alkoxy, such as, for example, —OCH$_3$), halo substituted alkoxy (e.g., halo substituted (C$_1$-C$_4$)alkoxy, such as, for example, —OCF$_3$), cycloalkyl (e.g., C$_3$ to C$_6$ cycloalkyl, such as, for example, cyclopropyl), and halo substituted alkyl (e.g., halo substituted C$_1$-C$_4$alkyl, such as, for example, —CF$_2$CH$_3$).

Another embodiment of this invention is directed to compounds of formula I wherein R² is selected from the group consisting of:

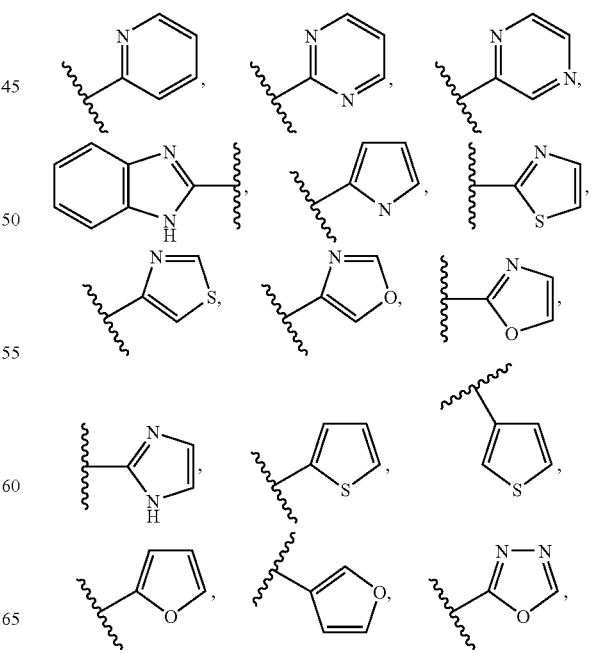

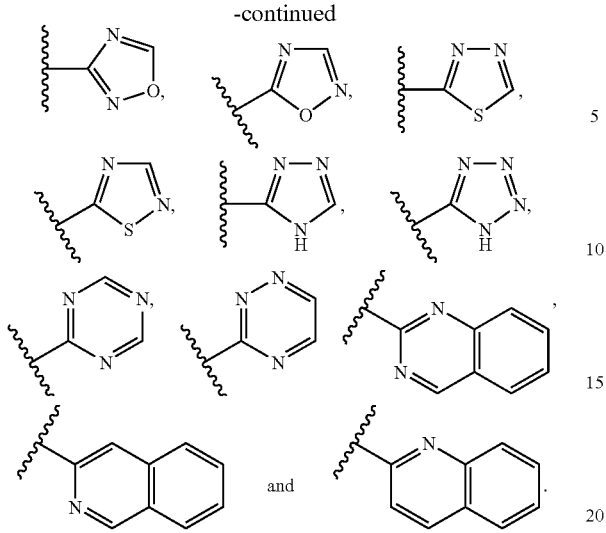
Another embodiment of this invention is directed to compounds of formula I wherein $R^2$ is selected from the group consisting of:
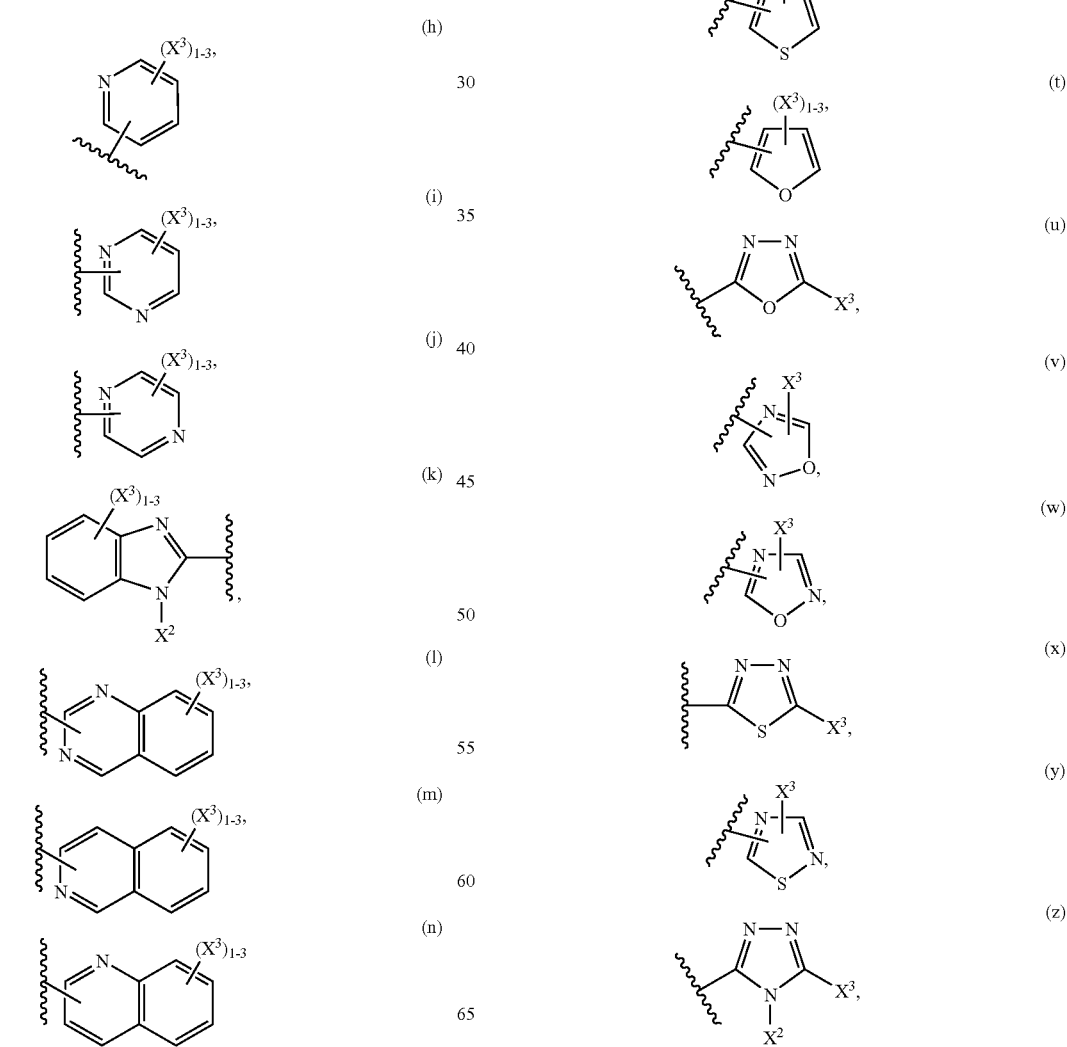

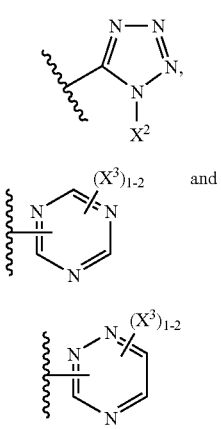

(aa)

(ab) and (ac)

wherein each $X^3$ is independently selected from the group consisting of: alkyl (e.g., $C_1$ to $C_4$ alkyl, such as, for example, methyl), halo (e.g., Cl, F, and Br, and in another example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein $X^2$ is as defined the same as for the $R^2$ groups.

Another embodiment of this invention is directed to compounds of formula I wherein $R^2$ is selected from the group consisting of:

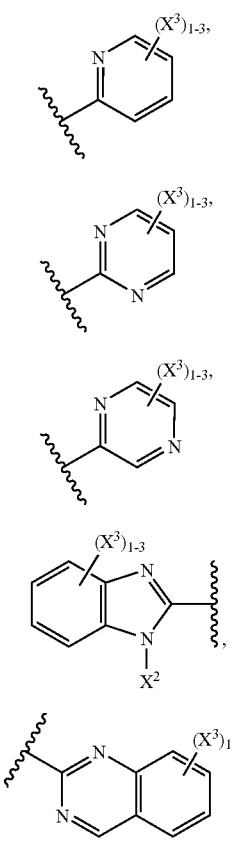

(h1)

(i1)

(j1)

(k)

(l1)

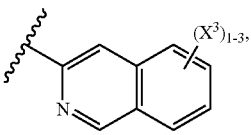
(m1)

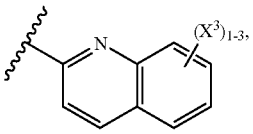
(n1)

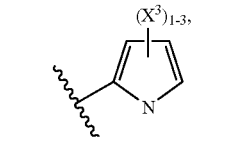
(o1)

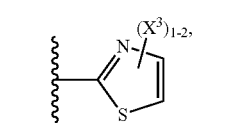
(p1)

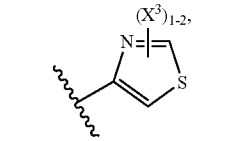
(p2)

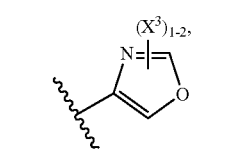
(q1)

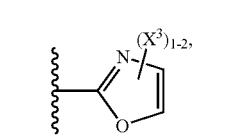
(q2)

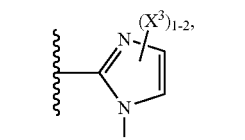
(r1)

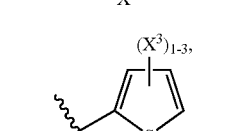
(s1)

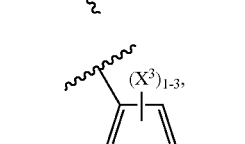
(s2)

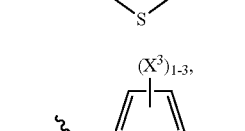
(t1)

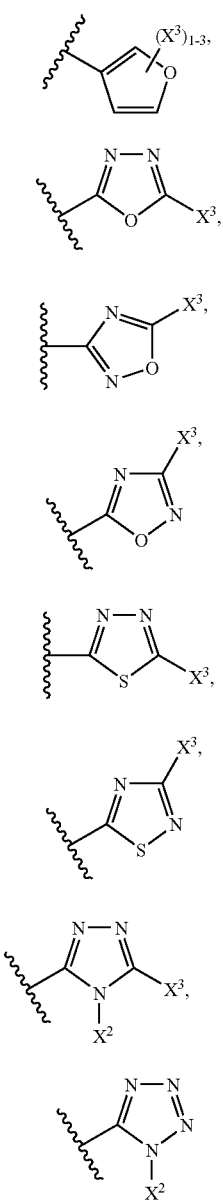

(t2)
(u)
(u1)
(u2)
(x)
(x1)
(z) and
(aa)

wherein $X^3$ and $X^2$ are as previously defined.

Another embodiment of this invention is directed to compounds of formula I wherein $R^2$ is selected from the group consisting of: monocyclic heteroaryl rings such as, for example, pyridyl (o-, m-, or p-pyridyl), pyrimidinyl, and pyrazinyl, and benzofused heteroaryl rings (i.e., a phenyl ring fused to a heteroaryl ring, such as, for example, benzoimidazolyl-, quinazolinyl, isoquinolinyl, and quinolinyl), examples of said heteroaryl moiety include, for example:

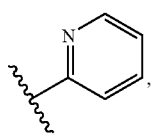 , 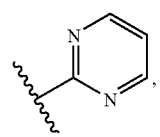 , 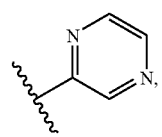 ,

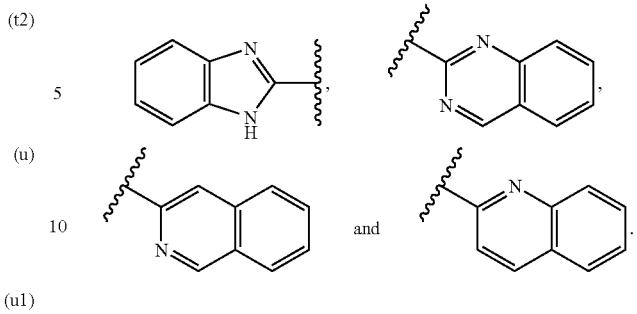

and

Another embodiment of this invention is directed to compounds of formula I wherein $R^2$ is substituted heteroaryl (such as, for example, substituted monocyclic heteroaryl rings, such as, for example, substituted pyridyl (e.g., o-, m-, or p-pyridyl), substituted pyrimidinyl and substituted pyrazinyl, and substituted benzofused heteroaryl rings (i.e., a phenyl ring fused to a heteroaryl ring, wherein either the phenyl ring or the heteroaryl ring is substituted, or both the phenyl ring and the heteroaryl ring are substituted, such as, for example, substituted pyridyl (substituted o-, m-, or p-pyridyl), substituted pyrimidinyl, substituted pyrazinyl, substituted quinazolinyl, substituted isoquinolinyl, and substituted quinolinyl), wherein said $R^2$ substituted heteroaryl is substituted with 1 to 3 (or 1 to 2, or 1) substituents independently selected from the group consisting of: alkyl (e.g., $C_1$ to $C_4$ alkyl, such as, for example, methyl), halo (e.g., Cl, F, and Br, and in another example, F), CN, —$CF_3$, alkoxy (e.g., ($C_1$-$C_4$) alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$).

Another embodiment of this invention is directed to compounds of formula I wherein $R^2$ is selected from the group consisting of:

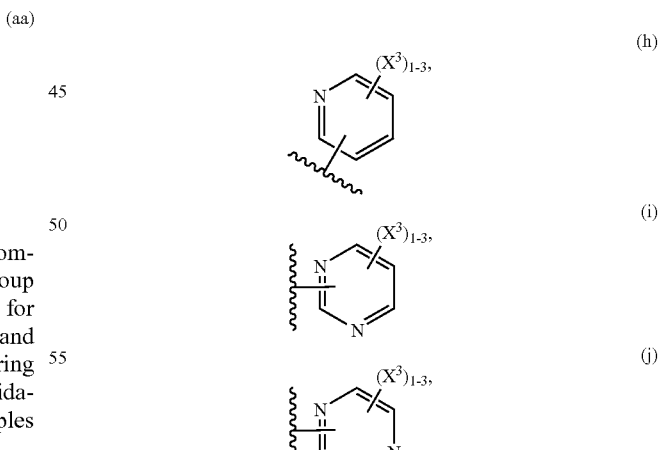

(h)
(i)
(j)
(k)

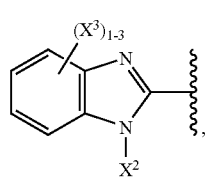

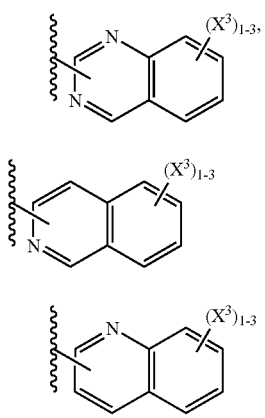

wherein there are preferably 1 or 2 independently selected $X^3$ substitutents and more preferably 1 $X^3$ substituent, and wherein each $X^3$ substituent is independently selected from the group consisting of: alkyl (e.g., $C_1$ to C4 alkyl, such as, for example, methyl), halo (e.g., Cl, F, and Br, and in another example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein $X^2$ in the benzoimidazolyl-moiety (k) is as previously defined, that is, $X^2$ is selected from the group consisting of: H and alkyl (e.g., $C_1$ to $C_4$ alkyl, such as, for example, methyl).

Another embodiment of this invention is directed to compounds of formula I wherein $R^2$ is selected from the group consisting of:

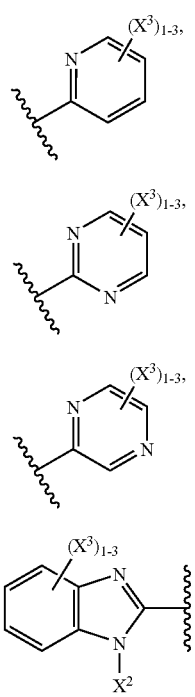

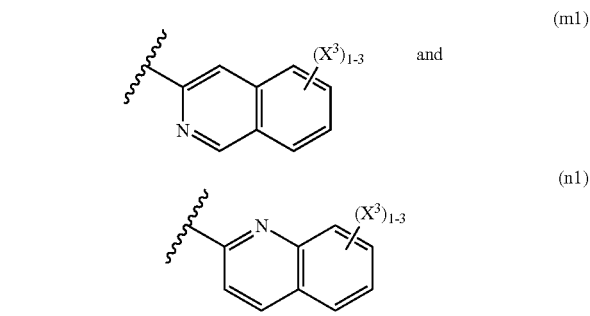

wherein $X^3$ and $X^2$ are as previously described.

Another embodiment of this invention is directed to compounds of formula I wherein $R^2$ is selected from the group consisting of:

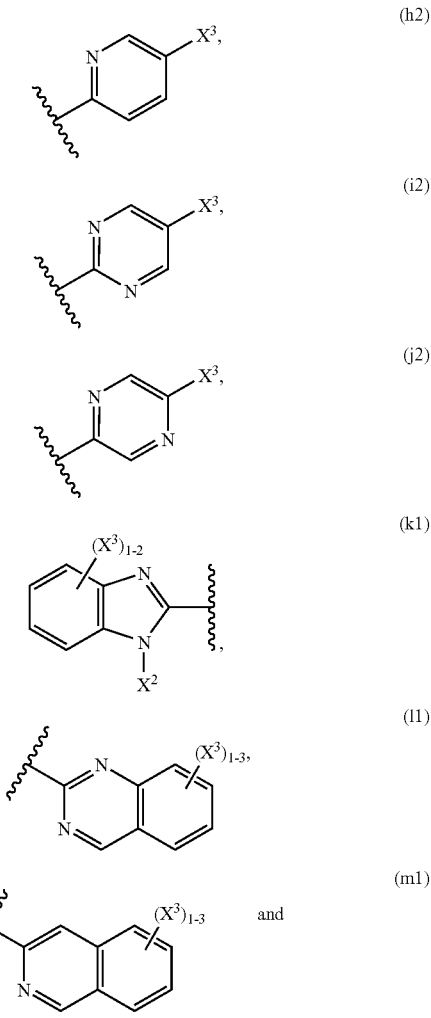

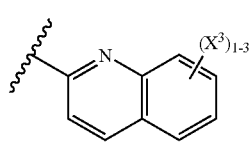
(n1)

wherein X³ and X² are as previously described.

Another embodiment of this invention is directed to compounds of formula I wherein the k1 moiety for R² is:

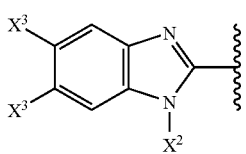
(k2)

wherein X³ and X² are as previously described (i.e., each X³ is independently selected), and wherein examples of said k2 moiety include, for example,

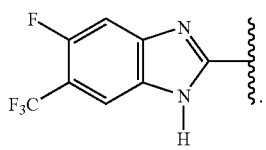
(k3)

Another embodiment of this invention is directed to compounds of formula I wherein R² is selected from the group consisting of: moieties (h), (i), (j), (k), (l), (m), (n), (h1), (i1), (j1), (k1), (l1), (m1), (n1), (h2), (i2), (j2), and (k2) wherein each X³ is independently selected from the group consisting of: Cl, F, —CF₃, —OCH₃, and —CN, and X² is selected from the group consisting of: H and —CH₃.

Another embodiment of this invention is directed to compounds of formula I wherein R² is selected from the group consisting of the moieties (h2), (i2), (j2), (k2), (l1), (m1) and (n1) wherein each X³ is independently selected from the group consisting of: Cl, F, Br, —CF₃, —OCH₃, cyclopropyl, —OCF₃, —CF₂CH₃ and —CN, and X² is selected from the group consisting of: H and —CH₃.

Another embodiment of this invention is directed to compounds of formula I wherein R² is substituted cyclobutenedione of the formula:

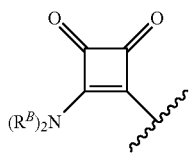

wherein each R$^B$ is independently selected from the group consisting of: H, alkyl (e.g., C₁ to C₆ alkyl, or C₁ to C₄ alkyl or C₁ to C₂ alkyl), substituted alkyl (e.g., C₁ to C₆ substituted alkyl, or C₁ to C₄ substituted alkyl or C₁ to C₂ substituted alkyl), aryl, substituted aryl, heteroaryl and substituted heteroaryl, provided that at least one R$^B$ is other than H, and
wherein the substituted alkyl moieties are each independently substituted with one or more (i.e., at least one, e.g., 1 to 3) substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o), —SO₂-alkyl, and (p) —P(O)(O-alkyl)₂;
wherein the substituted aryl moieties are each independently substituted with one or more (i.e., at least one, e.g., 1 to 3) substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl; and
wherein the substituted heteroaryl moieties are each independently substituted with one or more (i.e., at least one, e.g., 1 to 3) substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl Another embodiment of this invention is directed to compounds of formula II wherein R² is the above described substituted cyclobutenedione.

Another embodiment of this invention is directed to compounds of formula IIA wherein R² is the above described substituted cyclobutenedione.

Another embodiment of this invention is directed to compounds of formula IIB wherein R² is the above described substituted cyclobutenedione.

Another embodiment of this invention is directed to compounds of formula I wherein R² is a thiadiazole of the formula:

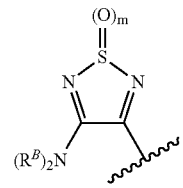

wherein each R$^B$ is independently selected from the group consisting of: H, alkyl (e.g., C₁ to C₆ alkyl, or C₁ to C₄ alkyl or C₁ to C₂ alkyl), substituted alkyl (e.g., C₁ to C₆ substituted alkyl, or C₁ to C₄ substituted alkyl or C₁ to C₂ substituted alkyl), aryl, substituted aryl, heteroaryl and substituted heteroaryl, provided that at least one R$^B$ is other than H, and m is 0, 1 or 2, and
wherein the substituted alkyl moieties are each independently substituted with one or more (i.e., at least one, e.g., 1 to 3) substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (l) -halo, (k) —CN, (7) -alkoxy, (m) —C(O)O-alkyl, (n) —S(O)alkyl, (o) —SO₂-alkyl, and (p) —P(O)(O-alkyl)₂;
wherein the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and wherein the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl.

Another embodiment of this invention is directed to compounds of formula II wherein R$^2$ is the above described thiadiazole.

Another embodiment of this invention is directed to compounds of formula IIA wherein R$^2$ is the above described thiadiazole.

Another embodiment of this invention is directed to compounds of formula IIB wherein R$^2$ is the above described thiadiazole.

Another embodiment of this invention is directed to the compounds of formula I wherein R$^2$ is the above identified thiadiazole wherein m is 0.

Another embodiment of this invention is directed to the compounds of formula II wherein R$^2$ is the above identified thiadiazole wherein m is 0.

Another embodiment of this invention is directed to the compounds of formula IIA wherein R$^2$ is the above identified thiadiazole wherein m is 0.

Another embodiment of this invention is directed to the compounds of formula IIB wherein R$^2$ is the above identified thiadiazole wherein m is 0.

Another embodiment of this invention is directed to the compounds of formula I wherein R$^2$ is the above identified thiadiazole wherein m is 1.

Another embodiment of this invention is directed to the compounds of formula II wherein R$^2$ is the above identified thiadiazole wherein m is 1.

Another embodiment of this invention is directed to the compounds of formula IIA wherein R$^2$ is the above identified thiadiazole wherein m is 1.

Another embodiment of this invention is directed to the compounds of formula IIB wherein R$^2$ is the above identified thiadiazole wherein m is 1.

Another embodiment of this invention is directed to the compounds of formula I wherein R$^2$ is the above identified thiadiazole wherein m is 2.

Another embodiment of this invention is directed to the compounds of formula II wherein R$^2$ is the above identified thiadiazole wherein m is 2.

Another embodiment of this invention is directed to the compounds of formula IIA wherein R$^2$ is the above identified thiadiazole wherein m is 2.

Another embodiment of this invention is directed to the compounds of formula IIB wherein R$^2$ is the above identified thiadiazole wherein m is 2.

Another embodiment of this invention is directed to compounds of formula I wherein R$^2$ is selected from the group consisting of:

(A) heteroaryl, such as, for example, monocyclic heteroaryl rings such as, for example, pyridyl (o-, m-, or p-pyridyl), pyrimidinyl, and pyrazinyl, and benzofused heteroaryl rings (i.e., a phenyl ring fused to a heteroaryl ring, such as, for example, benzoimidazolyi-, quinazolinyl, isoquinolinyl, and quinolinyl), examples of said heteroaryl moiety include, for example:

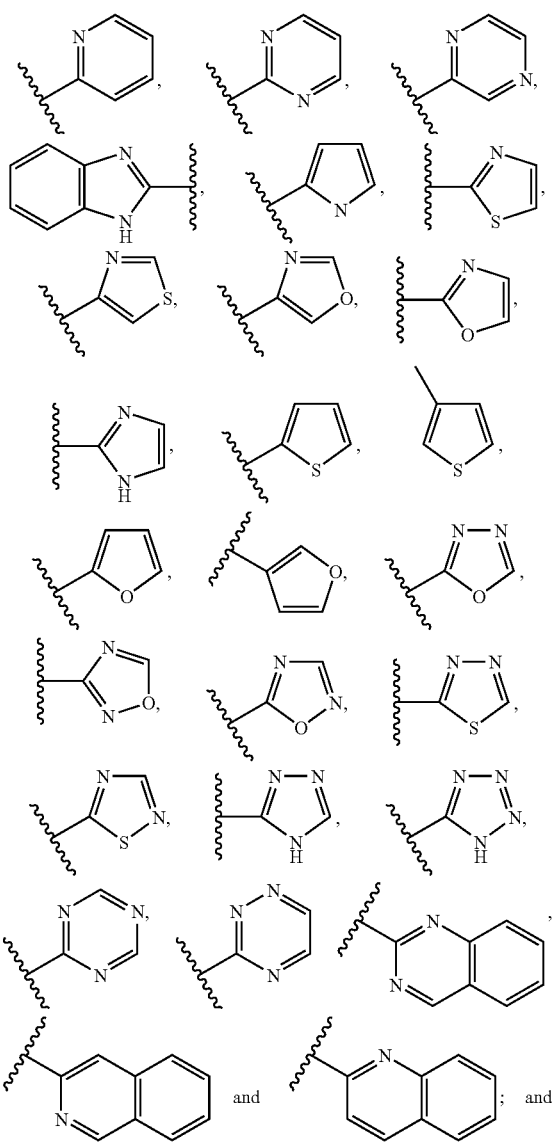

(B) substituted heteroaryl (such as, for example, substituted monocyclic heteroaryl rings, such as, for example, substituted pyridyl (e.g., o-, m-, or p-pyridyl), substituted pyrimidinyl and substituted pyrazinyl, and substituted benzofused heteroaryl rings (i.e., a phenyl ring fused to a heteroaryl ring, wherein either the phenyl ring or the heteroaryl ring is substituted, or both the phenyl ring and the heteroaryl ring are substituted, such as, for example, substituted pyridyl (substituted o-, m-, or p-pyridyl), substituted pyrimidinyl, substituted pyrazinyl, substituted quinazolinyl, substituted isoquinolinyl, and substituted quinolinyl), wherein said R$^2$ substituted heteroaryl is substituted with 1 to 3 (or 1 to 2, or 1) substituents independently selected from the group consisting of: alkyl (e.g., C$_1$ to C$_4$ alkyl, such as, for example, methyl), halo (e.g., Cl, F, and Br, and in another example, F), CN, —CF$_3$, alkoxy (e.g., (C$_1$-C$_4$)alkoxy, such as, for example, —OCH$_3$), halo substituted alkoxy (e.g., halo substituted (C$_1$-C$_4$)alkoxy, such as, for example, —OCF$_3$), cycloalkyl (e.g., C$_3$ to C$_6$ cycloalkyl, such as, for example, cyclopropyl), and halo substituted alkyl (e.g., halo substituted C$_1$-C$_4$alkyl, such as, for example, —CF$_2$CH$_3$), and wherein examples of said R$^2$ substituted heteroaryl include for example, (h) 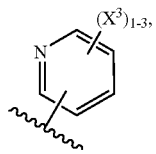

(i) 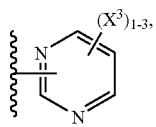

(j) 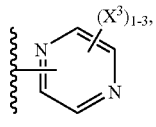

(k) 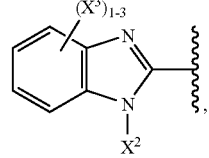

(l) 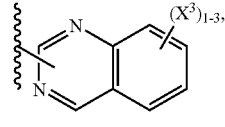

(m) 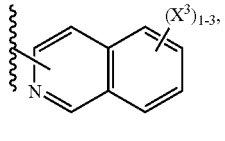

(n) 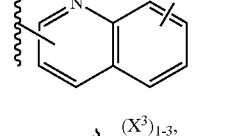

(o) 

(p) 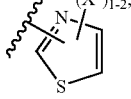

(q) 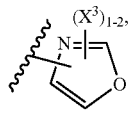

-continued (r) 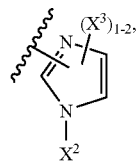

(s) 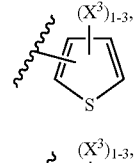

(t) 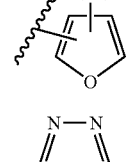

(u) 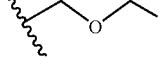

(v) 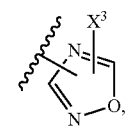

(w) 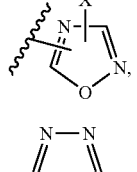

(x) 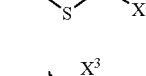

(y) 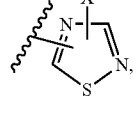

(z) 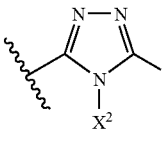

(aa) 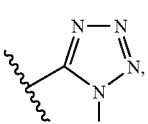

(ab) 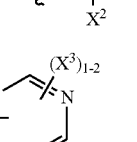

and (ac) 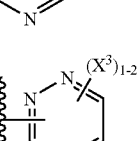

wherein there are preferably 1 or 2 independently selected $X^3$ substitutents and more preferably 1 $X^3$ substituent, and wherein each $X^3$ substituent is selected from the group consisting of: alkyl (e.g., $C_1$ to $C_4$ alkyl, such as, for example, methyl), halo (e.g., Cl, F, and Br, and in another example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein $X^2$ in the benzoimidazolyl-moiety (k) is as previously defined, that is, $X^2$ is selected from the group consisting of: H and alkyl (e.g., $C_1$ to $C_4$ alkyl, such as, for example, methyl), and wherein examples of said $R^2$ substituted heteroaryl include, for example, (h1)

(i1)

(j1)

(k)

(l1)

(m1)

(n1)

(o1)
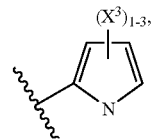

(p1)
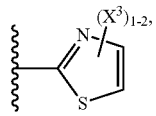

(p2)

(q1)
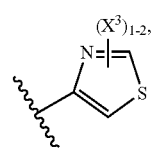

(q2)

(r1)
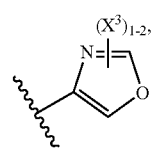

(s1)
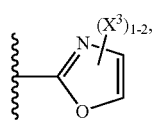

(s2)
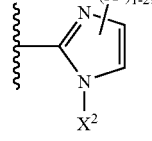

(t1)
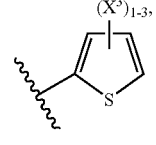

(t2)

(u)
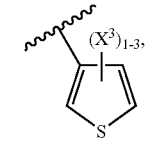

-continued (u1) 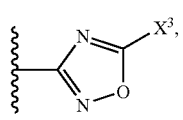

(u2) 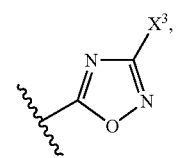

(x) 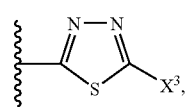

(x1) 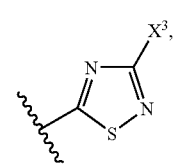

(z) 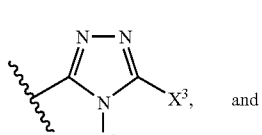 and (aa) 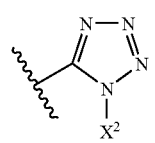

wherein $X^3$ and $X^2$ are as previously described, and wherein examples of said $R^2$ substituted heteroaryl include, for example:

(h2) 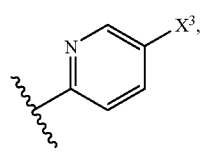

(i2) 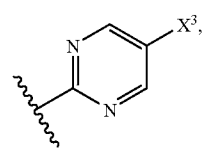

(j2) 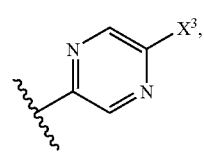

(k1) 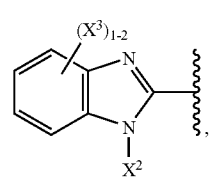

-continued (l1) 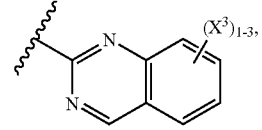

(m1) 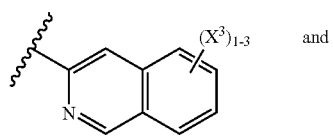 and (n1) 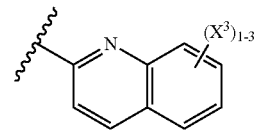

wherein $X^3$ and $X^2$ are as previously described, and wherein examples of said k1 moiety include, for example:

(k2) 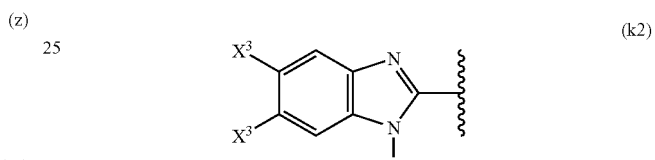

wherein $X^3$ and $X^2$ are as previously described (ice, each $X^3$ is independently selected), and wherein examples of said k2 moiety include, for example, (k3) 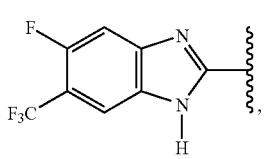

and wherein examples of said $R^2$ group include moieties wherein $R^2$ is selected from the group consisting of: (h), (i), (j), (k), (l), (m), (n), (h1), (i1), (l1), (k1), (j1), (m1), (n1), (h2), (i2), (j2), and (k2) wherein each $X^3$ is independently selected from the group consisting of: Cl, F, —CF$_3$, —OCH$_3$, and —CN, and $X^2$ is selected from the group consisting of: H and —CH$_3$, and wherein examples of said $R^2$ group include moieties wherein $R^2$ is selected from the group consisting of: (h2), (i2), (j2), (k2), (l1), (m1) and (n1) wherein each $X^3$ is independently selected from the group consisting of: Cl, F, Br, —CF$_3$, —OCH$_3$, cyclopropyl, —OCF$_3$, —CF$_2$CH$_3$ and —CN, and $X^2$ is selected from the group consisting of: H and —CH$_3$.

Another embodiment of this invention is directed to compounds of formula I wherein $R^2$ is selected from the group consisting of:

(A) heteroaryl, such as, for example, monocyclic heteroaryl rings such as, for example, pyridyl (o-, m-, or p-pyridyl), pyrimidinyl, and pyrazinyl, and benzofused heteroaryl rings (i.e., a phenyl ring fused to a heteroaryl ring, such as, for example, benzoimidazolyl-, quinazolinyl, isoquinolinyl, and quinolinyl), examples of said heteroaryl moiety include, for example:

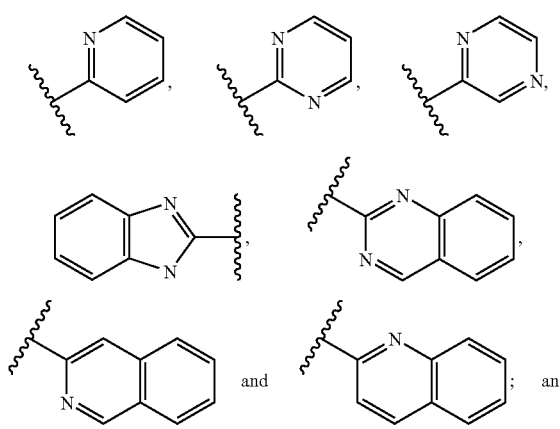

(B) substituted heteroaryl (such as, for example, substituted monocyclic heteroaryl rings, such as, for example, substituted pyridyl (e.g., o-, m-, or p-pyridyl), substituted pyrimidinyl and substituted pyrazinyl, and substituted benzofused heteroaryl rings (i.e., a phenyl ring fused to a heteroaryl ring, wherein either the phenyl ring or the heteroaryl ring is substituted, or both the phenyl ring and the heteroaryl ring are substituted, such as, for example, substituted pyridyl (substituted o-, m-, or p-pyridyl), substituted pyrimidinyl, substituted pyrazinyl, substituted quinazolinyl, substituted isoquinolinyl, and substituted quinolinyl), wherein said $R^2$ substituted heteroaryl is substituted with 1 to 3 (or 1 to 2, or 1) substituents independently selected from the group consisting of: alkyl (e.g., $C_1$ to $C_4$ alkyl, such as, for example, methyl), halo (e.g., Cl, F, and Br, and in another example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein examples of said $R^2$ substituted heteroaryl include for example,

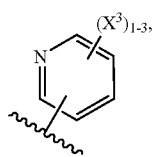

(h)

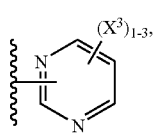

(i)

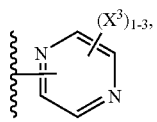

(j)

-continued

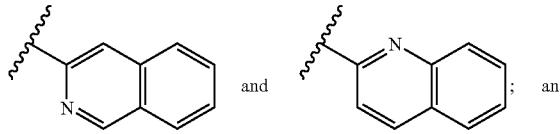

(k)

(l)

(m)

(n)

wherein there are preferably 1 or 2 independently selected $X^3$ substitutents and more preferably 1 $X^3$ substituent, and wherein each $X^3$ substituent is selected from the group consisting of: alkyl (e.g., $C_1$ to $C_4$ alkyl, such as, for example, methyl), halo to (e.g., Cl, F, and Br, and in another example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein $X^2$ in the benzoimidazolyl-moiety (k) is as previously defined, that is, $X^2$ is selected from the group consisting of: H and alkyl (e.g., $C_1$ to $C_4$ alkyl, such as, for example, methyl), and wherein examples of said $R^2$ substituted heteroaryl include, for example,

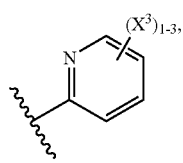

(h1)

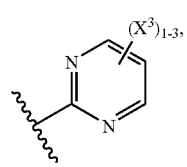

(i1)

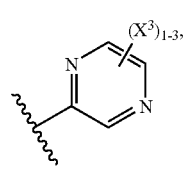

(j1)

-continued (k)
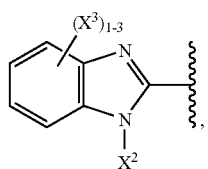

(l1)
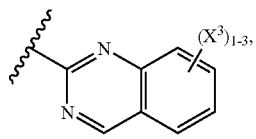

(m1)
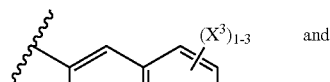 and (n1)
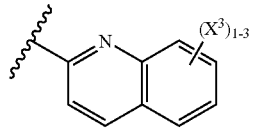

wherein $X^3$ and $X^2$ are as previously described, and wherein examples of said $R^2$ substituted heteroaryl include, for example:

(h2)
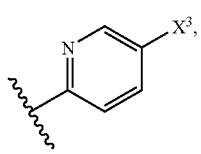

(i2)
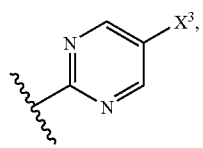

(j2)
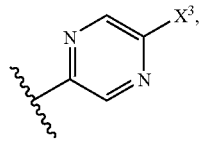

(k1)
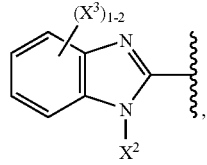

(l1)
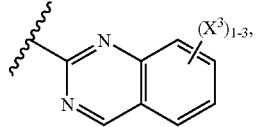

-continued (m1)
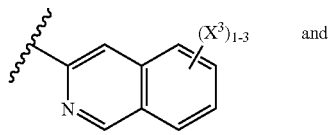 and (n1)
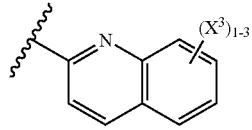

wherein $X^3$ and $X^2$ are as previously described and wherein examples of said k1 moiety include, for example:

(k2)
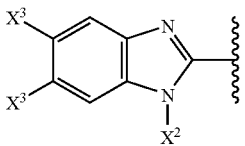

wherein $X^3$ and $X^2$ are as previously described (i.e., each $X^3$ is independently selected), and wherein examples of said kid moiety include, for example, (k3)
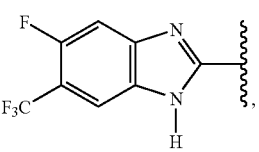

and wherein examples of said $R^2$ group include moieties wherein $R^2$ is selected from the group consisting of: (h), (i), (j), (k), (l), (m), (n), (h1), (i1), (j1), (k1), (l1), (m1), (n1), (h2), (i2), (j2), and (k2) wherein each $X^3$ is independently selected from the group consisting of: Cl, F, —$CF_3$, —$OCH_3$, and —CN, and $X^2$ is selected from the group consisting of: H and —$CH_3$, and wherein examples of said $R^2$ group include moieties wherein $R^2$ is selected from the group consisting of: (h2), (i2), (j2), (k2), (l1), (m1) and (n1) wherein each $X^3$ is independently selected from the group consisting of: Cl, F, Br, —$CF_3$, —$OCH_3$, cyclopropyl, —$OCF_3$, —$CF_2CH_3$ and —CN, and $X^2$ is selected from the group consisting of: H and —$CH_3$.

Another embodiment of this invention is directed to compounds of formula IA wherein $R^2$ is selected from the group consisting of: (A) heteroaryl and (B) substituted heteroaryl, wherein said (A) and (B) groups are as defined as the (A) and (B) groups of $R^2$ in the embodiment above directed to compounds of formula I.

Another embodiment of this invention is directed to compounds of formula IB wherein $R^2$ is selected from the group consisting of: (A) heteroaryl and (B) substituted heteroaryl, wherein said (A) and (B) groups are as defined as the (A) and (B) groups of $R^2$ in the embodiment above directed to compounds of formula I.

Another embodiment of this invention is directed to compounds of formula II wherein $R^2$ is selected from the group consisting of: (A) heteroaryl and (B) substituted heteroaryl, wherein said (A) and (B) groups are as defined as the (A) and (B) groups of $R^2$ in the embodiment above directed to compounds of formula I.

Another embodiment of this invention is directed to compounds of formula IIA wherein $R^2$ is selected from the group consisting of: (A) heteroaryl and (B) substituted heteroaryl, wherein said (A) and (B) groups are as defined as the (A) and (B) groups of $R^2$ in the embodiment above directed to compounds of formula I.

Another embodiment of this invention is directed to compounds of formula IIB wherein $R^2$ is selected from the group consisting of: (A) heteroaryl and (B) substituted heteroaryl, wherein said (A) and (B) groups are as defined as the (A) and (B) groups of $R^2$ in the embodiment above directed to compounds of formula I.

Another embodiment of this invention is directed to any one of the compounds of formulas I, IA, IB, II, IIA, or IIB wherein $R^2$ is moiety (k2) and $X^3$ is as previously defined and $X^2$ is as previously defined.

Another embodiment of this invention is directed to any one of the compounds of formulas I, IA, IB, II, IIA, or IIB wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is as previously defined.

Another embodiment of this invention is directed to any one of the compounds of formulas I, IA, IB, II, IIA, or IIB wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is selected from the group consisting of: H and methyl.

Another embodiment of this invention is directed to a compound of formula IIA wherein $R^2$ is moiety (k2) and $X^3$ is as previously defined and $X^2$ is as previously defined.

Another embodiment of this invention is directed to a compound of formula IIA wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is as previously defined.

Another embodiment of this invention is directed to a compound of formula IIA wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is selected from the group consisting of: H and methyl.

Another embodiment of this invention is directed to a compound of formula IIB wherein $R^2$ is moiety (k2) and $X^3$ is as previously defined and $X^2$ is as previously defined.

Another embodiment of this invention is directed to a compound of formula IIB wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is as previously defined.

Another embodiment of this invention is directed to a compound of formula IIB wherein $R^2$ is moiety (k2) and $X^3$ is selected from the group consisting of: Cl, F, Br, —$CF_3$, —$OCH_3$, cyclopropyl, —$OCF_3$, —$CF_2CH_3$ and —CN, and $X^2$ is selected from the group consisting of: H and methyl.

Another embodiment of this invention is directed to any one of the compounds of formulas I, IA, IB, II, IIA, or IIB wherein $R^2$ is

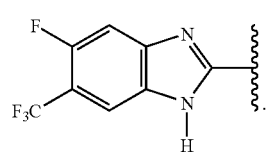

(k3)

Another embodiment of this invention is directed to a compound of formula IIA, wherein $R^2$ is

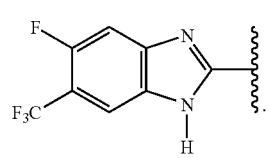

(k3)

Another embodiment of this invention is directed to a compound of formula IIB, wherein $R^2$ is

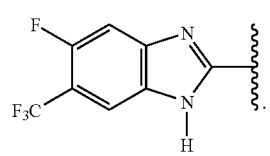

(k3)

Another embodiment of this invention is directed to any one of the compounds of formulas I, IA, IB, II, IIA, or IIB wherein $R^2$ is pyridyl.

Another embodiment of this invention is directed to a compound of formula IIA wherein $R^2$ is pyridyl.

Another embodiment of this invention is directed to a compound of formula IIB wherein $R^2$ is pyridyl.

Another embodiment of this invention is directed to any one of the compounds of formulas I, IA, IB, II, IIA, or IIB wherein $R^2$ is:

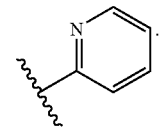

Another embodiment of this invention is directed to a compounds of formula IIA wherein $R^2$ is:

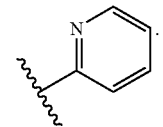

Another embodiment of this invention is directed to a compounds of formula IIB wherein $R^2$ is:

[pyridin-2-yl structure]

[pyrimidin-2-yl structure]

Another embodiment of this invention is directed to any one of the compounds of formulas I, IA, IB, II, IIA, or IIB wherein $R^2$ is selected from the group consisting of: (h), (h1) and (h2), and wherein $X^3$ is as previously defined.

Another embodiment of this invention is directed to a compound of formulas IIA wherein $R^2$ is selected from the group consisting of: (h), (h1) and (h2), and wherein $X^3$ is as previously defined.

Another embodiment of this invention is directed to a compound of formulas IIB wherein $R^2$ is selected from the group consisting of: (h), (h1) and (h2), and wherein $X^3$ is as previously defined.

Another embodiment of this invention is directed to any one of the compounds of formulas I, IA, IB, II, IIA, or IIB wherein $R^2$ is selected from the group consisting of: (h), (h1) and (h2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIA wherein $R^2$ is selected from the group consisting of: (h), (h1) and (h2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is selected from the group consisting of: (h), (h1) and (h2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed to a compound of formulas IIA wherein $R^2$ is (h2), and wherein $X^3$ is as previously defined.

Another embodiment of this invention is directed to a compound of formulas IIB wherein $R^2$ is (h2), and wherein $X^3$ is as previously defined.

Another embodiment of this invention is directed a compounds of formula IIA wherein $R^2$ is (h2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is (h2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed to any one of the compounds of formulas I, IA, IB, II, IIA, or IIB wherein $R^2$ is pyrimidinyl.

Another embodiment of this invention is directed to a compound of formula IIA wherein $R^2$ is pyrimindinyl.

Another embodiment of this invention is directed to a compound of formula IIB wherein $R^2$ is pyrimindinyl.

Another embodiment of this invention is directed to any one of the compounds of formulas I, IA, IB, II, IIA, or IIB wherein $R^2$ is:

Another embodiment of this invention is directed to a compounds of formula IIA wherein $R^2$ is:

[pyrimidinyl structure]

Another embodiment of this invention is directed to a compounds of formula IIB wherein $R^2$ is:

[pyrimidinyl structure]

Another embodiment of this invention is directed to any one of the compounds of formulas I, IA, IB, II, IIA, or IIB wherein $R^2$ is selected from the group consisting of: (i), (i1) and (i2), and wherein $X^3$ is as previously defined.

Another embodiment of this invention is directed to a compound of formulas IIA wherein $R^2$ is selected from the group consisting of: (i), (i1) and (i2), and wherein $X^3$ is as previously defined.

Another embodiment of this invention is directed to a compound of formulas IIB wherein $R^2$ is selected from the group consisting of: (i), (i1) and (i2), and wherein $X^3$ is as previously defined.

Another embodiment of this invention is directed to any one of the compounds of formulas I, IA, IB, II, IIA, or IIB wherein $R^2$ is selected from the group consisting of: (i), (i1) and (i2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIA wherein $R^2$ is selected from the group consisting of: (i), (i1) and (i2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is selected from the group consisting of: (i), (i1) and (i2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed to a compound of formulas IIA wherein $R^2$ is (i2), and wherein $X^3$ is as previously defined.

Another embodiment of this invention is directed to a compound of formulas IIB wherein $R^2$ is (i2), and wherein $X^3$ is as previously defined.

Another embodiment of this invention is directed a compounds of formula IIA wherein $R^2$ is (i2), and wherein $X^3$ is selected from the group consisting of: Cl, F, Br, —CF$_3$, —OCH$_3$, cyclopropyl, —OCF$_3$, —CF$_2$CH$_3$ and —CN.

Another embodiment of this invention is directed a compounds of formula IIB wherein R$^2$ is (i2), and wherein X$^3$ is selected from the group consisting of: Cl, F, Br, —CF$_3$, —OCH$_3$, cyclopropyl, —OCF$_3$, —CF$_2$CH$_3$ and —CN.

Another embodiment of this invention is directed to any one of the compounds of formulas I, IA, IB, II, IIA, or IIB wherein R$^2$ is pyrazinyl.

Another embodiment of this invention is directed to a compound of formula IIA wherein R$^2$ is pyrazinyl.

Another embodiment of this invention is directed to a compound of formula IIB wherein R$^2$ is pyrazinyl.

Another embodiment of this invention is directed to any one of the compounds of formulas I, IA, IB, II, IIA, or IIB wherein R$^2$ is:

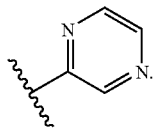

Another embodiment of this invention is directed to a compounds of formula IIA wherein R$^2$ is:

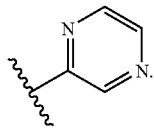

Another embodiment of this invention is directed to a compounds of formula IIB wherein R$^2$ is:

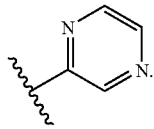

Another embodiment of this invention is directed to any one of the compounds of formulas I, IA, IB, II, IIA, or IIB wherein R$^2$ is selected from the group consisting of: (j), (j1) and (j2), and wherein X$^3$ is as previously defined.

Another embodiment of this invention is directed to a compound of formulas IIA wherein R$^2$ is selected from the group consisting of: (j), (j1) and (j2), and wherein X$^3$ is as previously defined.

Another embodiment of this invention is directed to a compound of formulas IIB wherein R$^2$ is selected from the group consisting of: (j), (j1) and (j2), and wherein X$^3$ is as previously defined.

Another embodiment of this invention is directed to any one of the compounds of formulas I, IA, IB, II, IIA, or IIB wherein R$^2$ is selected from the group consisting of: (j), (j1) and (j2), and wherein each X$^3$ is independently selected from the group consisting of: Cl, F, Br, —CF$_3$, —OCH$_3$, cyclopropyl, —OCF$_3$, —CF$_2$CH$_3$ and —CN.

Another embodiment of this invention is directed a compounds of formula IIA wherein R$^2$ is selected from the group consisting of: (j), (j1) and (j2), and wherein each X$^3$ is independently selected from the group consisting of, Cl, F, Br, —CF$_3$, —OCH$_3$, cyclopropyl, —OCF$_3$, —CF$_2$CH$_3$ and —CN.

Another embodiment of this invention is directed a compounds of formula IIB wherein R$^2$ is selected from the group consisting of: (j), (j1) and (j2), and wherein each X$^3$ is independently selected from the group consisting of: Cl, F, Br, —CF$_3$, —OCH$_3$, cyclopropyl, —OCF$_3$, —CF$_2$CH$_3$ and —CN.

Another embodiment of this invention is directed to a compound of formulas IIA wherein R$^2$ is (j2), and wherein X$^3$ is as previously defined.

Another embodiment of this invention is directed to a compound of formulas IIB wherein R$^2$ is (j2), and wherein X$^3$ is as previously defined.

Another embodiment of this invention is directed a compounds of formula IIA wherein R$^2$ is (j2), and wherein X$^3$ is selected from the group consisting of: Cl, F, Br, —CF$_3$, —OCH$_3$, cyclopropyl, —OCF$_3$, —CF$_2$CH$_3$ and —CN.

Another embodiment of this invention is directed a compounds of formula IIB wherein R$^2$ is (j2), and wherein X$^3$ is selected from the group consisting of: Cl, F, Br, —CF$_3$, —OCH$_3$, cyclopropyl, —OCF$_3$, —CF$_2$CH$_3$ and —CN.

Another embodiment of this invention is directed to any one of the compounds of formulas I, IA, IB, II, IIA, or IIB wherein R$^2$ is quinazolinyl.

Another embodiment of this invention is directed to a compound of formula IIA wherein R$^2$ is quinazolinyl.

Another embodiment of this invention is directed to a compound of formula IIB wherein R$^2$ is quinazolinyl.

Another embodiment of this invention is directed to any one of the compounds of formulas I, IA, IB, II, IIA, or IIB wherein R$^2$ is:

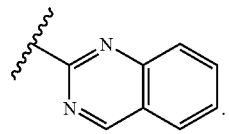

Another embodiment of this invention is directed to a compounds of formula IIA wherein R$^2$ is:

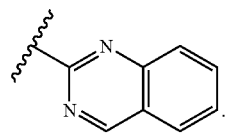

Another embodiment of this invention is directed to a compounds of formula IIB wherein R$^2$ is:

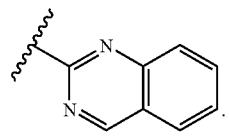

Another embodiment of this invention is directed to any one of the compounds of formulas I, IA, IB, II, IIA, or IIB wherein R$^2$ is selected from the group consisting of: (l), (l1) and (l2), and wherein X$^3$ is as previously defined.

Another embodiment of this invention is directed to a compound of formulas IIA wherein $R^2$ is selected from the group consisting of: (l), (l1) and (l2), and wherein $X^3$ is as previously defined.

Another embodiment of this invention is directed to a compound of formulas IIB wherein $R^2$ is selected from the group consisting of: (l), (l1) and (l2), and wherein $X^3$ is as previously defined.

Another embodiment of this invention is directed to any one of the compounds of formulas I, IA, IB, II, IIA, or IIB wherein $R^2$ is selected from the group consisting of: (l), (l1) and (l2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIA wherein $R^2$ is selected from the group consisting of: (l), (l1) and (l2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is selected from the group consisting of: (l), (l1) and (l2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed to a compound of formulas IIA wherein $R^2$ is (l2), and wherein $X^3$ is as previously defined.

Another embodiment of this invention is directed to a compound of formulas IIB wherein $R^2$ is (l2), and wherein $X^3$ is as previously defined.

Another embodiment of this invention is directed a compounds of formula IIA wherein $R^2$ is (l2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is (l2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed to any one of the compounds of formulas I, IA, IB, II, IIA, or IIB wherein $R^2$ is isoquinolinyl.

Another embodiment of this invention is directed to a compound of formula IIA wherein $R^2$ is isoquinolinyl.

Another embodiment of this invention is directed to a compound of formula IIB wherein $R^2$ is isoquinolinyl.

Another embodiment of this invention is directed to any one of the compounds of formulas I, IA, IB, II, IIA, or IIB wherein $R^2$ is:

[isoquinolinyl structure]

Another embodiment of this invention is directed to a compounds of formula IIA wherein $R^2$ is:

[isoquinolinyl structure]

Another embodiment of this invention is directed to a compounds of formula IIB wherein $R^2$ is:

[isoquinolinyl structure]

Another embodiment of this invention is directed to any one of the compounds of formulas I, IA, IB, II, IIA, or IIB wherein $R^2$ is selected from the group consisting of: (m), (m1) and (m2), and wherein $X^3$ is as previously defined.

Another embodiment of this invention is directed to a compound of formulas IIA wherein $R^2$ is selected from the group consisting of: (m), (m1) and (m2), and wherein $X^3$ is as previously defined.

Another embodiment of this invention is directed to a compound of formulas IIB wherein $R^2$ is selected from the group consisting of: (m), (m1) and (m2), and wherein $X^3$ is as previously defined.

Another embodiment of this invention is directed to any one of the compounds of formulas I, IA, IB, II, IIA, or IIB wherein $R^2$ is selected from the group consisting of: (m), (m1) and (m2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIA wherein $R^2$ is selected from the group consisting of: (m), (m1) and (m2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is selected from the group consisting of: (m), (m1) and (m2), and wherein each $X^3$ is independently selected from the group consisting of: Cl, F, Br, —$CF_3$, —$OH_3$, cyclopropyl, —$OCF_3$, —$CF_2CH_3$ and —CN.

Another embodiment of this invention is directed to a compound of formulas IIA wherein $R^2$ is (m2), and wherein $X^3$ is as previously defined.

Another embodiment of this invention is directed to a compound of formulas IIB wherein $R^2$ is (m2), and wherein $X^3$ is as previously defined.

Another embodiment of this invention is directed a compounds of formula IIA wherein $R^2$ is (m2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is (m2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed to any one of the compounds of formulas I, IA, IB, II, IIA, or IIB wherein $R^2$ is quinolinyl.

Another embodiment of this invention is directed to a compound of formula IIA wherein $R^2$ is quinolinyl.

Another embodiment of this invention is directed to a compound of formula IIB wherein $R^2$ is quinolinyl.

Another embodiment of this invention is directed to any one of the compounds of formulas I, IA, IB, II, IIA, or IIB wherein $R^2$ is:

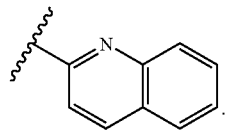

Another embodiment of this invention is directed to a compounds of formula IIA wherein $R^2$ is:

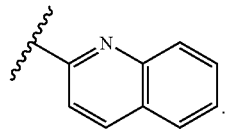

Another embodiment of this invention is directed to a compounds of formula IIB wherein $R^2$ is:

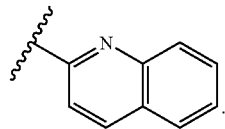

Another embodiment of this invention is directed to any one of the compounds of formulas I, IA, IB, II, IIA, or IIB wherein $R^2$ is selected from the group consisting of: (n), (n1) and (n2), and wherein $X^3$ is as previously defined.

Another embodiment of this invention is directed to a compound of formulas IIA wherein $R^2$ is selected from the group consisting of: (n), (n1) and (n2), and wherein $X^3$ is as previously defined.

Another embodiment of this invention is directed to a compound of formulas IIB wherein $R^2$ is selected from the group consisting of: (n), (n1) and (n2), and wherein $X^3$ is as previously defined.

Another embodiment of this invention is directed to any one of the compounds of formulas I, IA, IB, II, IIA, or IIB wherein $R^2$ is selected from the group consisting of: (n), (n1) and (n2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIA wherein $R^2$ is selected from the group consisting of: (n), (n1) and (n2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is selected from the group consisting of: (n), (n1) and (n2), and wherein each $X^3$ is independently selected from the group consisting of: Cl, F, Br, —$CF_3$, —$OCH_3$, cyclopropyl, —$OCF_3$, —$CF_2CH_3$ and —CN.

Another embodiment of this invention is directed to a compound of formulas IIA wherein $R^2$ is (n2), and wherein $X^3$ is as previously defined.

Another embodiment of this invention is directed to a compound of formulas IIB wherein $R^2$ is (n2), and wherein $X^3$ is as previously defined.

Another embodiment of this invention is directed a compounds of formula IIA wherein $R^2$ is (n2), and wherein $X^3$ is selected from the group consisting of: Cl, F, Br, —$CF_3$, —$OCH_3$, cyclopropyl, —$OCF_3$, —$CF_2CH_3$ and —CN.

Another embodiment of this invention is directed a compounds of formula IIB wherein $R^2$ is (n2), and wherein $X^3$ is selected from the group consisting of: Cl, F, Br, —$CF_3$, —$OCH_3$, cyclopropyl, —$OCF_3$, —$CF_2CH_3$ and —CN.

In one embodiment, $R^3$ is —H.

In another embodiment, $R^3$ is aryl.

In still another embodiment, $R^3$ is phenyl substituted with —F, —Br or —I

In another embodiment, $R^3$ is phenyl substituted with —F.

In a further embodiment, $R^3$ is phenyl substituted with —Br.

In yet another embodiment, $R^3$ is phenyl substituted with —OH.

In one another embodiment, $R^3$ is phenyl substituted with —$OCH_3$.

In another embodiment, $R^3$ is heteroaryl.

In one embodiment, $R^3$ is:

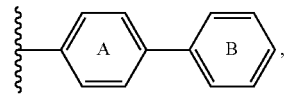

wherein each of rings A and B may be optionally and independently substituted with 1-5 groups selected from -halo, —OH, -alkyl, -alkoxy, —SH, -thioalkyl, —N($R^{14}$)$_2$, —$NO_2$, —CN, —$CF_3$, —OC(O)$R^{14}$, —OC(O)—$R^{14}$, —C(O)O$R^{14}$, —C(O)O—$R^{14}$, $R^6$-aryl-, $R^7$, $R^8$, $R^9$ or $R^{10}$.

In various embodiments, $R^3$ is

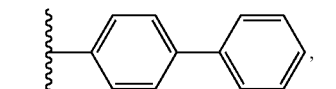

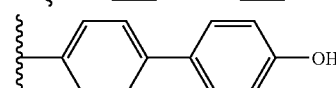

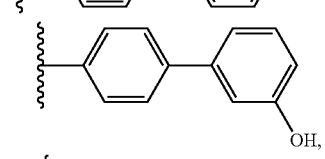

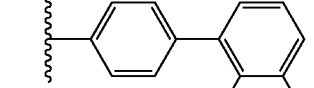

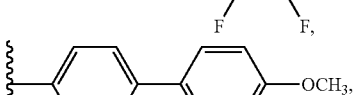

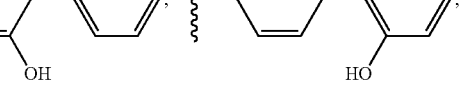

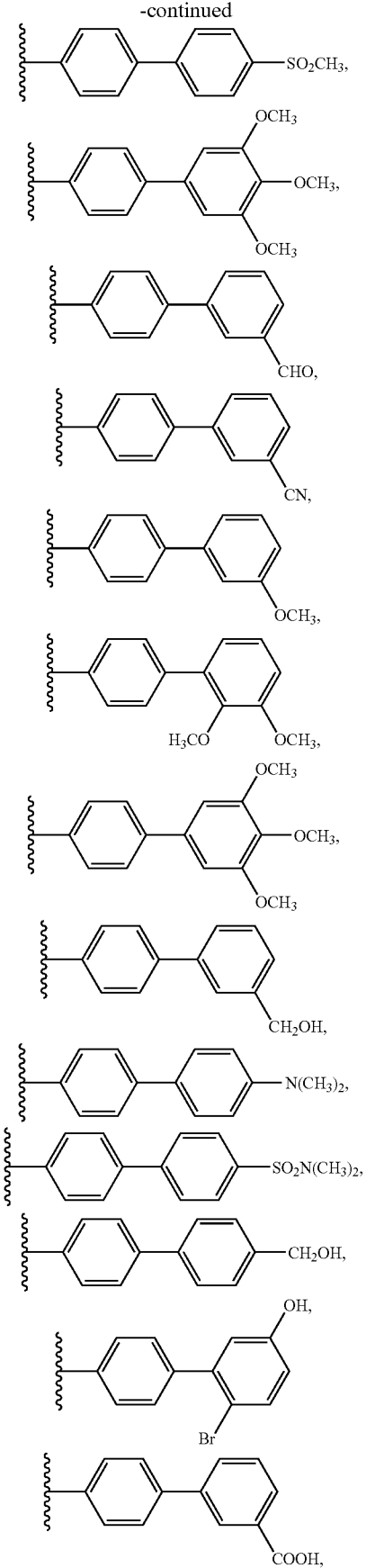
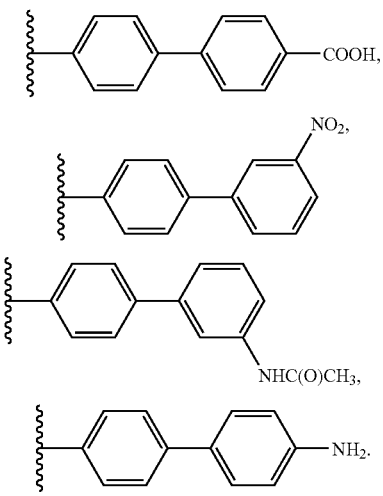
In one embodiment, R³ is -phenyl, which is substituted with
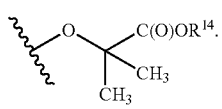
In various embodiments, R³ is
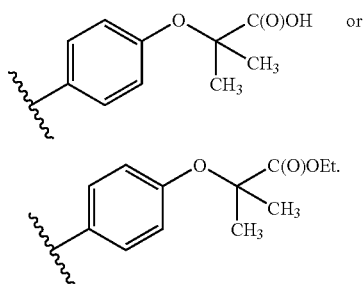
In one embodiment, R³ is -phenyl, which is substituted with
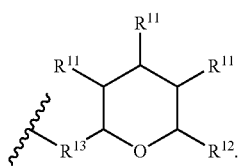
In various embodiments, R³ is
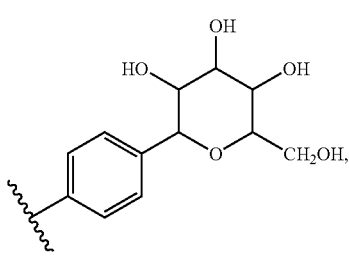

-continued

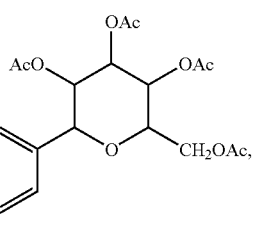

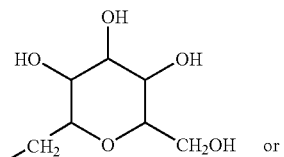 or

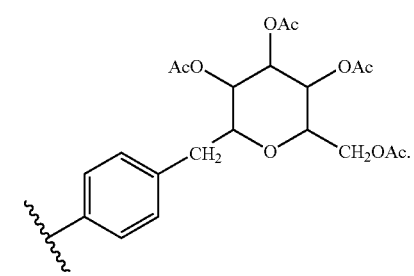

In another embodiment, R³ is -phenyl, which is substituted with

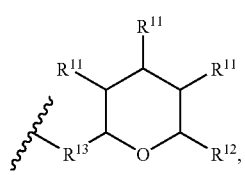

wherein R¹³ is -alkylene-, -oxaalkylene- or -alkenylene-, each occurrence of R¹¹ is —OH or —OAc, and R¹² is —CH₂OH or —CH₂OAc.

In one embodiment, R³ is -phenyl, which is substituted with

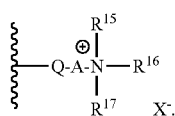

In various embodiments, R³ is

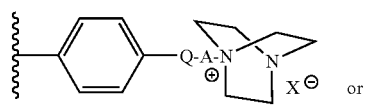 or

-continued

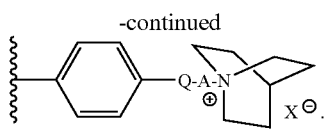

In one embodiment -Q-A- is

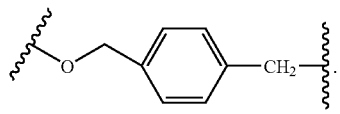

In another embodiment, R³ is

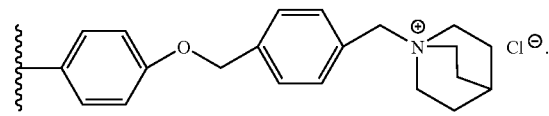

In one embodiment, R³ is

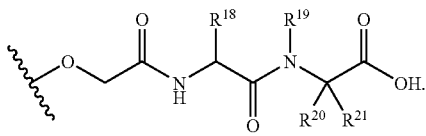

In various embodiments, R³ is

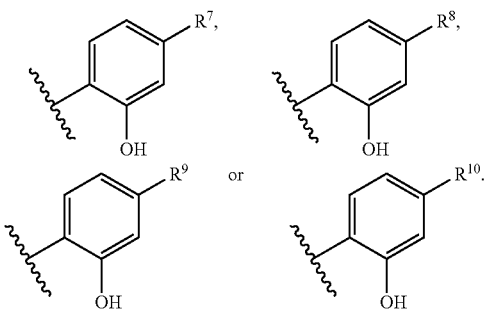

In one embodiment, R³ is phenyl which is substituted with

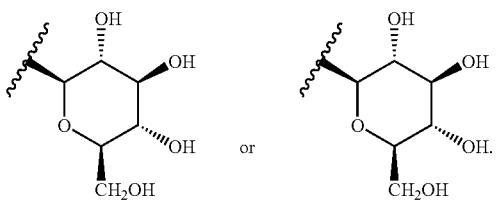

Another embodiment of this invention is directed to a compound of formula I (e.g., a compound of formula IA, IB, II, IIA, or IIB) wherein R¹ is as defined in any one of the embodiments described above, R² is as defined in any one of the embodiments described above, and R³ is as defined in any one of the embodiments described above.

Another embodiment of this invention is directed to compounds of formula I (e.g., a compound of formula IA, IB, II, IIA or IIB) wherein:

(A) $R^1$ is selected from the group consisting of: any one of the $R^1$ embodiments described above;

(B) $R^2$ is selected from the group consisting of:

(1) heteroaryl, such as, for example, monocyclic heteroaryl rings such as, for example, pyridyl (o-, m-, or p-pyridyl), pyrimidinyl, and pyrazinyl, and benzofused heteroaryl rings (i.e., a phenyl ring fused to a heteroaryl ring, such as, for example, benzoimidazolyl-, quinazolinyl, isoquinolinyl, and quinolinyl), examples of said heteroaryl moiety include, for example:

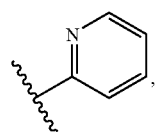 , 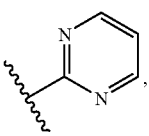 , 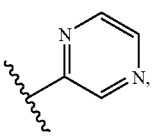 ,

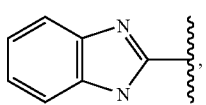 , 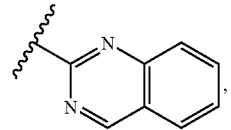 ,

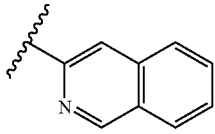 and 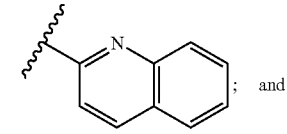 ; and (2) substituted heteroaryl (such as, for example, substituted monocyclic heteroaryl rings, such as, for example, substituted pyridyl (e.g., o-, m-, or p-pyridyl), substituted pyrimidinyl and substituted pyrazinyl, and substituted benzofused heteroaryl rings (i.e., a phenyl ring fused to a heteroaryl ring, wherein either the phenyl ring or the heteroaryl ring is substituted, or both the phenyl ring and the heteroaryl ring are substituted, such as, for example, substituted pyridyl (substituted o-, m-, or p-pyridyl), substituted pyrimidinyl, substituted pyrazinyl, substituted quinazolinyl, substituted isoquinolinyl, and substituted quinolinyl), wherein said $R^2$ substituted heteroaryl is substituted with 1 to 3 (or 1 to 2, or 1) substituents independently selected from the group consisting of: alkyl (e.g., $C_1$ to $C_4$ alkyl, such as, for example, methyl), halo (e.g., Cl, F, and Br, and in one example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein examples of said $R^2$ substituted heteroaryl include for example,

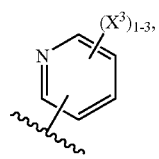 (h)

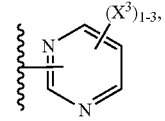 (i)

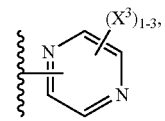 (j)

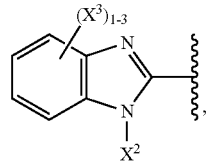 (k)

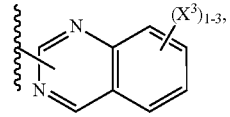 (l)

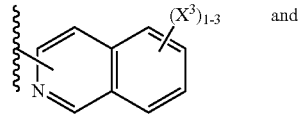 and (m)

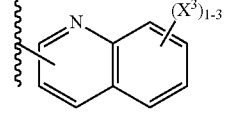 (n)

wherein there are preferably 1 or 2 independently selected $X^3$ substitutents and more preferably 1 $X^3$ substituent, and wherein each $X^3$ substituent is selected from the group consisting of, alkyl (e.g., $C_1$ to $C_4$ alkyl, such as, for example, methyl), halo (e.g., Cl, F, and Br, and in one example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and wherein $X^2$ in the benzoimidazolyl-moiety (k) is as previously defined, that is, $X^2$ is selected from the group consisting of: H and alkyl (e.g., $C_1$ to $C_4$ alkyl, such as, for example, methyl), and wherein examples of said $R^2$ substituted heteroaryl include, for example,

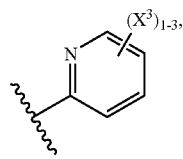 (h1)

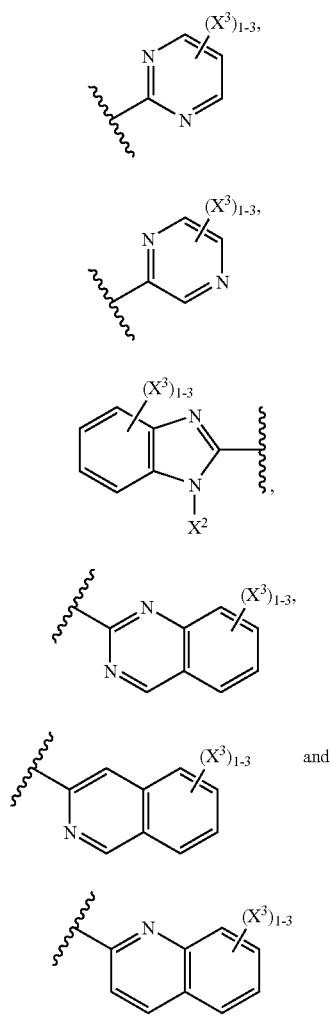

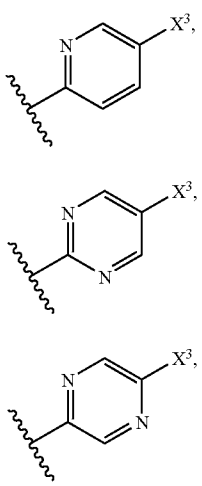

wherein $X^3$ and $X^2$ are as previously described, and wherein examples of said $R^2$ substituted heteroaryl include, for example:

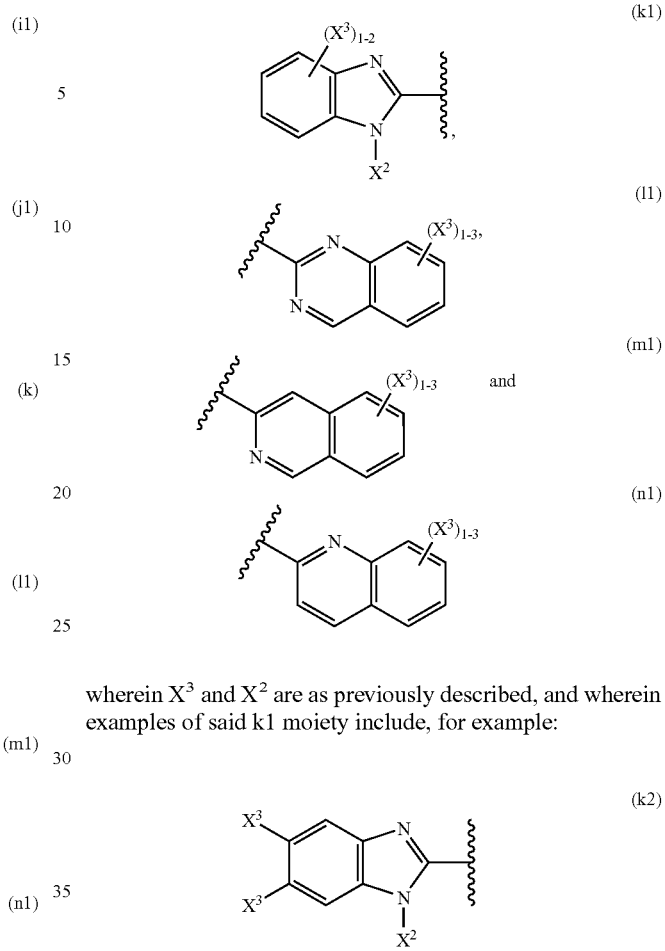

wherein $X^3$ and $X^2$ are as previously described, and wherein examples of said k1 moiety include, for example:

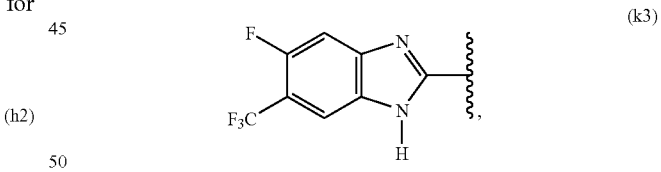

wherein $X^3$ and $X^2$ are as previously described (i.e., each $X^3$ is independently selected), and wherein examples of said k2 moiety include, for example, and wherein examples of said $R^2$ group include moieties wherein $R^2$ is selected from the group consisting of: (h), (i), (j), (k), (l), (m), (n), (h1), (i1), (j1), (k1), (l1), (m1), (n1), (h2), (i2), (j2), and (k2) wherein each $X^3$ is independently selected from the group consisting of: Cl, F, —CF$_3$, —OCH$_3$, and —CN, and $X^2$ is selected from the group consisting of: H and —CH$_3$, and wherein examples of said $R^2$ group include moieties wherein $R^2$ is selected from the group consisting of: (h2), (i2), (j2), (k2), (l1), (m1) and (n1) wherein each $X^3$ is independently selected from the group consisting of: Cl, F, Br, —CF$_3$, —OCH$_3$, cyclopropyl, —OCF$_3$, —CF$_2$CH$_3$ and —CN, and $X^2$ is selected from the group consisting of: H and —CH$_3$; and (C) $R^3$ is selected from the group consisting of: any one of the $R^3$ embodiments described above.

Another embodiment of this invention is directed to compounds of formula I (e.g., a compound of formula IA, IB, II, IIA, or IIB) wherein:

(A) $R^1$ is selected from the group consisting of: any one of the $R^1$ embodiments described above, (B) $R^2$ is selected from the group consisting of: pyridyl (e.g., o-pyridyl), pyrimidinyl, pyrazinyl, benzoimidazolyl, quinazolinyl, isoquinoliny, quinolinyl, substituted pyridyl (e.g., substituted o-pyridyl), substituted pyrimindinyl, substituted pyrazinyl, substituted benzoimidazolyl, substituted quinazolinyl, substituted isoquinolinyl, and substituted quinolinyl, wherein said substituted groups are substituted with 1 to 3 substitutents selected from the group consisting of: alkyl (e.g., $C_1$ to $C_4$ alkyl, such as, for example, methyl), halo (e.g., Cl, F, and Br, and in one example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$) alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and (C) $R^3$ is selected from the group consisting of: any one of the $R^3$ embodiments described above.

Another embodiment of this invention is directed to compounds of formula I (e.g., a compound of formula IA, IB, II, IIA, or IIB) wherein:

(A) $R^1$ is selected from the group consisting of: any one of the $R^1$ embodiments described above, (B) $R^2$ is selected from the group consisting of:

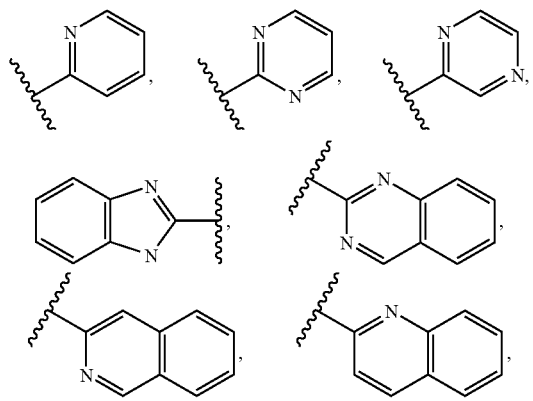

(h2), i(2), j(2), (k2), (l1), (m1) and (n1), wherein each $X^3$ is independently selected from the group consisting of: alkyl (e.g., $C_1$ to $C_4$ alkyl, such as, for example, methyl), halo (e.g., Cl, F, and Br, and in one example, F), CN, —$CF_3$, alkoxy (e.g., ($C_1$-$C_4$)alkoxy, such as, for example, —$OCH_3$), halo substituted alkoxy (e.g., halo substituted ($C_1$-$C_4$)alkoxy, such as, for example, —$OCF_3$), cycloalkyl (e.g., $C_3$ to $C_6$ cycloalkyl, such as, for example, cyclopropyl), and halo substituted alkyl (e.g., halo substituted $C_1$-$C_4$alkyl, such as, for example, —$CF_2CH_3$), and $X^2$ is selected from the group consisting of: H and alkyl (e.g., $C_1$ to $C_4$ alkyl, such as, for example, methyl), and (C) $R^3$ is selected from the group consisting of: any one of the $R^3$ embodiments described above, For compounds of formula I (e.g., compounds of formula IA and IB), $R^4$ and $R^5$ are preferably each —$CH_2$— and u and v are preferably each 2, i.e., $R^4$ and are $R^5$ are preferably each —$CH_2$—$CH_2$—.

As used above, and throughout this disclosure, the following terms, unless otherwise indicated, shall be understood to have the following meanings:

"At least one" compound of formula I means 1, 2, 3 or 4 different compounds, but preferably one compound of formula I is used in the claimed methods. Similarly, when "at least one" is used in connection with the additional agents used in the combinations, 1, 2, 3 or 4 additional agents are contemplated, but preferably one or two, more preferably one additional agent is used.

"Patient" includes both human and animals. A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"PG" means protecting group.

"Mammal" means humans and other mammalian animals.

"Alkyl" means an aliphatic hydrocarbon group which may be straight or to branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C($CH_3$)=CH—, and —CH=CH$CH_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzothiadiazolyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Benzofused cycloalkyl", "benzofused cycloalkenyl", "benzofused heterocycloalkyl", and "benzofused heterocycloalkenyl" mean cycloalkyl, cycloalkenyl, heterocycloalkyl or heterocycloalkenyl rings fused to a benzene ring at two adjacent carbon atoms of the non-aromatic rings, for example:

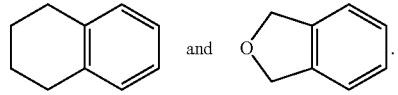

The rings are joined to the rest of the molecule by a bond to the non-aromatic ring.

"Halogen" means fluorine, chlorine, bromine, or iodine, Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl —C(=N—CN)—NH$_2$, —C(=NH)—NH$_2$, —C(—NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are —(CH$_2$)$_3$—, —(CH$_2$)$_4$—, —O—CH$_2$—O—, —O(CH$_2$)$_2$—O, —O(CH$_2$)$_3$-O, —NH—NH—NH—, —NH—S—NH—, —NH—O—NH—, or —NH—NH—C(O)—, and the like which form moieties such as, for example:

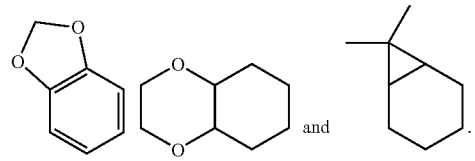

When R$^1$, R$^2$ and/or R$^3$ is an aryl or heteroaryl ring, the ring system substituent can also be a sugar, a polyol, a glucuronide or a sugar carbamate.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" or "heterocycloalkyl" may also be substituted by a moiety which simultaneously replaces two available hydrogens on the same carbon atom on a ring system (e.g., carbonyl). An example of such moiety is:

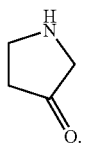

"Heterocyclylalkyl" or "heterocycloalkylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" or "heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also be substituted by a moiety which simultaneously replaces two available hydrogens on the same carbon atom on a ring system (e.g., carbonyl). An example of such moiety is:

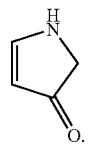

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

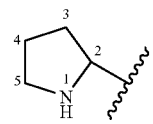

there is no —OH attached directly to carbons marked 2 and 5.

It should also be noted that tautomeric forms such as, for example, the moieties:

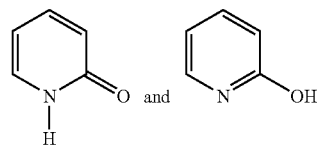

are considered equivalent in certain embodiments of this invention.

"Heteroaralkyl" or "heteroarylalkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Polyol" means a compound or residue having a plurality of —OH groups; in particular, polyols are alkyl groups in which a plurality of C—H bonds are replaced by C—OH bonds. Typical polyols include glycerol, erythritol, sorbitol, xylitol, mannitol, and inositol. Linear polyol residues generally have the empirical formula —C$_y$H$_{2y+1}$O$_y$, and cyclic polyol residues generally have the formula —C$_y$H$_{2y-1}$O$_y$—. Polyols wherein y is 3, 4, 5 or 6 are preferred. Cyclic polyols also include reduced sugars such as glucitol.

"Sugar" means a carbohydrate comprised of one or two saccharose groups. Monosaccharide sugars, also known as simple sugars, are composed of chains of 2-7 carbon atoms, wherein one of the carbons carries aldehydic or ketonic oxygen, which may be combined in acetal or ketal forms. The remaining carbons usually have hydrogen atoms and hydroxyl groups, or protecting groups for hydroxyl, such as acetate. Typical monosaccharides considered "sugars" in the present invention are arabinose, ribose, xylose, xylulose, deoxyribose, galactose, glucose, mannose, fructose, sorbose, tagatose, fucose, quinovose, rhamnose, manno-heptulose and sedoheptulose. Typical disaccharides are sucrose, lactose, maltose and cellobiose. Unless specifically modified, the term "sugar" refers to both D-sugars and L-sugars. The sugar may be protected. The sugar can be attached through an oxygen or a carbon.

Reduced C-attached sugars or C-glycosyl compounds are also encompassed by the invention. The reduced sugars (e.g., glucitol) can be classified as either polyols or sugars, and are also known as alditols. Alditols are polyols having the general formula HOCH$_2$[CH(OH)]$_x$CH$_2$OH.

"Glucuronide" means a glycoside of glucuronic acid,

"Sugar carbamate" means a mono-, di- or oligo-saccharide in which one or more hydroxyl groups are derivatized as carbamates, particularly as phenyl carbamates or substituted phenyl carbamates.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or in Formula I or II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)-aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1)1-19; P. Gould, *International J. of Pharmaceutics* (1986) 33,201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxyethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.)

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

Those skilled in the art will appreciate that for some of the compounds of Formula I, one isomer will show greater pharmacological activity than other isomers.

One to three compounds of formula I can be administered in the methods of the invention, preferably one.

For preparing pharmaceutical compositions from the compounds described for use in the methods of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds for use in the present invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound of formula I is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from the diseases or conditions listed above.

The doses and dosage regimen of the other agents used in the treatment of diseases or conditions listed above will be determined by the attending clinician in view of the approved doses and dosage regimen in the package insert, taking into consideration the age, sex and condition of the patient and the severity of the disease. When administered in combination, the compound(s) of formula I and the other agent(s) for treating diseases or conditions listed above can be administered simultaneously or sequentially. This is particularly useful when the components of the combination are preferably given on different dosing schedules, e.g., one component is administered once daily and another every six hours, or when the preferred pharmaceutical compositions are different, e.g. one is preferably a tablet and one is a capsule. A kit comprising the separate dosage forms is therefore advantageous.

Additional agents udeful for treating pain include non-opioid (also known as non-steroidal anti-inflammatories) analgesics such as acetylsalicylic acid, choline magnesium trisalicylate, acetaminophen, ibuprofen, fenoprofen, diflusinal, and naproxen; opioid analgesics such as morphine, hydromorphone, methadone, levorphanol, fentanyl, oxycodone, and oxymorphone; steroids such as prednisolone, fluticasone, triamcinolone, beclomethasone, mometasone, budisamide, betamethasone, dexamethasone, prednisone, flunisolide and cortisone; COX-I inhibitors such as aspirin and piroxicam; COX-II inhibitors such as rofecoxib, celecoxib, valdecoxib and etoricoxib; agents useful for treating inflammatory bowel disease such as IL-10, steroids, and azulfidine; and agents useful for treating rheumatoid arthritis such as methotrexate, azathioprine, cyclophosphamide, steroids and mycophenolate mofetil.

Especially preferred agents for treating neuropathic pain are opioid and non-opioid analgesics, including acetylsalicylic acid, choline magnesium trisalicylate, acetaminophen, ibuprofen, fenoprofen, diflusinal, naproxen, morphine, hydromorphone, methadone, levorphanolt, fentanyl, oxycodone, and oxymorphone. Especially preferred agents for treating inflammatory pain are steroids and non-opioid analgesic agents.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

General Methods

The general methods described in this paragraph can be used unless stated otherwise in the examples below. All solvents and reagents can be used as received. Proton NMR spectra can be obtained using a Varian XL-400 (400 MHz) instrument and can be reported as parts per million (ppm) downfield from $Me_4Si$. LCMS analysis can be performed using an Applied Biosystems API-100 mass spectrometer equipped with a Shimadzu SCL-10A LC column: Altech platinum C18, 3 um, 33 mm×7 mm ID; gradient flow: 0 min, 10% $CH_3CN$; 5 min, 95% $CH_3CN$; 7 min, 95% $CH_3CN$; 7.5 min, 10% $CH_3CN$; 9 min, stop. Flash column chromatography can be performed using Selecto Scientific flash silica gel, 32-63 mesh. Analytical and preparative TLC can be performed using Analtech Silica gel GF plates. Chiral HPLC can be performed using a Varian PrepStar system equipped with a Chiralpak OD column (Chiral Technologies).

In the Schemes that follow, the following abbreviations are used: DMED (dimethylethylenediamine); Ac (acetyl); Me (methyl); Et (ethyl); Ph (phenyl); Bn (benzyl); Boc (tert-butoxycarbonyl); DCE (dichloroethane); DMSO ($d_6$-dimethylsulfoxide); DIPEA (diisopropylethylamine); Dioxane (1,4-dioxane); EtOAc (ethyl acetate); EtOH (ethanol); Ether (diethyl ether); HOBT (1-hydroxybenzotriazole hydrate); IPA (isopropyl alcohol); LCMS (liquid chromatography mass spectrometry); LDA (lithium diisopropylamide); LHMSD (lithium bis(trimethylsilyl)amide); MeOH (methanol); RT (Room temperature, about 25° C.); $SiO_2$ (silica gel for flash chromatography); TFA (trifluoroacetic acid); TLC (thin layer chromatography); THF (tetrahydrofuran).

Scheme 1 (Method A)

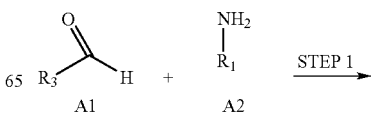

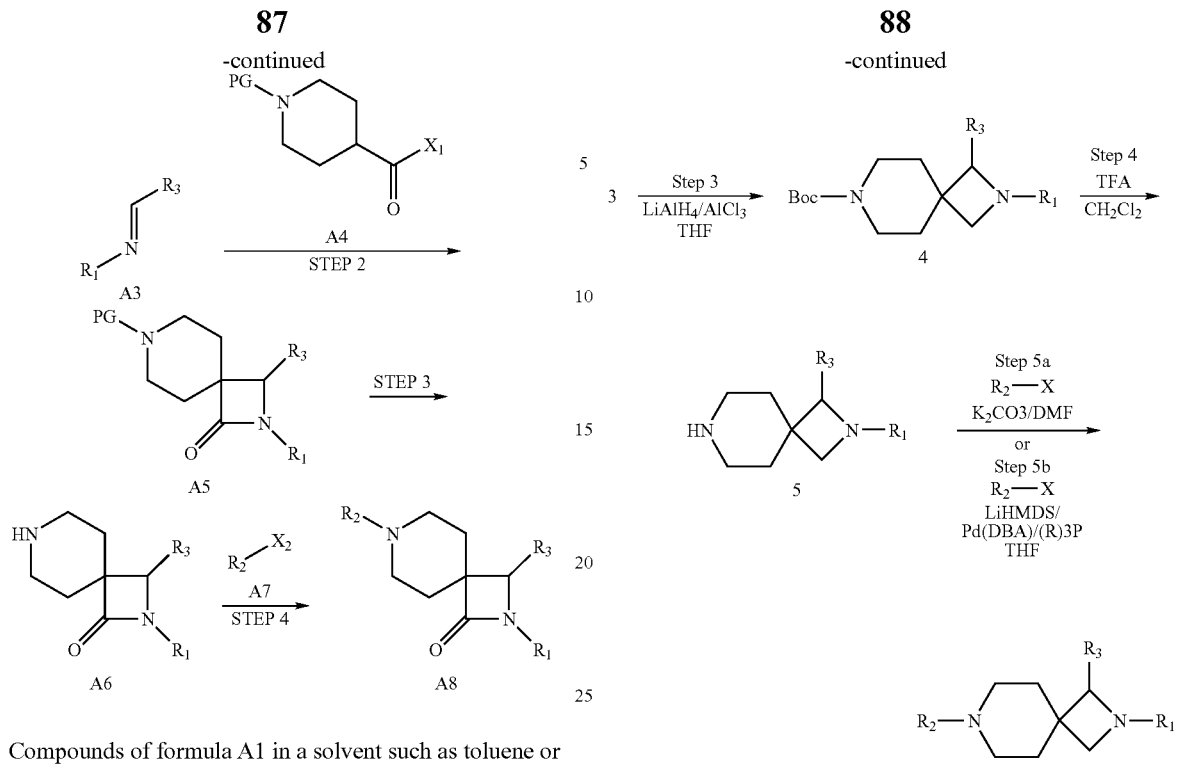

Compounds of formula A1 in a solvent such as toluene or isopropanol can be treated with a compound of formula A2 to provide a compound of formula A3. A Compound of formula A4 (where X1 is a halogen or alkoxy group such as OEt) can be treated with a base such as LDA or LHMDS at −78° C. followed by compound of formula A3 at room temperature to provide compound of formula A5. A Compound of formula A5 can be converted into compound of formula A6 by removing the protecting group (for example where PG=Boc, by the treatment with HCl-dioxane). A Compound of formula A6 can be converted into compound of formula A8 by the treatment with compound of formula A7

Additionally, the compounds of this invention can be prepared using a related Method B (Scheme 2) wherein the unsubstitued lactams such as compounds 2 are prepared and converted into compounds 3 to introduce the appropriate $R^1$ group. Reaction of 3 according to steps 3, 4 and 5 will then provided the desired compounds 6

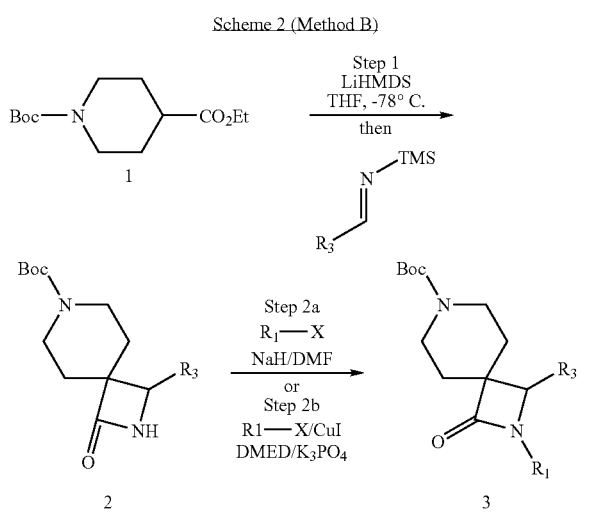

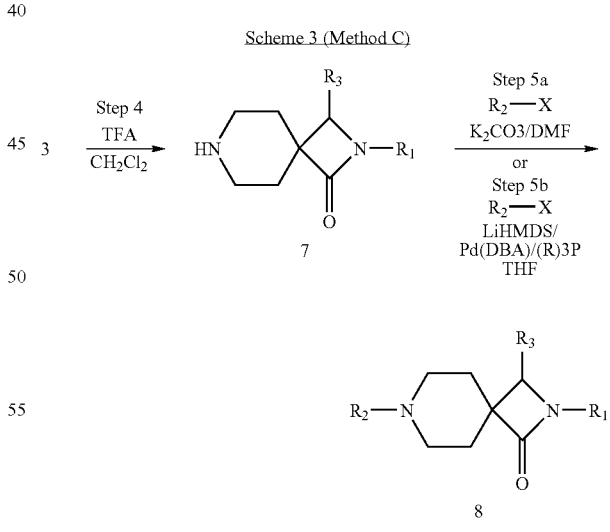

Additionally, compounds of formula 3 (see Scheme 2) can be converted into compounds 7 by the conditions of Step 4 in Method B which in turn can be subjected to the reaction conditions of Step 5 in Method B to yield compounds of formula 8 as shown in the Scheme 3 below.

Additional examples of this invention can be prepared according to the procedures outlined in Scheme 4. Accordingly, treatment of the amine 5.1 with a cyclobutene dione derivative such as 5a provides compounds such as 6.1. Subsequent treatment with another amine (NH($R^B$)$_2$) under basic conditions will provide compounds such as 7.1.

Scheme 4

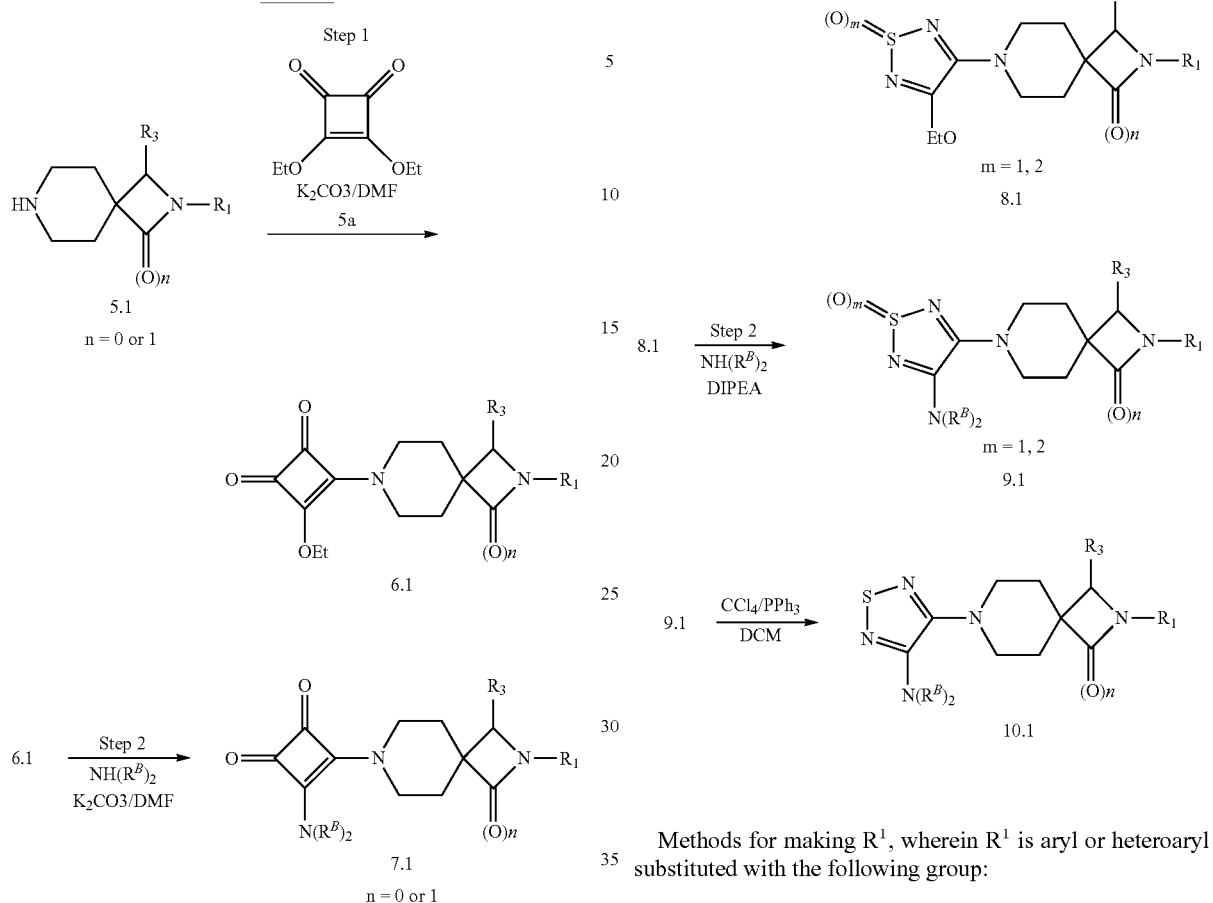

Further examples of this invention can be prepared according to the procedures outlined in Scheme 5. Accordingly, treatment of the amine 5.1 with a thiadiazole compound such as 5b provides compounds such as 8.1. Subsequent treatment with another amine ($NH(R^B)_2$) under basic conditions will provide compounds such as 9.1. Compounds 9.1 can be converted into compounds 10.1 by treatment with $CCl_4/PPh_3$.

Scheme 5

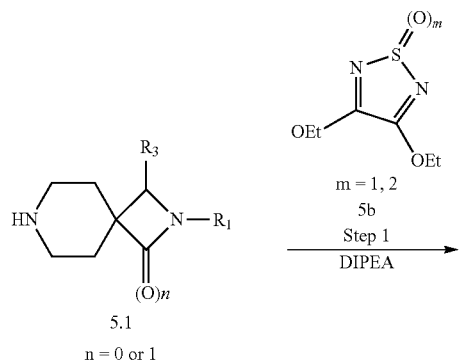

Methods for making $R^1$, wherein $R^1$ is aryl or heteroaryl substituted with the following group:

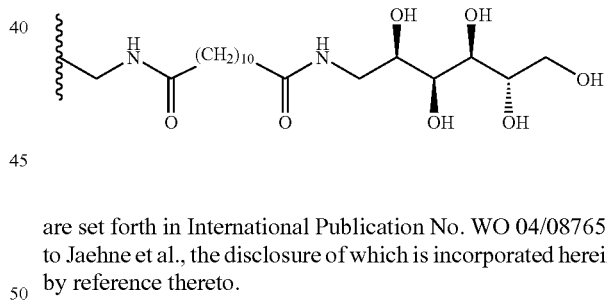

are set forth in International Publication No. WO 04/087655 to Jaehne et al., the disclosure of which is incorporated herein by reference thereto.

Methods for making the $R^1$, wherein $R^1$ is aryl or heteroaryl substituted with the following group:

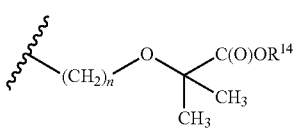

are set forth in International Publication No. WO 05/000353 to Tomiyama et al., the disclosure of which is incorporated herein by reference thereto.

Methods for making $R^1$, when $R^1$ is aryl or heteroaryl substituted with the following group:

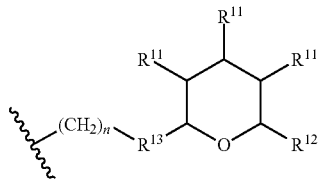

are set forth in International Publication No. WO 05/000353 to Tomiyama et al.

Methods for making $R^1$, when $R^1$ is aryl or heteroaryl substituted with the following group:

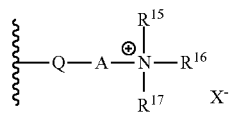

are set forth in International Publication No. WO 05/021495 to Martinez et al., the disclosure of which is incorporated herein by reference thereto. Methods for making $R^1$, wherein $R^1$ is biaryl or substituted biaryl, are set forth in International Publication No. WO 05/047248 to Martinez et al., the disclosure of which is incorporated herein by reference thereto.

Methods for making $R^3$, wherein $R^3$ is -phenyl substituted with the following group:

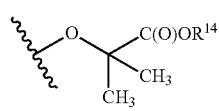

are set forth in International Publication No. WO 05/000353 to Tomiyama et al.

Methods for making $R^3$, wherein $R^3$ is -phenyl substituted with the following group:

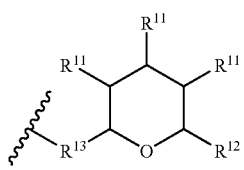

are set forth in International Publication No. WO 05/000353 to Tomiyama et al.

Methods for making $R^3$, wherein $R^3$ is -phenyl substituted with the following group:

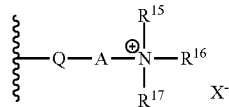

are set forth in International Publication No. WO 05/021495 to Martinez et al.

Methods for making $R^3$, wherein $R^3$ is -phenyl substituted with the following group:

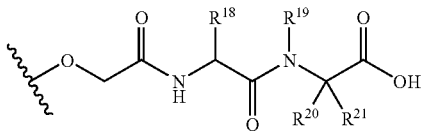

are set forth in International Publication No. WO 05/061452 to Alenfalk et al., the disclosure of which is incorporated herein by reference thereto.

Those skilled in the art will appreciate that replacing the starting materials (e.g., A4 in Method A and Compound 1 in Method B) with rings of different sizes will provide access to compounds such as:

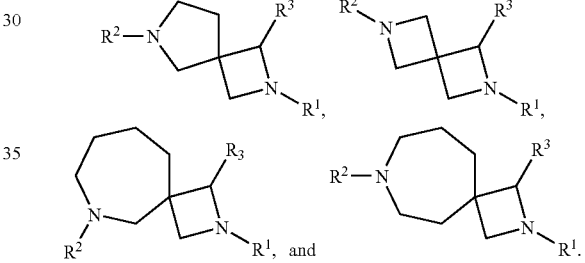

EXAMPLES 1 to 3

The compounds in Examples 1 to 3 could be prepared if one were to follow the procedures in Examples 1 to 3

EXAMPLE 1

Preparation of Dodecanedioic acid 4-[2-(3-chloro-4-fluoro-phenyl)-7-(5-fluoro-6-trifluoromethyl-1H-benzoimidazol-2-yl)-3-oxo-2,7-diaza-spiro[3.5]non-1-yl]-benzylamide (2,3,4,5,6-pentahydroxy-hexyl)-amide

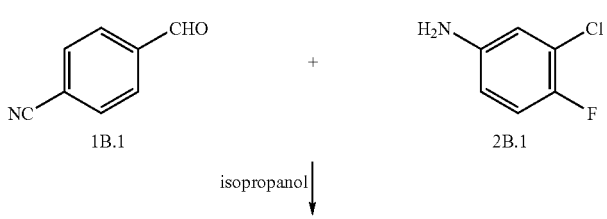

-continued
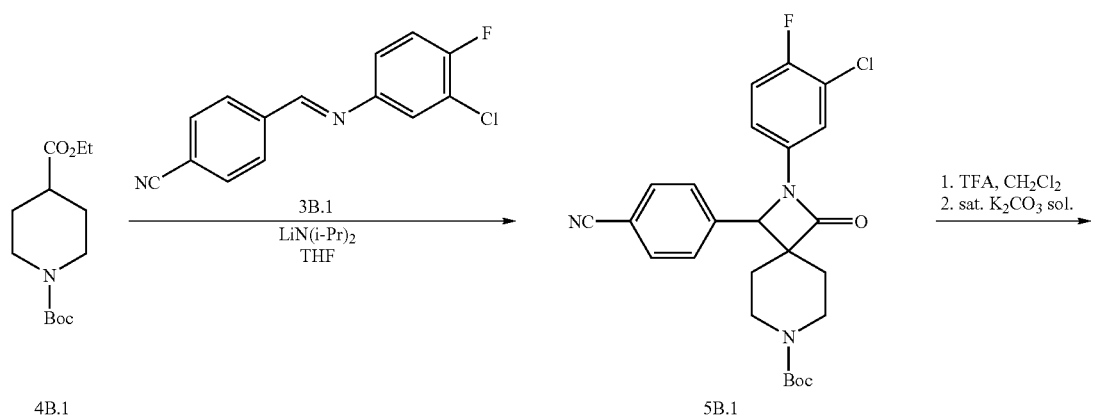
4B.1    5B.1
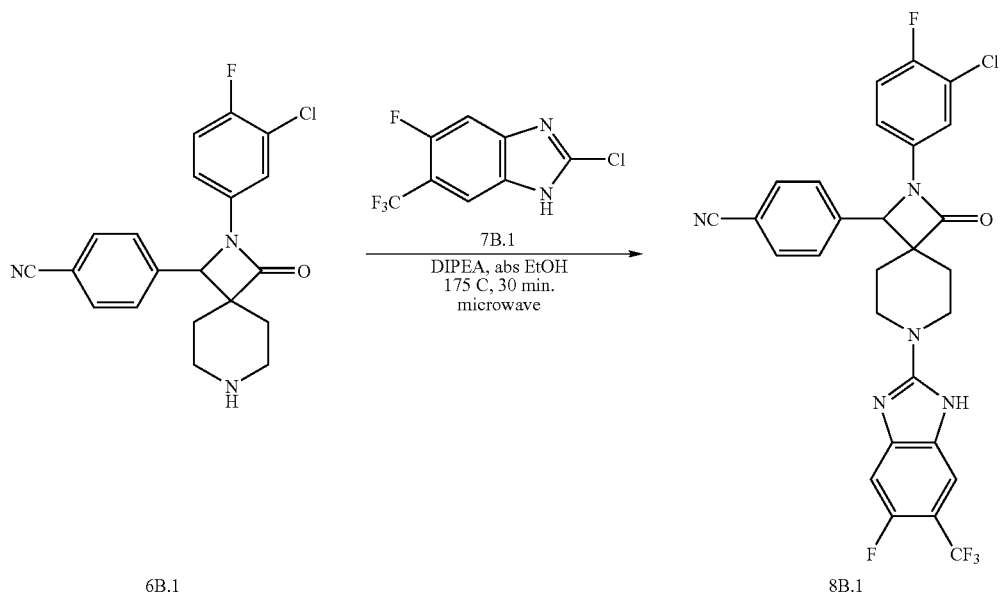
6B.1    8B.1
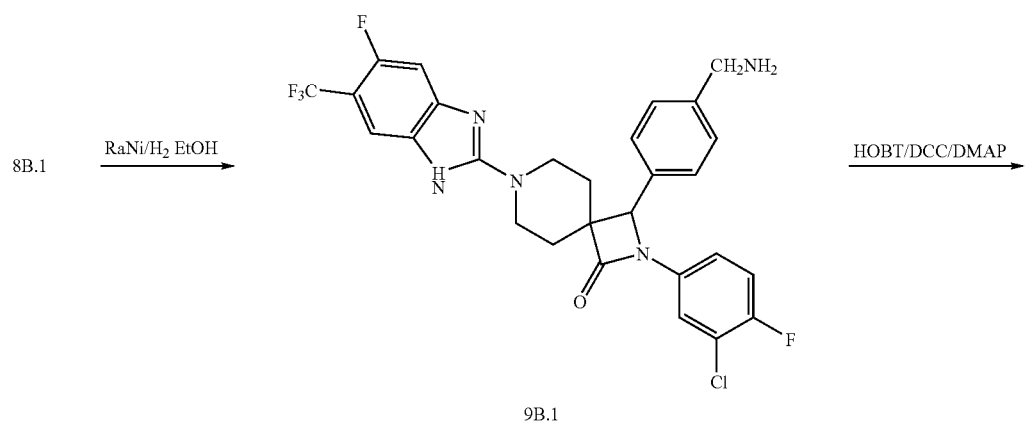
9B.1

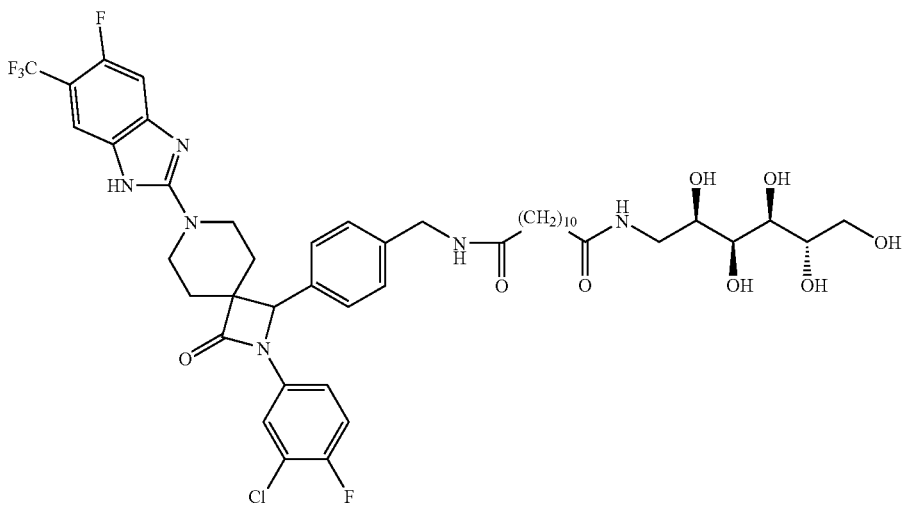

10B.1

Treat compound 4B.1 with 2 equivalents of LDA in THF and add to this after 30 minutes, the imine prepared from p-cyanobenzaldehyde and 2-chloro-4-fluoroaniline to obtain compound 5B.1. Treat 5B.1 with TFA in DCM at rt to remove the Boc protecting group. After evaporating to dryness, treat the residue with saturated K2Co3 and DCM to prepare compound 6B.1 as the free base. Reaction of 6B.1 with the 2-chlorobenzimidazole 7B.1 in the presence of DIPEA in ethanol with heating in a microwave to 175 C will provide the compound 8B.1 which is subjected to Raney to Nickel reduction over hydrogen to provide the aminomethyl compound 9B.1.

Treatment of this with the appropriate acid under standard peptide coupling conditions using HOBT and DCC will provide the title compound 10B.1

EXAMPLE 2

Preparation of 7-(5-Chloro-1H-benzoimidazol-2-yl)-2-(4-fluoro-phenyl)-3-{4-[2-(3,4,5-trihydroxy-6-hydroxymethyl-tetrahydro-pyran-2-yl)-ethyl]-phenyl}-2,7-diaza-spiro[3.5]nonan-1-one

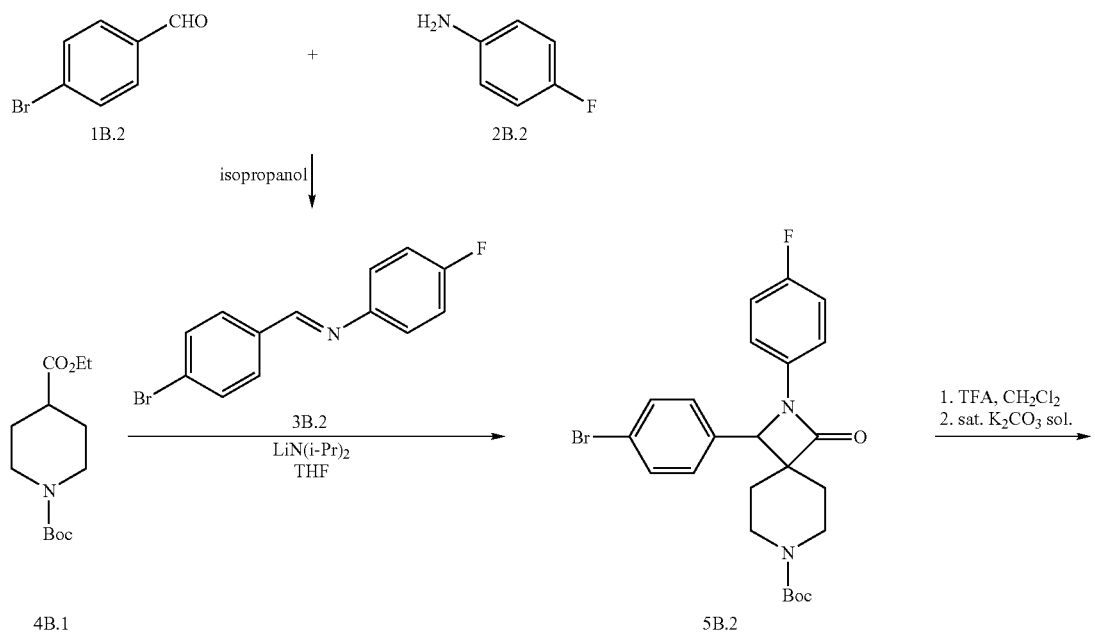

-continued
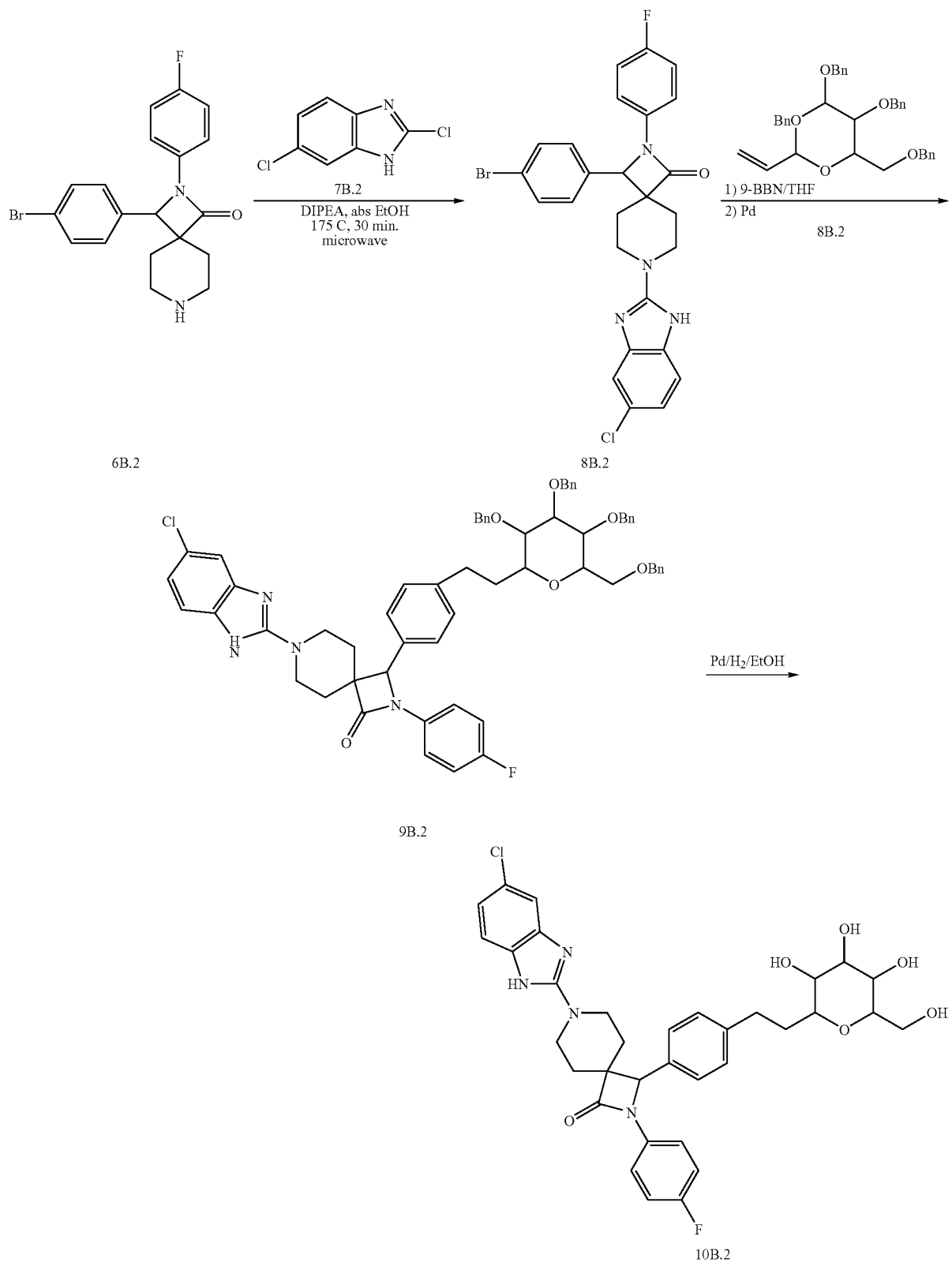
Treat compound 4B.1 with 2 equivalents of LDA or LiHMDS in THF and add to this, after 30 minutes, the imine prepared from p-bromobenzaldehyde and 4-fluoroaniline to obtain compound 5B.2. Treat 5B.2 with TFA in DCM at rt to remove the Boc protecting group. After evaporating to dryness, treat the residue with saturated $K_2CO_3$ and DCM to prepare compound 6B.2 as the free base. Reaction of 6B.2 with the 2-chlorobenzimidazole 7B.2 in the presence of DIPEA in ethanol with heating in a microwave to 175 C. will provide the compound 8B.2 which can be treated with the borane reagent prepared from reaction of 9-BBN with 3,4,5-Tris-benzyloxy-2-benzyloxymethyl-6-vinyl-tetrahydro-pyran (see Xie, et al. Journal of Organic Chemistry (2003), 68(20), 7896-7898). under palladium catalysis to give compound 9B.2. Removal of the protecting groups by hydrogenation or reaction with HBr in acetic acid will provide the title compound 10B.2

EXAMPLE 3

Preparation of 2-{4-[7-(5-Chloro-1H-benzoimidazol-2-yl)-2-(4-fluoro-phenyl)-2,7-diaza-spiro[3.5]non-1-yl]-benzyl}-6-hydroxymethyl-tetrahydro-pyran-3,4,5-triol

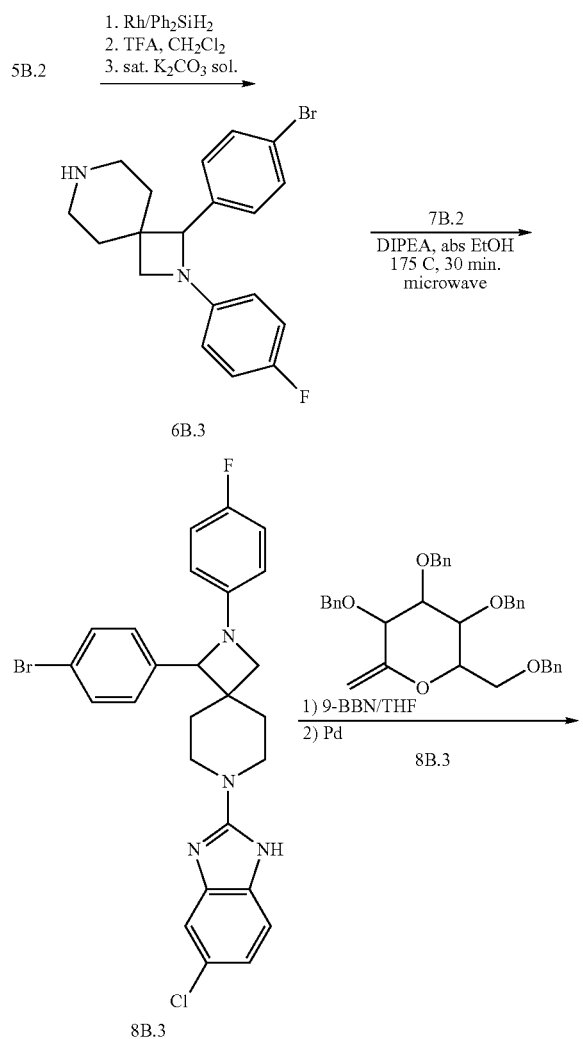

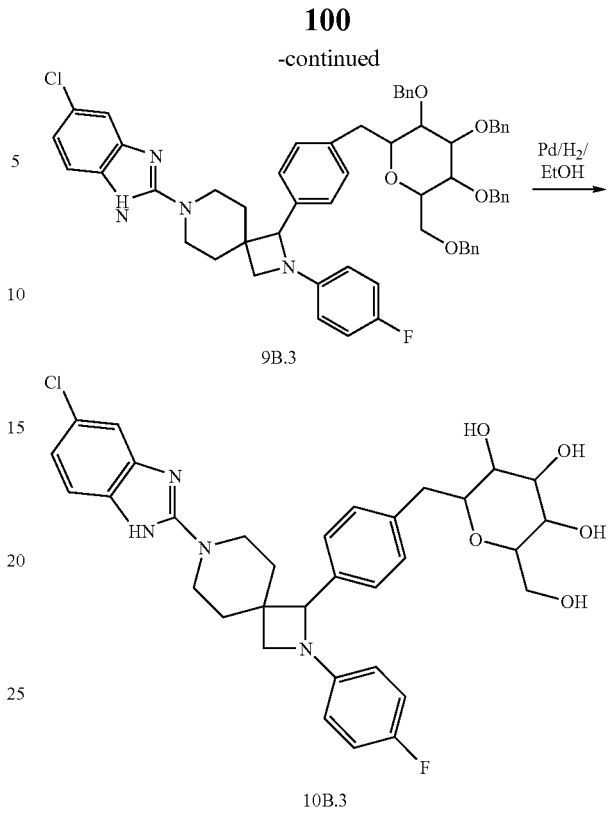

Treat compound 5B.2 with a mixture of diphenylsilane and hydridocarbonyltris(triphenylphosphine) rhodium to reduce the amide carbonyl, and treat this product with TFA in DCM at rt to remove the Boc protecting group. After evaporating to dryness, treat the residue with saturated $K_2CO_3$ and DCM to prepare compound 6B.3 as the free base. Reaction of 6B.3 with the 2-chlorobenzimidazole 7B.2 in the presence of DIPEA in ethanol with heating in a microwave to 175 C. will provide the compound 8B.3. Treatment of this material with the borane reagent prepared by treatment of 9-BBN with 3,4,5-Tris-benzyloxy-2-benzyloxymethyl-6-methylene-tetrahydro-pyran will provide compound 9B.3 (see conditions given in Walker, et al Bioorganic & Medicinal Chemistry Letters (2002), 12(17), 2447-2450) Removal of the protecting groups by hydrogenation over Pd or reaction with HBr in acetic acid at elevated temperatures will provide the title compound 10B.3.

Assays

Methods for Evaluating Functional Effects on Ion Channels

Functional evaluation of voltage-gated ion channels can be used to determine potency and/or single concentration efficacy of proprietary compounds. Two different methodologies can be used to measure ion currents: the IonWorks HT (Molecular Devices, Sunnyvale, Calif.) a moderate throughput voltage clamp screening platform that utilizes 96-well compound plates and conventional whole cell patch clamp for lower throughput, higher fidelity determinations.

Cell Lines

HEK cells can be transiently transfected and then selected for stable heterologous expression of different channel proteins of interest. Calcium channel cell lines expressed a resting potassium current, human $K_{ir}2.1$, and the pore forming α-subunit of voltage-gated calcium channels, In the case of $Ca_v2.1$ cells the auxiliary subunit, $β_2a$, can also be expressed.

Calcium channel lines that can be used to generate the data express either human $Ca_v3.2$, rat $Ca_v3.2$ or human $Ca_v2.1$. The human heart sodium channel, $hNa_v1.5$, can be stably expressed in CHO cells. These cells can be licensed from the University of Pennsylvania.

Cell lines were grown at 37° C. in humidified incubators, equilibrated with 95% air/5% $CO_2$. CHO cells can be grown in Ham's F-12 medium HEK cells can be grown in DMEM. All media can be supplemented with 10% heat-inactivated fetal bovine serum, penicillin, streptomycin and appropriate selection antibiotics (zeocin, geneticin and/or hygromycin). Cells can be passaged when 80% confluent or less.

IonWorks Screen for hCaV3.2

The extracellular buffer for experiments using this instrument contains the following (mM) (NaCl 125, HEPES 10, KCl 5.4, $CaCl_2$ 1.8, $MgCl_2$ 1.8, 0.2 $BaCl_2$ pH 7.35). The Ionworks uses amphotericin to gain electrical access to the cell interior. The internal solution contains (mM concentrations): 130 K-gluconate, 20 KCl, 5 HEPES-KOH (pH 7.25), 2 $CaCl_2$, 1 $MgCl_2$. Amphotericin can be added at 5 mg in 65 ml when present (in 650 μl DMSO). All internal and external solutions for this experiment contain 1% DMSO. Cells can be acutely trypsinized from a T-75 flask and can be resuspended in extracellular buffer at a density of $2 \times 10^5$ cells/ml.

Experiments can be performed at room temperature. Transmembrane potential can be held at −100 mV for 5 seconds prior to running the voltage protocol. During this time leak currents can be measured during a step to −110 mV (200 milliseconds). T-type calcium currents can be activated with a 250 millisecond step to −20 mV. This depolarization step can be repeated for a total of 10 pulses with an interpulse interval of 1 second. Data can be excluded if the following acceptance criteria are not met: total resistance for the pre-compound scan >65 MΩ, pre-compound current >250 pA, post compound total resistance >50 MΩ.

T-type currents can be measured as the peak inward current minus the current at the end of the 250 msec step to −20 mV. After the recoding configuration is established there can be a pre-compound measurement of current amplitude. Compound can be added as a 3× solution containing 1% DMSO. After incubation with compound for 10 minutes currents can be measured again. The current amplitude after compound addition is divided by the pre-compound current for pulse 10 to determine the fraction of current remaining after compound addition. For each compound, 8-point concentration-effect relationships can be measured with ½ log serial dilutions. These data can then be transferred into GraphPad Prism (v 4) and non-linear regression analysis can be used to estimate the $IC_{50}$ for each test compound.

Conventional Whole Cell Patch Clamp

Cells can be plated onto 9 mm diameter circular coverglass in the appropriate growth medium and placed in a 37° C. incubator until use. Whole cell patch clamp studies can be conducted at room temperature using conventional methods. PCLAMP software (v8 or 9) can be used in conjunction with a compatible A/D D/A board, a Pentium III personal computer and either a Multiclamp 700 or an AxoPatch 1D amplifier can be used to generate voltage clamp protocols, acquire data and measure currents.

At the time of study, a piece of coverglass with attached cells can be transferred to a recording chamber on the stage of an inverted microscope and the whole cell configuration of patch clamp can be established. The recording chamber can be gravity perfused with extracellular solution at a flow rate of approximately 3 ml/mm Patch electrodes have resistances of 2-3 MΩ when filled with pipette solution. The extracellular solution is a HEPES-buffered saline (149 NaCl, 10 HEPES-NaOH (pH 7.4), 10 glucose, 5 CaCl2 , $MgCl_2$, 5 $CaCl_2$; concentrations in mM). The pipette solution contains (mM concentrations) 115 CsCl, 10 HEPES-CsOH (pH 7.3), 4 MgATP, 10 EGTA; osmolarity to 310 mM with sucrose). All solutions contain 0.1% DMSO.

The holding potential can be −100 mV for all protocols. Interpulse interval can be 15 seconds. The time course of $hCa_v3.2$ or $rCa_v3.2$ current can be examined with a 200 millisecond test pulse to −35 mV. $Ca_v3.2$ currents can be measured as the peak current 10-30 milliseconds after the voltage is stepped to −35 mV. P/N 4 leak subtraction can be used. The amplifier low pass filter can be set to 10 kHz and the data can be sampled at 10 kHz, Data can be filtered offline with a Gaussian filter with a −3 dB cutoff of 280 Hz. The voltage protocol for hCaV2.1 currents differ only in terms of the voltage for the depolarizing test potential. For $hCa_v2.1$ currents can be activated with a 200 millisecond step to 0 mV. $hCa_v2.1$ currents can be measured from the leak-subtracted traces as the average current between 190 and 200 milliseconds after the step to 0 mV. The voltage protocol for sodium currents includes a 150 millisecond hyperpolarizing pulse to −140 mV to optimize channel availability, followed by a 20 millisecond test pulse to −20 mV. Sodium currents can be measured from leak subtracted traces as the peak transient inward current.

All drug effects can be measured after a steady-state effect is achieved. Concentration-effect relationships can be derived by exposing each cell to only a single concentration of test article. For non-linear regression analysis the post-compound current amplitude can be normalized to the pre-compound current amplitude for each cell. If a given current is inhibited by >50% at a concentration of 10 μM or less, the data for multiple concentrations of compound and corresponding vehicle and time control cells can be entered into GraphPad Prism (v 4) for non-linear regression analysis to determine the $IC_{50}$.

The actions of the compounds of formula I for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection) the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neuropathic pain model): The peripheral neuropathy is produced by ligating the L5 and L6 spinal nerves of the right sciatic nerve, based on the method previously of Kim and Chung (1992). Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In the POST-TREATMENT protocol, rats are tested 3 hours after carrageenan treatment to establish the presence of hyperalgesia and then at different times after drug administration. In the PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioral test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioral test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioral test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

To Measure NPC1L1 The Following Binding Assays Would Be Used:

HEK-293 cells expressing human NPC1L1 can be plated into 384-well black/clear plates (BD Biosciences, Bedford Mass.) for binding experiments the following day. Cell growth media (DMEM, 10% fetal calf serum, 1 mg/ml geneticin, 100 Units/ml penicillin) can be aspirated. Cell growth media (20 ml) containing 250 nM BODIPY-labeled glucuronidated ezetimibe can be added to each well. Cell growth media (20 ml) containing the indicated concentration of compound can then be added to the wells. Unlabeled glucuronidated ezetimibe (100 mM) can be used to determine nonspecific binding. The binding reaction can be allowed to proceed for 4 h at 37 C. Subsequently the cell growth media can be aspirated and the cells can be washed once with PBS. The remaining fluorescent labeled glucuronidated ezetimibe bound to the cells can be quantified using a FlexStation plate reader (Molecular Devices, Sunnyvale Calif.) to measure fluorescence intensity. Ki values can be determined from competition binding curves (n=4 for each point) using Prism and Activity Base software.

To Measure Inhibition of Cholesterol Absorption The Following In Vivo Assay Would Be Used:

Male rats can be dosed by oral gavage with 0.25 ml corn oil or compound in corn oil; 0.5 h later, each rat can be given 0.25 ml of corn oil orally with 2 μCi $^{14}$C-Cholesterol, 1.0 mg cold cholesterol.

2 h later, the rats can be anesthetized with 100 mg/kg IP of Inactin, and a 10 ml blood sample can be collected from the abdominal aorta. The small intestine can be removed, divided into 3 sections, and each rinsed with 15 ml of cold saline. The rinses can be pooled. The liver can be removed, weighed, and three ~350 mg aliquots csn be removed. 5ml 1 N NaOH can be added to each intestinal piece, 1 ml to each liver aliquot to dissolve at 40° overnight. 2×1 ml aliquots of the SI digests and the liver digests can be neutralized with 0.25 ml 4N HCl and counted. 2×1 ml aliquots of plasma and intestinal rinses can be counted.

Embodiments of this invention include those in paragraphs:

1. Compounds of formula (I);
2. The compound as described in paragraph (1.) wherein $R^1$ is selected from the group consisting of: —H, -phenyl, -phenyl substituted with -alkyl, -phenyl substituted with -halo, -phenyl substituted with —NO$_2$, -phenyl substituted with —OH, -phenyl substituted with —C(O)OH, -phenyl substituted with —O-alkyl, -phenyl substituted with —CF$_3$, phenyl which is fused to a heteroaryl ring, phenyl which is fused to a heterocycloalkyl ring, pyridyl, -2-pyridyl, -benzyl, and -4-fluorophenyl;
3. The compound as described in paragraph (1) wherein $R^1$ is selected from the group consisting of: benzofuranyl, indazolyl, benzothiazolyl, benzofuranyl substituted with a —COOH or a —CH$_2$COOH group, indazolyl substituted with a —COOH or a —CH$_2$COOH group, benzothiazolyl substituted with a —COOH or a —CH$_2$COOH group,
4. The compound as described in paragraph (1.) wherein $R^1$ is:

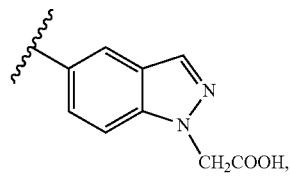

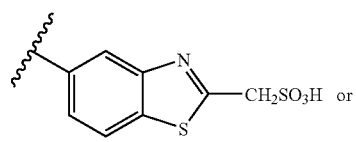

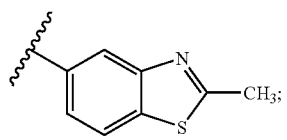

5. The compound as described in paragraph (1.) wherein $R^1$ is selected from the group consisting of:

(a) -heteroaryl,

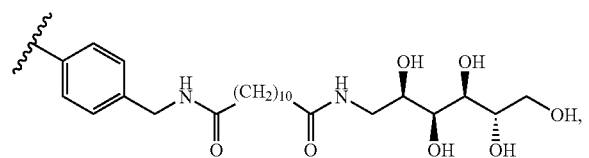

(b) —$(CH_2)_n$-phenyl wherein the phenyl group is substituted with

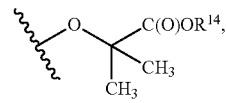

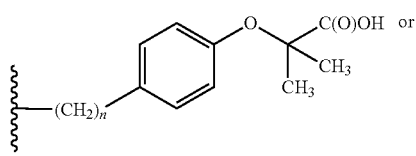

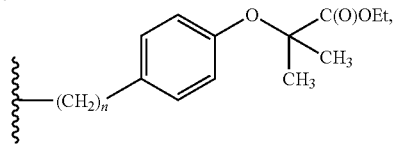

(c) —$(CH_2)_n$-phenyl, wherein the phenyl group is substituted with

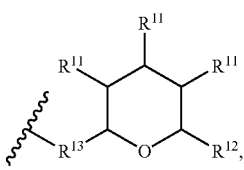

(d) —$(CH_2)_n$-phenyl, wherein the phenyl group is substituted with

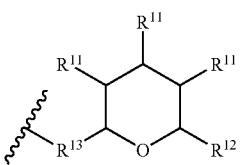

wherein $R^{13}$ is -absent, each occurrence of $R^{11}$ is —OH or —OAc, and $R^{12}$ is —$CH_2OH$ or —$CH_2OAc$, (e) —$(CH_2)_n$-phenyl, wherein the phenyl group is substituted with

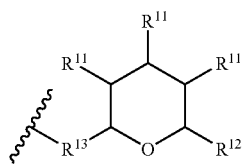

wherein $R^{13}$ is -alkylene-, -oxaalkylene- or -alkenylene-, each occurrence of $R^{11}$ is —OH or —OAc, and $R^{12}$ is —$CH_2OH$ or —$CH_2OAc$, (f)

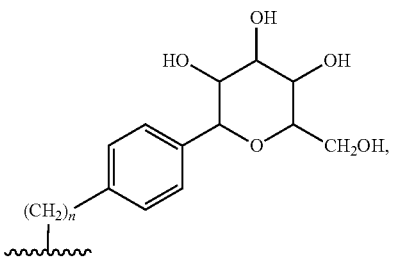

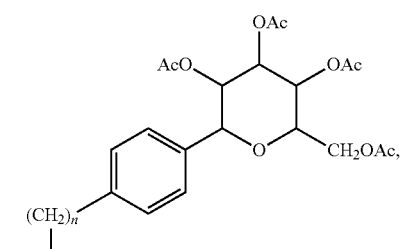

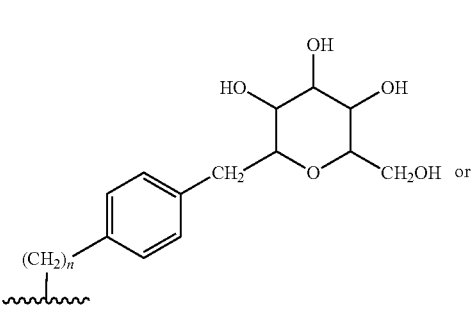

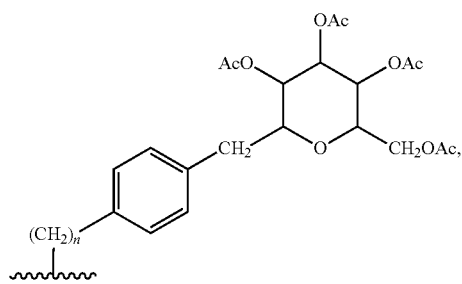

(g) -phenyl which is substituted with

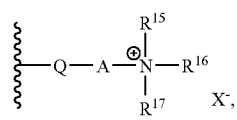

(h)

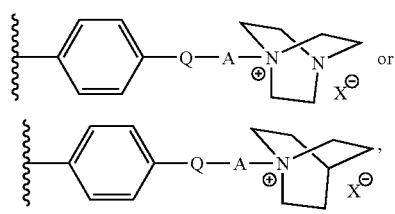

(i)

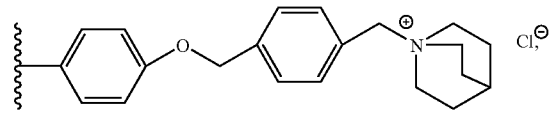

(j) phenyl which is substituted with —C≡C—CH$_2$NR$^{14}$R$^{24}$, —C≡C—CH$_2$C(O)OR$^{25}$ or -alkylene-NR$^{14}$R$^{26}$, and (k) —OR$^{23}$;

6. The compound as described in paragraph (1.) wherein R$^3$ is selected from the group consisting of:

(a) —H, (b) is aryl, (c) phenyl substituted with —F, —Br or —I, (d) phenyl substituted with —OH.

(e) phenyl substituted with —OCH$_3$.

(f) heteroaryl.

(g)

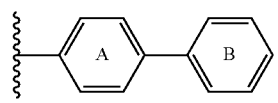

wherein each of rings A and B may be optionally and independently substituted with 1-5 groups selected from -halo, —OH, -alkyl, -alkoxy, —SH, -thioalkyl, —N(R$^{14}$)$_2$, —NO$_2$, —CN, —CF$_3$, —OC(O)R$^{14}$, —OC(O)—R$^{14}$, —C(O)OR$^{14}$, —C(O)O—R$^{14}$, R$^6$-aryl-, R$^7$, R$^8$, R$^9$ or R$^{10}$, (h)

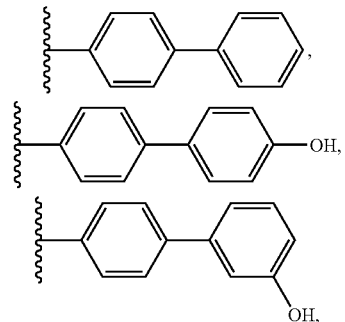

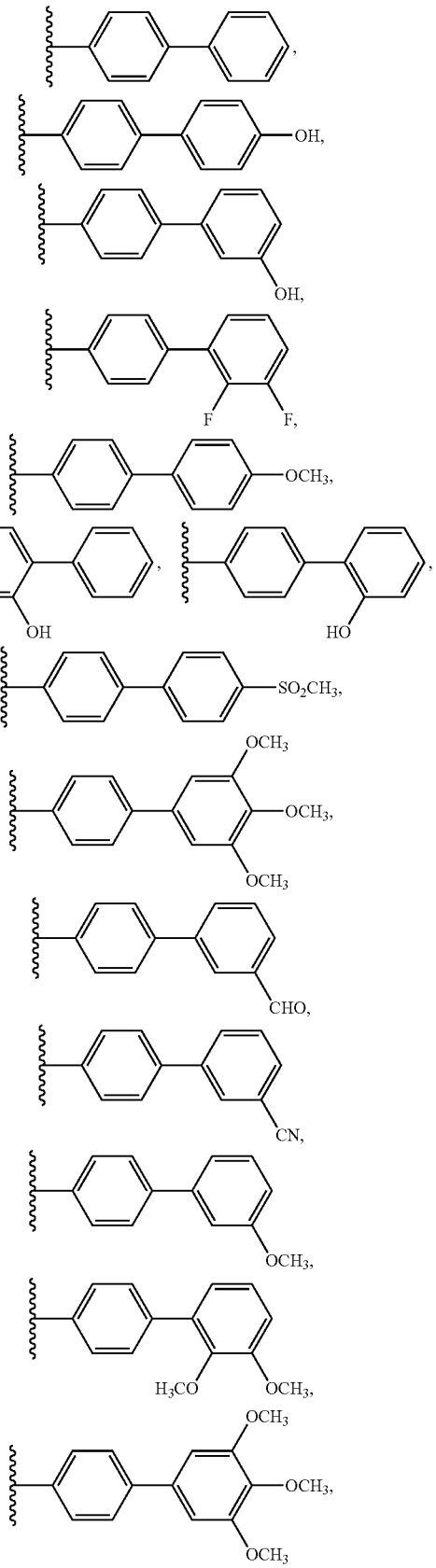

-continued
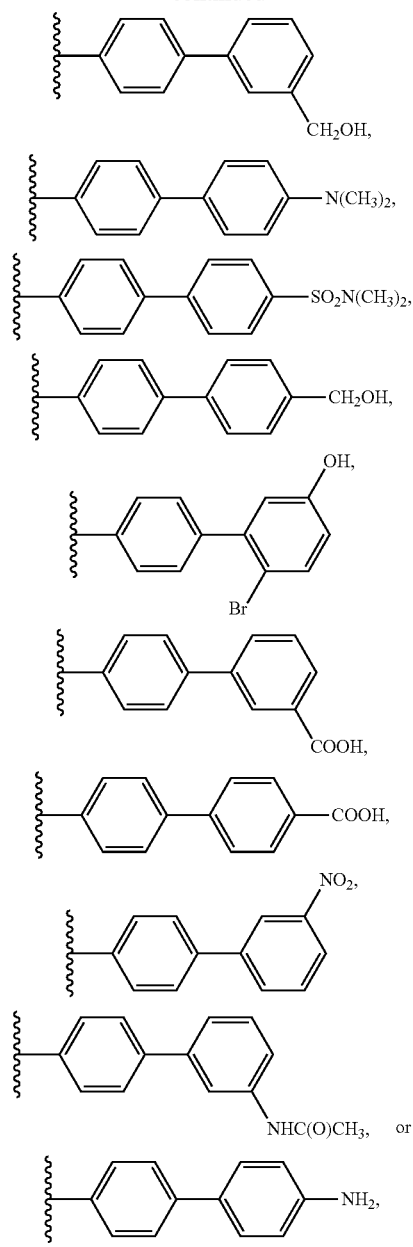
(i)-phenyl which is substituted with
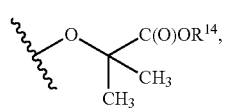
(j)
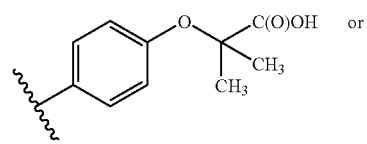
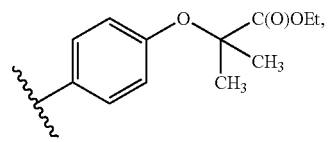
-continued
(k)-phenyl which is substituted with
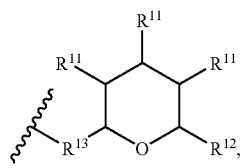
(l)
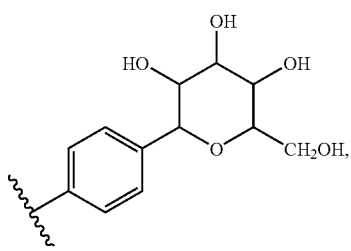
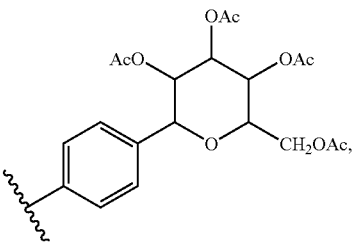
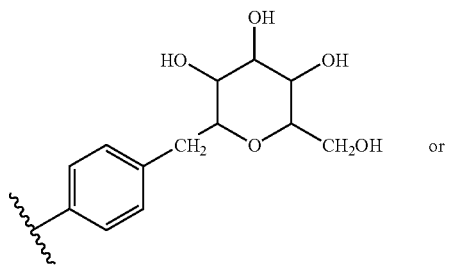
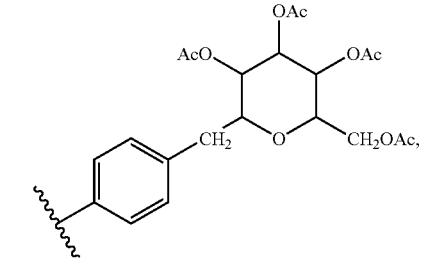
(m)-phenyl which is substituted with
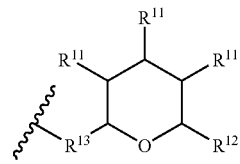
(j)
wherein $R^{13}$ is -alkylene-, -oxaalkylene- or -alkenylene-, each occurrence of $R^{11}$ is —OH or —OAc, and $R^{12}$ is —CH$_2$OH or —CH$_2$OAc, (n) -phenyl which is substituted with

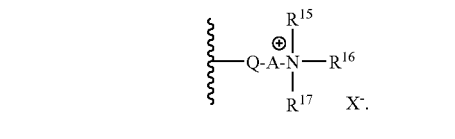

(o)

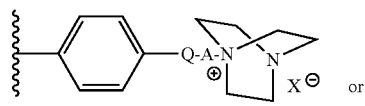

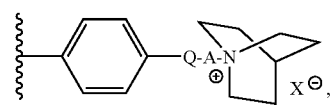

(p)

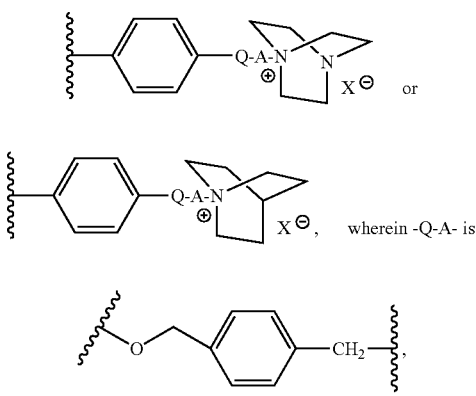

wherein -Q-A- is

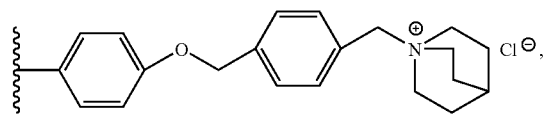

(q)

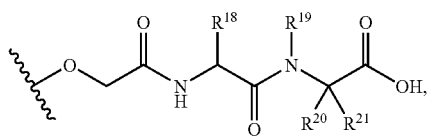

(r)

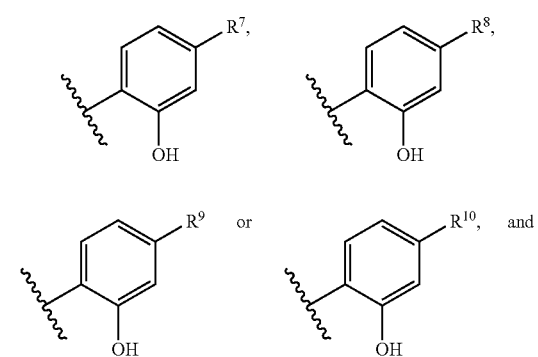

(s)

(t) phenyl which is substituted with

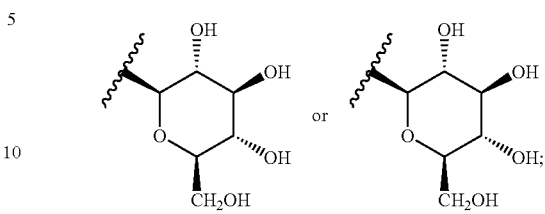

7. The compound as described in paragraph (1.) wherein $R^3$ is selected from the group consisting of: phenyl substituted with —F and phenyl substituted with —Br;

8. The compound as described in paragraph (1.) wherein $R^2$ is selected from the group consisting of: pyridyl, pyrimidinyl, and benzolmidazolyl-;

9. The compound as described in paragraph (1.) having the formula:

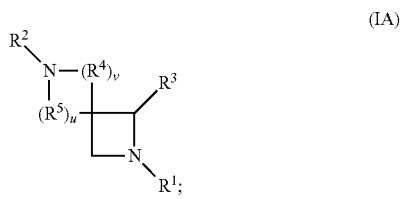

(IA)

10. The compound as described in paragraph (1.) having the formula:

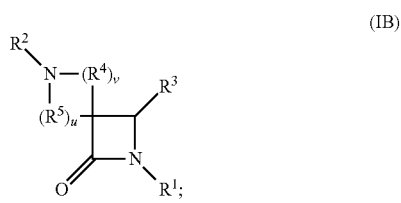

(IB)

11. The compound as described in paragraph (1.) having the formula:

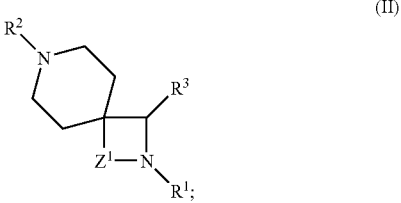

(II)

12. The compound as described in paragraph (1.) having the formula

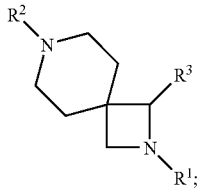

(IIA)

13. The compound as described in paragraph (1.) having the formula

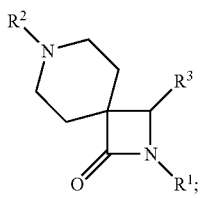

(IIB)

14. The compound as described in paragraph (1.) wherein: $R^2$ is selected from the group consisting of: (A) heteroaryl; and (B) substituted heteroaryl;

15. The compound as described in paragraph (14.) wherein: $R^2$ is selected from the group consisting of: pyridyl, pyrimidinyl, pyrazinyl, benzoimidazolyl-, quinazolinyl, isoquinolinyl, quinolinyl, substituted pyridyl, substituted pyrimidinyl, substituted pyrazinyl, substituted benzoimidazolyl, substituted quinazolinyl, substituted isoquinolinyl, and substituted quinolinyl; and wherein said substituted groups are substituted with 1 to 3 substituents independently selected from the group consisting of: alkyl, halo, CN, —$CF_3$, alkoxy, halo substituted alkoxy, cycloalkyl, and halo substituted alkyl;

16. The compound as described in paragraph (15.) wherein said substituents on said substituted groups are selected from the group consisting of: Cl, F, Br, —$CF_3$, —$OCH_3$, cyclopropyl, —$OCF_3$, —$CF_2CH_3$ and —CN;

17. The compound as described in paragraph (1.) wherein $R^2$ is selected from the group consisting of:

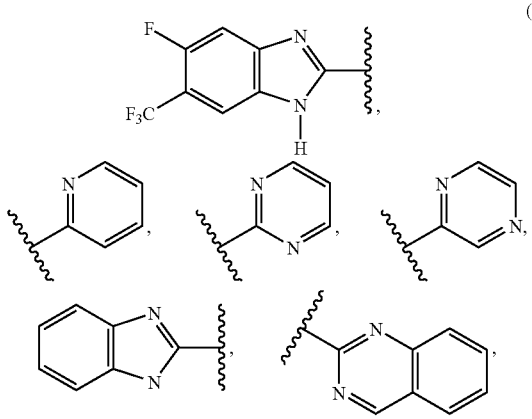

(k3)

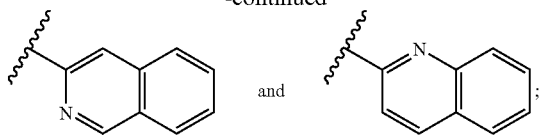

18. A pharmaceutical composition comprising an effective amount of at least one compound as described in paragraph (1.) and a pharmaceutically acceptable carrier;

19. A method of treating pain comprising administering to a patient in need of such treatment an effective amount of at least one compound as described in paragraph (1.);

20. The method as described in paragraph (19.) wherein said pain is selected from the group consisting of: inflammatory pain, chronic and neuropathic pain;

21. A method of treating pain comprising administering to a patient in need of such treatment an effective amount of a combination of at least one compound as described in paragraph (1.) and at least one additional agent for treating pain;

22. The method as described in paragraph (21.) wherein said additional agent for treating pain is selected from the group consisting of: non-opioid analgesics and opioid analgesics;

23. The method as described in paragraph (21.) wherein said additional agent for treating pain is selected from the group consisting of: corticosteroids, non-sterodial anti-inflammatory agents, COX-I and COX-II inhibitors, agents useful for treating inflammatory bowel disease and agents useful for treating rheumatoid arthritis;

24. The method as described in paragraph (21.) wherein said additional agent for treating pain is selected from the group consisting of:
(A) non-opioid analgesics selected from the group consisting of: acetylsalicylic acid, choline magnesium trisalicylate, acetaminophen, ibuprofen, fenoprofen, diflusinal, and naproxen;
(B) opioid analgesics selected from the group consisting of: morphine, hydromorphone, methadone, levorphanol, fentanyl, oxycodone, and oxymorphone;
(C) steroids selected from the group consisting of: prednisolone, fluticasone, triamcinolone, beclomethasone, mometasone, budisamide, betamethasone, dexamethasone, prednisone, flunisolide and cortisone;
(D) COX-I inhibitors selected from the group consisting of: aspirin and piroxicam;
(E) COX-II inhibitors selected from the group consisting of: rofecoxib, celecoxib, vaidecoxib and etoricoxib;
(F) agents useful for treating inflammatory bowel disease selected from the group consisting of: IL-10, steroids, and azulfidine; and
(G) agents useful for treating rheumatoid arthritis selected from the group consisting of: methotrexate, azathioprine, cyclophosphamide, steroids and mycophenolate mofetil;

25. The method as described in paragraph (21.) wherein said additional agent for treating pain is selected from the group consisting of: acetylsalicylic acid, choline magnesium trisalicylate, acetaminophen, ibuprofen, fenoprofen, diflusinal, naproxen, morphine, hydromorphone, methadone, levosrphanol, fentanyl, oxycodone, and oxymorphone;

26. The method as described in paragraph (21.) wherein said additional agent for treating pain is selected from the group consisting of:
(A) steroids selected from the group consisting of: prednisolone, fluticasone, triamcinolone, beclomethasone, mometasone, budisamide, betamethasone, dexamethasone, prednisone, flunisolide and cortisone; and (B) non-opioid analgesics selected from the group consisting of: acetylsalicylic acid, choline magnesium trisalicylate, acetaminophen, ibuprofen, fenoprofen, diflusinal, and naproxen;

27. A method for inhibiting the absorption of cholesterol comprising administering to a patient in need of such treatment an effective amount of at least one compound as described in paragraph (1.);

28. A method for inhibiting the absorption of cholesterol comprising administering to a patient in need of such treatment an effective amount of at least one compound as described in paragraph (1.) in combination with an effective amount of at least one additional agent for treating a disorder of lipid metabolism;

29. A method for inhibiting the absorption of cholesterol comprising administering to a patient in need of such treatment an effective amount of at least one compound as described in paragraph (1.) in combination with an effective amount of at least one nicotinic acid receptor agonist;

30. A method for inhibiting the absorption of cholesterol comprising administering to a patient in need of such treatment an effective amount of at least one compound as described in paragraph (1.) in combination with an effective amount of at least one inhibitor of HMG-CoA reductase;

31. A method for inhibiting the absorption of cholesterol comprising administering to a patient in need of such treatment an effective amount of at least one compound as described in paragraph (1.) in combination with an effective amount of at least one inhibitor of CETP;

32. A method for inhibiting the absorption of cholesterol comprising administering to a patient in need of such treatment an effective amount of at least one compound as described in paragraph (1.) in combination with an effective amount of at least one NPC1L1 antagonist;

33. A method for inhibiting the absorption of cholesterol comprising administering to a patient in need of such treatment an effective amount of at least one compound as described in paragraph (1.) in combination with an effective amount of at least one inhibitor of HMG-CoA reductase, and in combination with an effective amount of at least one NPC1L1 antagonist; and 34. The compound as described in paragraph (1.) in pure and isolated form.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

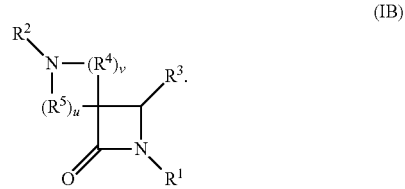

(IB)

or a pharmaceutically acceptable salt, ester, or stereoisomer thereof, wherein:

$Z^1$ is —C(O)—;

$R^1$ is -phenyl or -benzyl, wherein a phenyl group may be fused to a heteroaryl ring or a heterocycloalkyl ring, and wherein the phenyl group or phenyl ring of a benzyl group may be optionally and independently substituted with 1-5 groups selected from —$R^9$, —OH, —$CF_3$, —$OCF_3$, —$CHF_2$, —$OCHF_2$, —SH, —$NH_2$, —$NO_2$, —C(O)OH, -halo, -alkoxy, -alkyl, -alkylthio, —$CH_2NHC(O)(CH_2)_{10}C(O)NHCH_2$—$(CH(OH))_4$—$CH_2OH$, hydroxyalkyl, methylenedioxy, ethylenedioxy, —CN, —NH(alkyl), —N(alkyl)$_2$, —$SO_2NH_2$, —$SO_2NH(alkyl)$, —$SO_2N(alkyl)_2$, —$SO_2$-alkyl, —$SO_2$-aryl, -acyl, -alkoxycarbonyl, —C(O)$NH_2$, —S(O)—alkyl, —NHC(O)—alkyl, —C(=NH)$NH_2$, -phenyl, -benzyl, —O—phenyl, —C≡C—$CH_2NR^{14}R^{24}$, —C≡C—$CH_2C(O)OR^{25}$, -alkylene—$NR^{14}R^{26}$, —O-benzyl, —$PO_3H_2$, —$SO_3H$, —$B(OH)_2$, a sugar, a polyol, a glucuronide or a sugar carbamate; or $R^1$ is —$(CH_2)_n$-phenyl, wherein the phenyl group may be fused to a heteroaryl ring or a heterocycloalkyl ring and wherein the phenyl group may be optionally and independently substituted with 1-5 groups selected from —$R^7$, —$R^8$ or —$R^{11}$;

$R^2$ is selected from the group consisting of:
(1) heteroaryl,
(2) heterocycloalkenyl;
(3) substituted cyclobutenedione of the formula:

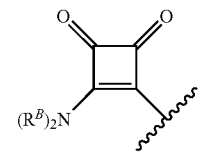

wherein each $R^B$ is independently selected from the group consisting of: H, alkyl, substituted alkyl, aryl, substituted aryl, heteroaryl and substituted heteroaryl, provided that at least one $R^B$ is other than H, and wherein the substituted alkyl moieties are each independently substituted with one or more substituents independently selected from the group consisting of: (a) —(C=N—O-alkyl)$CH_3$, (b) —NC(O)$NH_2$, (c) —NC(O)NH(alkyl), (d) —NC(O)N(alkyl)$_2$, (e) —$SO_2NH_2$, (f) —$SO_2NH(alkyl)$, (g) —$SO_2N(alkyl)_2$, (h) —$CF_3$, (i) —OH, (j) -halo, (k) —CN, (l) -alkoxy, (m) —C(O)O—alkyl, (n) —S(O)alkyl, (o) —$SO_2$-alkyl, and (p) —P(O)(O—alkyl)$_2$;

wherein the substituted aryl moieties are each independently substituted with one or more substituents independently selected from the group consisting of: (a) —(C=N—O—alkyl)$CH_3$, (b) —NC(O)$NH_2$, (c) —NC(O)NH(alkyl), (d) —NC(O)N(alkyl)$_2$, (e) —$SO_2NH_2$, (f) —$SO_2NH(alkyl)$, (g) —$SO_2N(alkyl)_2$, (h) —$CF_3$, (i) —OH, (j) -halo, (k) —CN, (l) -alkoxy, (m) —C(O)O—alkyl, (n) —S(O)alkyl, (o) —$SO_2$-alkyl, (p) —P(O)(O—alkyl)$_2$, and (q) alkyl; and wherein the substituted heteroaryl moieties are each independently substituted with one or more substituents independently selected from the group consisting of: (a) —(C=N—O—alkyl)$CH_3$, (b) —NC(O)$NH_2$, (c) —NC(O)NH(alkyl), (d) —NC(O)N(alkyl)$_2$, (e) —$SO_2NH_2$, (f) —$SO_2NH(alkyl)$, (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, and (p) —P(O)(O—alkyl)₂;

(4) thiadiazoles of the formula:

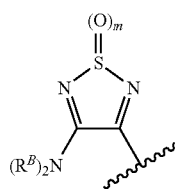

wherein each $R^B$ is independently selected from the group consisting of: H, alkyl, substituted alkyl, aryl, substituted aryl, heteroaryl and substituted heteroaryl, provided that at least one $R^B$ is other than H, and m is 0, 1 or 2, and wherein the substituted alkyl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, and (p) —P(O)(O—alkyl)₂;

wherein the substituted aryl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, (p) —P(O)(O—alkyl)₂, and (q) alkyl; and wherein the substituted heteroaryl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, (p) —P(O)(O—alkyl)₂, and (q) alkyl; and (5) substituted heteroaryl wherein the substituted heteroaryl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, (p) —P(O)(O—alkyl)₂, and (q) alkyl;

$R^3$ is -aryl or -heteroaryl, wherein an aryl group may be fused to a heteroaryl ring or a heterocycloalkyl ring and wherein the aryl group may be optionally and independently substituted with 1-5 groups selected from -halo, —OH, —OR²³, -alkyl, -alkoxy, —SH, —N(R¹⁴)₂, —NO₂, —CN, —CF₃, —OC(O)R¹⁴, —OC(O)—R¹⁴, —C(O)OR¹⁴, —C(O)O—R¹⁴, R⁶-aryl-, R⁷, R⁸, R⁹ or R¹⁰, and wherein a heteroaryl group may be optionally and independently substituted with one to five R⁶ groups, such that $R^3$ is not -2-pyridyl, -3-pyridyl, unsubstituted phenyl, or 4-chloro-phenyl;

Each occurrence of R⁴ is:
independently selected from the group consisting of: —CH₂—, —CH(alkyl)-, —C(alkyl)₂—, —C(O)—, —CH(substituted alkyl)-, —C(substituted alkyl)₂-, and each alkyl is independently selected, and each substituted alkyl is independently selected, and wherein the substituted alkyl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, and (p) —P(O)(O—alkyl)₂;

Each occurrence of R⁵ is:
independently selected from the group consisting of: —CH₂—, —CH(alkyl)—, —C(alkyl)₂—, —C(O)—, —CH(substituted alkyl)-, —C(substituted alkyl)₂-, and each alkyl is independently selected, and each substituted alkyl is independently selected, and wherein the substituted alkyl moieties are each independently substituted with one or more substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O—alkyl, (n) —S(O)alkyl, (o) —SO₂-alkyl, and (p) —P(O)(O—alkyl)₂; or R⁴ and R⁵ are as defined above, and one ring carbon of R⁴ and one ring carbon of R⁵ are bound together by a —CH₂—CH₂— group;

each occurrence of R⁶ is independently -halo, —OH, -alkyl, -alkoxy, —SH, -alkylthio, —NH₂, —NO₂, hydroxyalkyl, methylenedioxy, ethylenedioxy, —SO₂NH₂, —SO₂NH(alkyl), —SO₂N(alkyl)₂, —SO₂-alkyl, —SO₂-aryl, acyl, —C(O)OH, —C(O)O-alkyl, —C(O)NH₂, —S(O)—alkyl, —NHC(O)—alkyl, —C(═NH)NH₂, —PO₃H₂, —SO₃H, —B(OH)₂, a sugar, a polyol, a glucuronide or a sugar carbamate:

R⁷ is

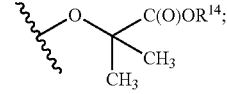

R⁸ is:

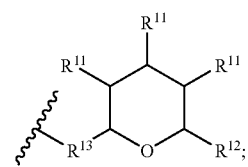

$R^9$ is

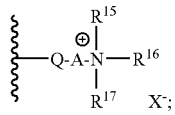

$R^{10}$ is

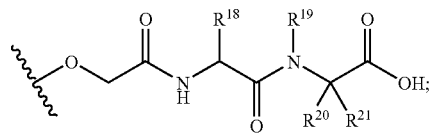

each occurrence of $R^{11}$ is independently —H, -halo, —OH, —OC(O)$R^{14}$, —OC(O)$R^{14}$ or —C(O)O$R^{14}$;

$R^{12}$ is —H, —OH, -alkylene-OH, -alkylene-OC(O)$R^{14}$, or —C(O)O$R^{14}$;

$R^{13}$ is a bond, or $R^{13}$ is -alkylene-, -alkenylene-, -oxaalkylene-, —CH(OH)-alkylene-, -alkenylene-O-alkylene-;

each occurrence of $R^{14}$ is —H or alkyl;

$R^{15}$ and A, together with the N atom to which they are attached form a 5- to 7-membered heterocycloalkyl group that has one ring N atom; or $R^{15}$ and $R^{16}$, together with the N atom to which they are attached form a 5- to 7-membered heterocycloalkyl group that has one ring N atom;

$R^{16}$ is -alkyl, or $R^{16}$ and $R^{15}$, together with the N atom to which they are both attached, join to form a 5- to 7-membered heterocycloalkyl group that has one ring N atom;

$R^{17}$ is -alkyl, or $R^{17}$ and $R^{15}$, together with the N atom to which they are both attached, join to form a 5- to 7-membered heterocycloalkyl group that has one ring N atom; or $R^{17}$ and $R^{16}$, together with the N atom to which they are both attached, join to form a 5- to 7-membered heterocycloalkyl group that has one ring N atom;

$R^{18}$ is —H, alkyl, -cycloalkyl or -aryl; wherein an alkyl group may be optionally substituted by one or more —OH, —N($R^{14}$)$_2$, —NH(C=NH)NH$_2$, —C(O)N($R^{14}$)$_2$, —C(O)O$R^{14}$, -alkoxy, -alkyl-C(O)N($R^{14}$)$_2$, —S(O)$_n$-alkyl, -cycloalkyl or -aryl; and wherein an aryl group may be optionally and independently substituted by one or two substituents selected from -halo, —OH, -alkyl or -alkoxy;

$R^{19}$ is —H, -alkyl, or -arylalkyl, or $R^{19}$ and the nitrogen atom to which it is attached and $R^{20}$ and the carbon atom to which it is attached may join to form a heterocycloalkyl group that has one ring N atom and 3-6 carbon atoms;

$R^{20}$ is —H, -alkyl, -cycloalkyl or -aryl; wherein an alkyl group may be optionally and independently substituted by one or more substituents selected from —OH, —N($R^{14}$)$_2$, —NH—C(=NH)NH$_2$, —CN, —C(O)N($R^{14}$)$_2$, —C(O)O$R^{14}$, -alkoxy, -arylalkoxy, —Si(alkyl)$_3$, —S(O)$_n$-alkyl, -cycloaklyl, -aryl or —S(O)$_n$-alkylaryl; wherein an aryl group may be optionally and independently substituted by one or two substituents selected from -halo, —OH, -alkyl or -alkoxy; or $R^{20}$ and $R^{21}$ together with the carbon atom to which they are attached, join to form a cycloalkyl group that has 3-7 ring carbon atoms;

$R^{21}$ is —H, -alkyl, -cycloalkyl or -aryl; wherein an alkyl group may be optionally and independently substituted by one or more substituents selected from —OH, —N($R^{14}$)$_2$, —NH(C=NH)NH$_2$, —CN, —C(O)N($R^{14}$)$_2$, —C(O)O$R^{14}$, -alkoxy, -arylalkoxy, —Si(alkyl)$_3$, —S(O)$_n$-alkyl, -cycloaklyl, -aryl or —S(O)$_n$-alkylaryl; wherein an aryl group may be optionally and independently substituted by one or two substituents selected from -halo, —OH, -alkyl or -alkoxy;

$R^{23}$ is

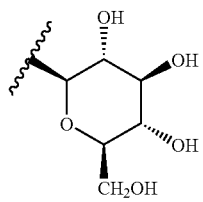 or 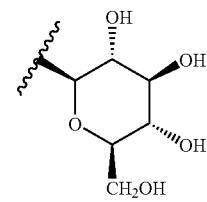

$R^{24}$ is —H, -alkyl, —C(O)—alkyl, —C(O)—N($R^{14}$)$_2$, —S(O)$_2$-alkyl or S(O)$_2$-phenyl;

$R^{25}$ is —OH or —N$R^{14}R^{24}$;

$R^{26}$ is —C(O)—alkyl, —C(O)—N($R^{14}$)$_2$, —S(O)$_2$-alkyl or S(O)$_2$-phenyl;

A is -alkylene-, -alkenylene-, -alkynylene-, -arylene-, -arylalkylene- or -oxaalkylene-, and when Q is absent, A may additionally be —C(O)— or —OC(O)—;

Q is a bond, or Q is —O—, —S—, —NH—, —CH$_2$O—, —CH$_2$NH—, —C(O)—, —C(O)NH—, —NHC(O)—, —OC(O)—, —C(O)O—, —NHC(O)NH—, —OC(O)NH— or —NHC(O)O—;

X⁻ is any anion;

each occurrence of n is independently an integer ranging from 0 to 2;

u is an integer from 0 to 3; and v is an integer from 0 to 3, such that the sum of u and v is from 3 to 5.

2. The compound of claim 1 wherein $R^1$ is selected from the group consisting of: —H, -phenyl, -phenyl substituted with -alkyl, -phenyl substituted with -halo, -phenyl substituted with —NO$_2$, -phenyl substituted with —OH, -phenyl substituted with —C(O)OH, -phenyl substituted with —O-alkyl, -phenyl substituted with —CF$_3$, phenyl which is fused to a heteroaryl ring, phenyl which is fused to a heterocycloalkyl ring, pyridyl, -2-pyridyl, -benzyl, and -4-fluorophenyl.

3. The compound of claim 1 wherein $R^1$ is selected from the group consisting of: benzofuranyl, indazolyl, benzothiazolyl, benzofuranyl substituted with a —COOH or a —CH$_2$COOH group, indazolyl substituted with a —COOH or a —CH$_2$COOH group, benzothiazolyl substituted with a —COOH or a —CH$_2$COOH group.

4. The compound of claim 1 wherein $a^1$ is:

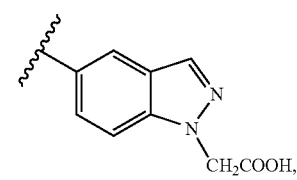

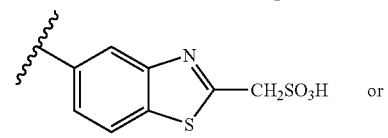 or

121

-continued

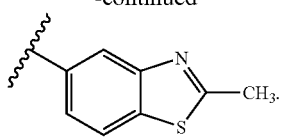

5. The compound of claim 1 wherein $a^I$ is selected from the group consisting of:

(a) -heteroaryl,

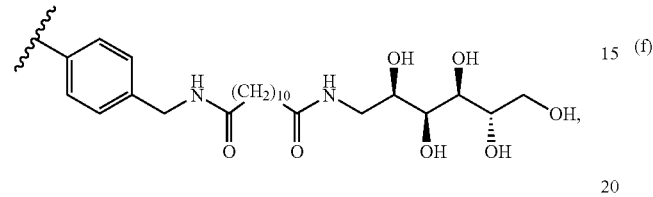

(b) —$(CH_2)_n$-phenyl wherein the phenyl group is substituted with

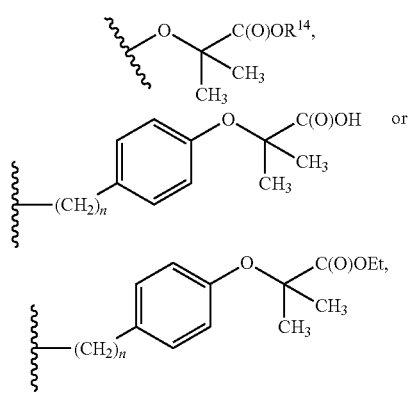

(c) —$(CH_2)_n$-phenyl, wherein the phenyl group is substituted with

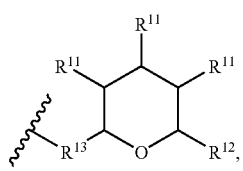

(d) —$(CH_2)_n$-phenyl, wherein the phenyl group is substituted with

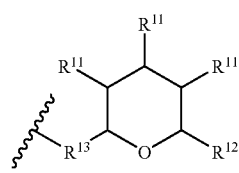

wherein $R^{13}$ is a bond, each occurrence of $R^{11}$ is —OH or —OAc, and $R^{12}$ is —$CH_2OH$ or —$CH_2OAc$, (e) —$(CH_2)_n$-phenyl, wherein the phenyl group is substituted with

122

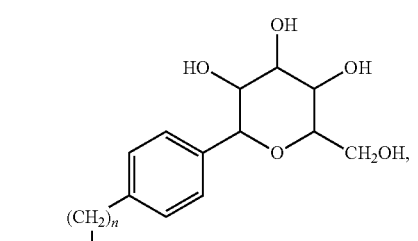

wherein $R^{13}$ is -alkylene-, -oxaalkylene- or -alkenylene-, each occurrence of $R^{11}$ is —OH or —OAc, and $R^{12}$ is —$CH_2OH$ or —$CH_2OAc$, (f)

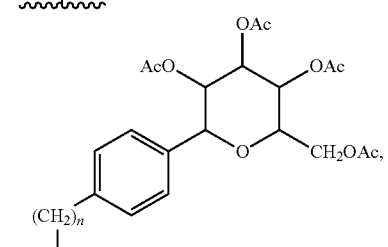

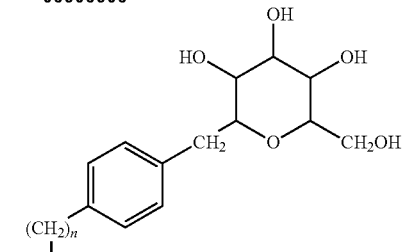

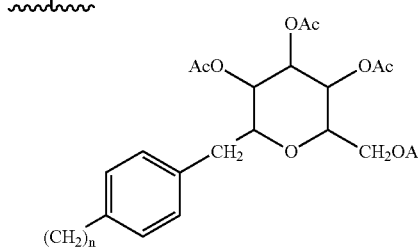

(g) -phenyl which is substituted with

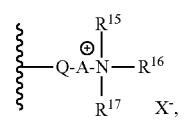

(h)

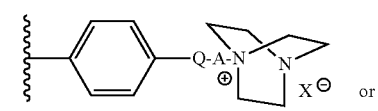

or

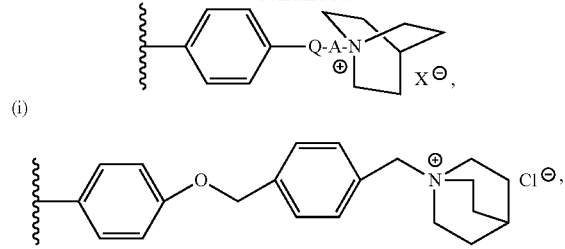

(j) phenyl which is substituted with —C≡C—CH$_2$NR$^{14}$R$^{24}$, —C≡C—CH$_2$C(O)OR$^{25}$ or -alkylene—NR$^{14}$R$^{26}$, and (k) —OR$^{23}$.

6. The compound of claim 1 wherein R$^3$ is selected from the group consisting of:

(a) —H, (b) is aryl, (c) phenyl substituted with —F, —Br or —I, (d) phenyl substituted with —OH, (e) phenyl substituted with —OCH$_3$, (f) heteroaryl, (g)

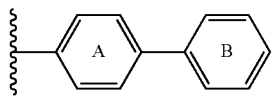

wherein each of rings A and B may be optionally and independently substituted with 1-5 groups selected from -halo, —OH, -alkyl, -alkoxy, —SH, —N(R$^{14}$)$_2$, —NO$_2$, —CN, —CF$_3$, —OC(O)R$^{14}$, —OC(O)—R$^{14}$, —C(O)OR$^{14}$, —C(O)O—R$^{14}$, R$^6$-aryl-, R$^7$, R$^8$, R$^9$ or R$^{10}$, (h)

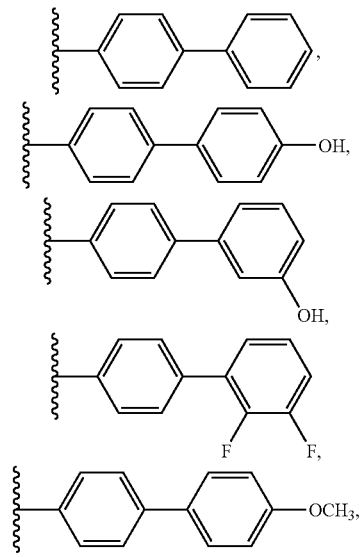

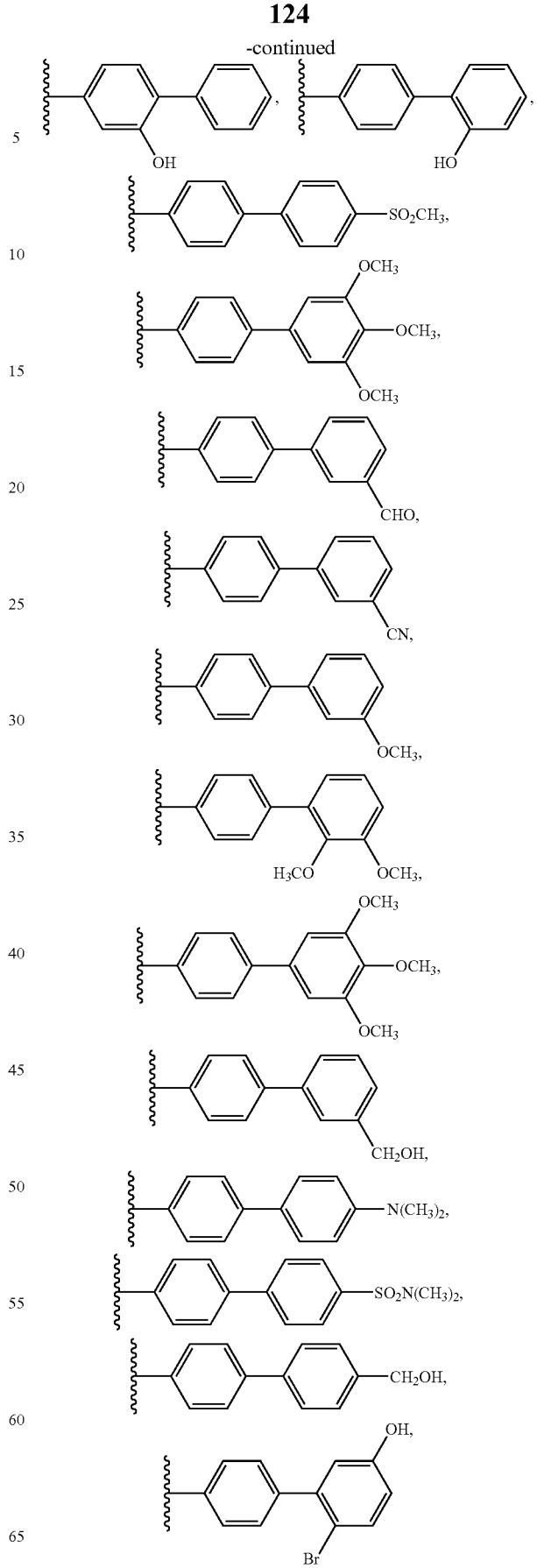

-continued
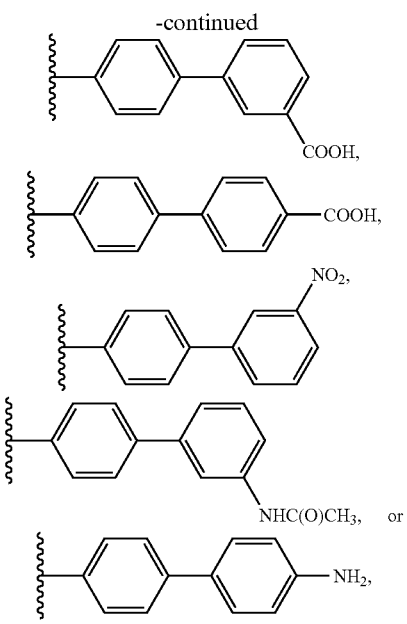
(i) -phenyl which is substituted with
(j)
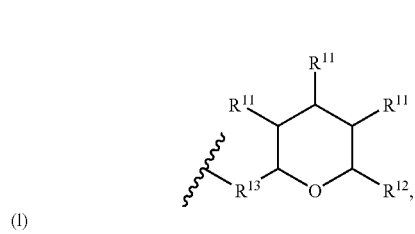
(j)
(k) -phenyl which is substituted with
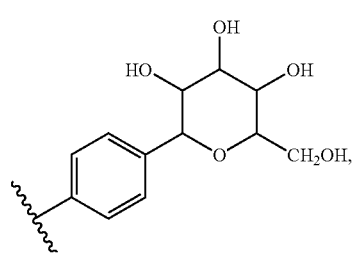
(l)
-continued
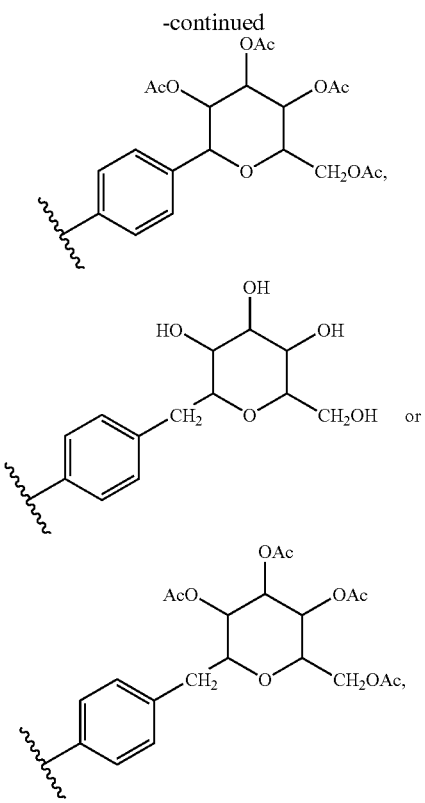
(m) -phenyl which is substituted with
wherein $R^{13}$ is -alkylene-, -oxaalkylene- or -alkenylene-, each occurrence of $R^{11}$ is —OH or —OAc, and $R^{12}$ is —CH$_2$OH or —CH$_2$OAc,
(n) -phenyl which is substituted with
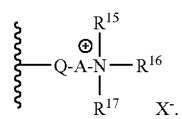
(o)

-continued (p)

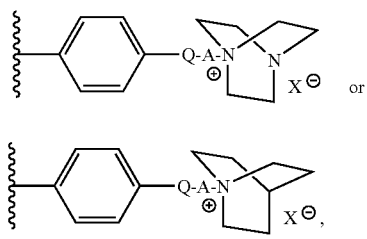

wherein-Q-A- is

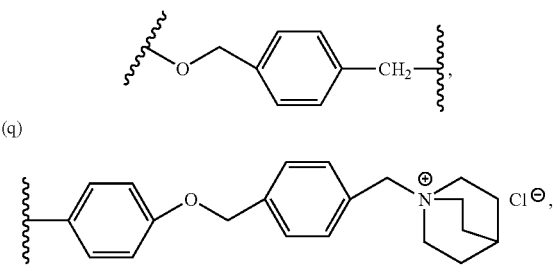

(q)

(r)

(s)

(t) phenyl which is substituted with

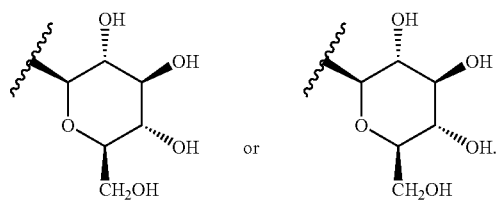

7. The compound of claim 1 wherein R³ is selected from the group consisting of: phenyl substituted with —F and phenyl substituted with —Br.

8. The compound of claim 1 wherein R² is selected from the group consisting of: pyridyl, pyrimidinyl, and benzoimidazolyl-.

9. The compound of claim 1 having the formula:

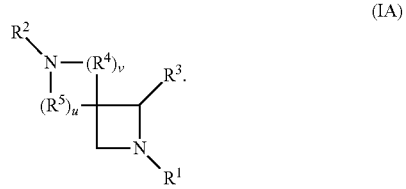

(IA)

10. The compound of claim 1 having the formula:

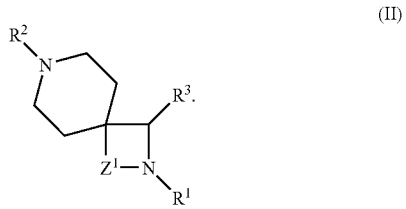

(II)

11. The compound of claim 1 having the formula

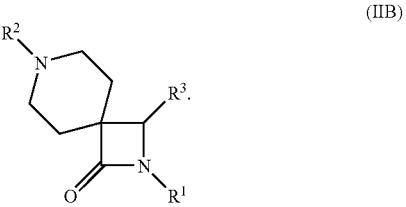

(IIB)

12. The compound of claim 1 wherein: R² is selected from the group consisting of: (A) heteroaryl; and (B) substituted heteroaryl.

13. The compound of claim 12 wherein: R² is selected from the group consisting of: pyridyl, pyrimidinyl, pyrazinyl, benzoimidazolyl-, quinazolinyl, isoquinolinyl, quinolinyl, substituted pyridyl, substituted pyrimidinyl, substituted pyrazinyl, substituted benzoimidazolyl, substituted quinazolinyl, substituted isoquinolinyl, and substituted quinolinyl; and wherein said substituted groups are substituted with 1 to 3 substituents independently selected from the group consisting of: alkyl, halo, CN, —CF₃, alkoxy, halo substituted alkoxy, cycloalkyl, and halo substituted alkyl.

14. The compound of claim 13 wherein said substituents on said substituted R² groups are selected from the group consisting of:
Cl, F, Br, —CF₃, —OCH₃, cyclopropyl, —OCF₃, —CF₂CH₃ and —CN.

15. A pharmaceutical composition comprising an effective amount of at least one compound of claim 1 and a pharmaceutically acceptable carrier.

16. A method of treating pain comprising administering to a patient in need of such treatment an effective amount of at least one compound of claim 1.

17. The method of claim 16 wherein said compound is administered in combination with at least one additional agent for treating pain, and said additional agent for treating pain is selected from the group consisting of:

(A) non-opioid analgesics selected from the group consisting of:
acetylsalicylic acid, choline magnesium trisalicylate, acetaminophen, ibuprofen, fenoprofen, diflusinal, and naproxen;

(B) opioid analgesics selected from the group consisting of: morphine, hydromorphone, methadone, levorphanol, fentanyl, oxycodone, and oxymorphone;

(C) steroids selected from the group consisting of: prednisolone, fluticasone, triamcinolone, beclomethasone, mometasone, budisamide, betamethasone, dexamethasone, prednisone, flunisolide and cortisone;

(D) COX-I inhibitors selected from the group consisting of: aspirin and piroxicam;

(E) COX-II inhibitors selected from the group consisting of:
rofecoxib, celecoxib, valdecoxib and etoricoxib;

(F) agents useful for treating inflammatory bowel disease selected from the group consisting of: IL-10, steroids, and azulfidine; and (G) agents useful for treating rheumatoid arthritis selected from the group consisting of: methotrexate, azathioprine, cyclophosphamide, steroids and mycophenolate mofetil.

18. A method for inhibiting the absorption of cholesterol comprising administering to a patient in need of such treatment an effective amount of at least one compound of claim 1.

19. A method for inhibiting the absorption of cholesterol comprising administering to a patient in need of such treatment an effective amount of at least one compound of claim 1 in combination with an effective amount of at least one additional agent for treating a disorder of lipid metabolism.

20. A method for inhibiting the absorption of cholesterol comprising:
administering to a patient in need of such treatment an effective amount of at least one compound of claim 1 in combination with an effective amount of at least one nicotinic acid receptor agonist; or
administering to a patient in need of such treatment an effective amount of at least one compound of claim 1 in combination with an effective amount of at least one inhibitor of HMG—CoA reductase.

21. A method for inhibiting the absorption of cholesterol comprising administering to a patient in need of such treatment an effective amount of at least one compound of claim 1 in combination with an effective amount of at least one inhibitor of HMG—CoA reductase, and in combination with an effective amount of at least one NPC1 L1 antagonist.

22. A compound of the formula:

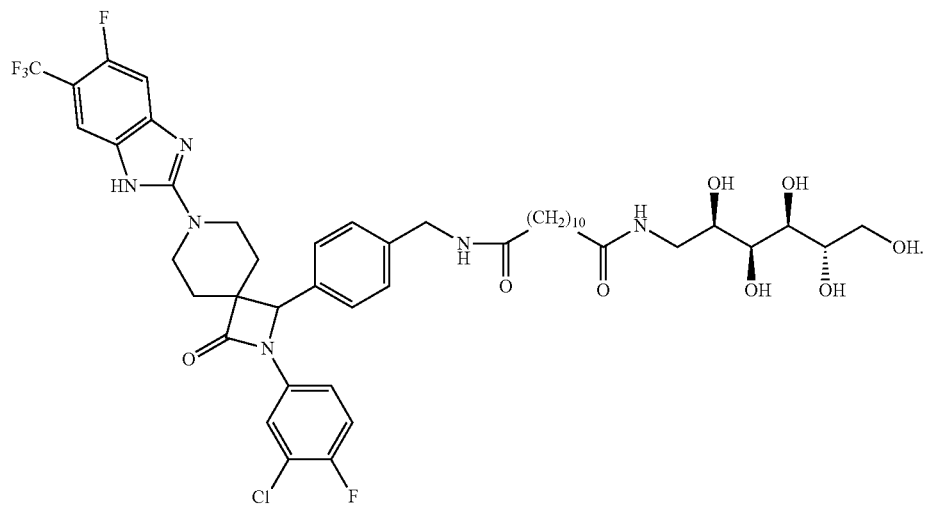

10B.1

23. A compound of the formula:

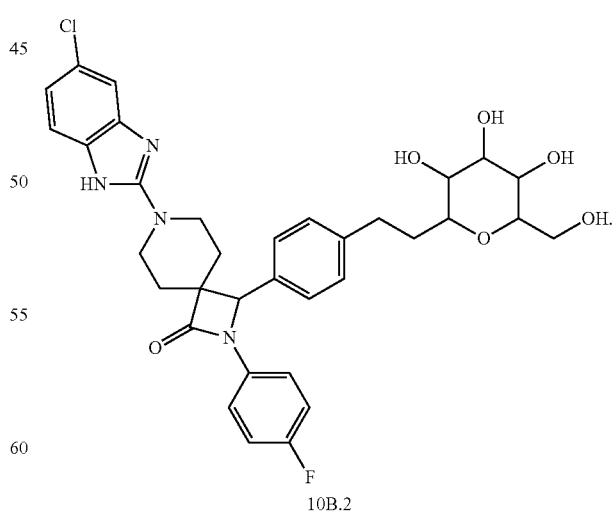

10B.2

* * * * *